United States Patent
Hawkes et al.

(10) Patent No.: US 9,850,067 B2
(45) Date of Patent: *Dec. 26, 2017

(54) PHARMACEUTICAL DISPENSING SYSTEM AND ASSOCIATED METHOD

(71) Applicant: Remedi Technology Holdings, LLC, Towson, MD (US)

(72) Inventors: Kimberly Hawkes, Columbus, PA (US); Steven E. Schneider, Lewis Center, OH (US); Thomas P. Hayes, Cambridge (CA); Richard W. Snodgrass, Columbus, OH (US); Roger J. Gerdeman, Columbus, OH (US); Wyatt Culbertson, Powell, OH (US); Steven Hoenig, Blacklick, OH (US); Justin J. Clark, Kitchener (CA); Christopher J. Fisher, Kitchener (CA)

(73) Assignee: REMEDI TECHNOLOGY HOLDINGS, LLC, Towson, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/154,585

(22) Filed: May 13, 2016

(65) Prior Publication Data

US 2016/0251160 A1    Sep. 1, 2016

Related U.S. Application Data

(63) Continuation of application No. 12/559,630, filed on Sep. 15, 2009.

(Continued)

(51) Int. Cl.
| | |
|---|---|
| *B65G 1/00* | (2006.01) |
| *B65G 1/137* | (2006.01) |
| *G07F 17/00* | (2006.01) |
| *B65G 1/04* | (2006.01) |
| *B65G 47/91* | (2006.01) |
| *B65G 59/06* | (2006.01) |
| *G06F 17/00* | (2006.01) |

(Continued)

(52) U.S. Cl.
CPC ........ *B65G 1/1376* (2013.01); *B65G 1/0471* (2013.01); *B65G 1/06* (2013.01); *B65G 1/137* (2013.01); *B65G 47/91* (2013.01); *B65G 59/062* (2013.01); *G06F 17/00* (2013.01); *G06F 19/3462* (2013.01); *G07F 17/0092* (2013.01)

(58) Field of Classification Search
CPC . G07F 17/0092; B65G 1/0471; B65G 1/1376; B65G 1/137; B65G 47/91; B65G 59/062
USPC ........................................ 221/124, 126, 133
See application file for complete search history.

(56) References Cited

U.S. PATENT DOCUMENTS

| | | |
|---|---|---|
| 3,013,693 A | 12/1961 | Griner |
| 3,247,929 A | 4/1966 | Langley |

(Continued)

OTHER PUBLICATIONS

Extended European Search Report dated May 6, 2016 in Patent Application No. 09831183.0.

(Continued)

*Primary Examiner* — Timothy Waggoner
(74) *Attorney, Agent, or Firm* — Oblon, McClelland, Maier & Neustadt, L.L.P.

(57) ABSTRACT

A dispensing system and associated method provides a turnkey solution for dispensing pharmaceutical products such as solid medications and nutritional supplements to be taken orally in health care settings, including but not limited to long term care (LTC) and assisted living settings.

22 Claims, 39 Drawing Sheets

Related U.S. Application Data

(60) Provisional application No. 61/120,209, filed on Dec. 5, 2008.

(51) Int. Cl.
*B65G 1/06* (2006.01)
*G06F 19/00* (2011.01)

(56) References Cited

U.S. PATENT DOCUMENTS

| | | |
|---|---|---|
| 3,386,558 A | 6/1968 | Benatar |
| 3,511,395 A | 5/1970 | Brown, Jr. |
| 3,527,368 A | 9/1970 | Bambara |
| 3,701,297 A | 10/1972 | Kovic |
| 3,718,328 A | 2/1973 | Comstock |
| 3,937,458 A | 2/1976 | Langen |
| 3,998,356 A | 12/1976 | Christensen |
| 4,194,442 A | 3/1980 | Martelli |
| 4,338,083 A | 7/1982 | Andrae |
| 4,385,859 A | 5/1983 | Goossens |
| 4,537,587 A | 8/1985 | Langen |
| 4,655,026 A | 4/1987 | Wigoda |
| 4,760,909 A | 8/1988 | Dudley et al. |
| 4,822,234 A | 4/1989 | Johnson et al. |
| 4,870,799 A | 10/1989 | Bergerioux et al. |
| 4,874,076 A | 10/1989 | Kaplan et al. |
| 4,880,102 A | 11/1989 | Indrebo |
| 4,901,843 A | 2/1990 | Lashyro |
| 5,054,761 A | 10/1991 | Dietrich et al. |
| 5,061,231 A | 10/1991 | Dietrich et al. |
| 5,104,369 A | 4/1992 | Calvert |
| 5,161,791 A | 11/1992 | Akiyama et al. |
| 5,271,703 A | 12/1993 | Lindqvist et al. |
| 5,288,201 A | 2/1994 | Pippin |
| 5,299,907 A | 4/1994 | Dal Pozzo |
| 5,322,406 A | 6/1994 | Pippin et al. |
| 5,392,927 A | 2/1995 | Haverkamp Begermann et al. |
| 5,431,299 A | 7/1995 | Brewer et al. |
| 5,454,688 A | 10/1995 | Pippin |
| 5,468,110 A | 11/1995 | McDonald et al. |
| 5,478,183 A | 12/1995 | Savigny |
| 5,511,772 A | 4/1996 | Ganz et al. |
| 5,533,606 A | 7/1996 | Yuyama |
| 5,551,822 A | 9/1996 | Pippin et al. |
| 5,564,893 A | 10/1996 | Tacchi et al. |
| 5,573,368 A | 11/1996 | Freudesperger |
| 5,582,324 A | 12/1996 | Pippin et al. |
| 5,597,995 A | 1/1997 | Williams et al. |
| 5,604,692 A | 2/1997 | Yuyama |
| 5,666,492 A | 9/1997 | Rhodes et al. |
| 5,713,718 A | 2/1998 | Okura et al. |
| 5,720,157 A | 2/1998 | Ross |
| 5,755,551 A | 5/1998 | Saeki et al. |
| 5,755,552 A | 5/1998 | Iwasaka et al. |
| 5,758,095 A | 5/1998 | Albaum et al. |
| 5,768,139 A | 6/1998 | Pippin et al. |
| 5,771,657 A | 6/1998 | Lasher et al. |
| 5,772,392 A | 6/1998 | Okura et al. |
| 5,797,515 A | 8/1998 | Liff et al. |
| 5,832,693 A | 11/1998 | Yuyama et al. |
| 5,833,599 A | 11/1998 | Schrier et al. |
| 5,912,818 A | 6/1999 | McGrady et al. |
| 5,930,145 A | 7/1999 | Yuyama et al. |
| 5,934,864 A | 8/1999 | Lyon et al. |
| 5,945,651 A | 8/1999 | Chorosinski et al. |
| RE36,329 E | 10/1999 | Laroche |
| 5,963,453 A | 10/1999 | East |
| 5,970,462 A | 10/1999 | Reichert |
| 5,988,858 A | 11/1999 | Yuyama et al. |
| 5,992,742 A | 11/1999 | Sullivan et al. |
| 6,061,607 A | 5/2000 | Bradley et al. |
| 6,064,921 A | 5/2000 | Pippin et al. |
| 6,068,156 A | 5/2000 | Liff et al. |
| 6,101,787 A | 8/2000 | Brintazzoli et al. |
| 6,152,364 A | 11/2000 | Schoonen et al. |
| 6,170,230 B1 | 1/2001 | Chudy et al. |
| 6,170,634 B1 | 1/2001 | Jaquet |
| 6,202,923 B1 | 3/2001 | Boyer et al. |
| 6,206,590 B1 | 3/2001 | Thomas et al. |
| 6,247,890 B1 | 6/2001 | Chang et al. |
| 6,256,967 B1 | 7/2001 | Hebron et al. |
| 6,260,761 B1 | 7/2001 | Peoples, Jr. |
| 6,289,260 B1 | 9/2001 | Bradley et al. |
| 6,308,109 B1 | 10/2001 | Yuyama et al. |
| 6,317,648 B1 | 11/2001 | Sleep et al. |
| 6,347,709 B1 | 2/2002 | Biehl et al. |
| 6,367,232 B2 | 4/2002 | Kim |
| 6,370,841 B1 | 4/2002 | Chudy et al. |
| 6,377,867 B1 | 4/2002 | Bradley et al. |
| 6,383,123 B1 | 5/2002 | Ehring et al. |
| 6,446,416 B1 | 9/2002 | Kuhn et al. |
| 6,449,927 B2 | 9/2002 | Hebron et al. |
| 6,474,635 B2 | 11/2002 | Ruf et al. |
| 6,522,945 B2 | 2/2003 | Sleep et al. |
| 6,564,121 B1 | 5/2003 | Wallace et al. |
| 6,597,969 B2 | 7/2003 | Greenwald et al. |
| 6,625,952 B1 | 9/2003 | Chudy et al. |
| 6,636,780 B1 | 10/2003 | Haitin et al. |
| 6,687,676 B1 | 2/2004 | Denny |
| 6,711,460 B1 | 3/2004 | Reese |
| 6,728,684 B1 | 4/2004 | Reichert |
| 6,742,671 B2 | 6/2004 | Hebron et al. |
| 6,847,861 B2 | 1/2005 | Lunak et al. |
| 6,883,681 B1 | 4/2005 | Coughlin et al. |
| 6,892,512 B2 | 5/2005 | Rice et al. |
| 6,910,601 B2 | 6/2005 | Thomas et al. |
| 6,964,146 B2 | 11/2005 | LaRocca |
| 6,970,769 B2 | 11/2005 | Rice et al. |
| 6,983,579 B2 | 1/2006 | Rice et al. |
| 7,006,893 B2 | 2/2006 | Hart et al. |
| 7,010,389 B2 | 3/2006 | Lunak et al. |
| 7,010,899 B2 | 3/2006 | McErlean et al. |
| 7,058,584 B2 | 6/2006 | Kosinski et al. |
| 7,072,737 B2 | 7/2006 | Lunak et al. |
| 7,100,792 B2 | 9/2006 | Hunter et al. |
| 7,110,855 B2 | 9/2006 | Leishman |
| 7,121,427 B2 | 10/2006 | Guerra |
| 7,123,989 B2 | 10/2006 | Pinney et al. |
| 7,155,306 B2 | 12/2006 | Haitin et al. |
| 7,185,477 B2 | 3/2007 | Rice et al. |
| 7,249,688 B2 | 7/2007 | Hunter |
| 2003/0200726 A1 | 10/2003 | Rast |
| 2004/0040975 A1 | 3/2004 | Hunter et al. |
| 2007/0162179 A1 | 7/2007 | Freudelsperger |
| 2007/0270998 A1 | 11/2007 | Luciano, Jr. et al. |
| 2008/0006647 A1 | 1/2008 | Hunter et al. |
| 2008/0138187 A1 | 6/2008 | Christ |

OTHER PUBLICATIONS

International Searching Authority, The International Search Report and The Written Opinion of the International Searching Authority, or the Declaration, PCT/US2009/066756, dated Feb. 1, 2010, 22 pages.

Office Action dated Jul. 5, 2016 in Canadian Patent Application No. 2,745,147.

Chinese Office Action dated Aug. 20, 2013, in China Patent Application No. 200980155637.5 (with partial English translation).

Mexican Office Action dated Sep. 2, 2014 in Patent Application No. 2011/005873 with English Translation.

Mexican Communication of Substantive Examination, dated Mar. 27, 2014, Folio No. 27167 issued in PCT Patent Application No. MX/a/2011/005873 filed Dec. 4, 2009, 4 pgs.

Combined Chinese Office Action and Search Report dated Nov. 5, 2012 in Chinese Patent Application No. 200980155637.5 (w/English Translation of Categories of Cited Documents).

Office Action dated Mar. 17, 2016, in Korea Patent Application No. 2011-7015449, 2 pgs.

Office Action dated Jul. 21, 2016 in Mexican Patent Application No. Mx/a/2014/014638 filed Jun. 3, 2011 (with English language translation).

(56) References Cited

OTHER PUBLICATIONS

Korean Office Action dated Sep. 9, 2016 in Patent Application No. 10-2011-7015449.
Office Action dated May 23, 2017, in Canada Patent Application No. 2,745,147.

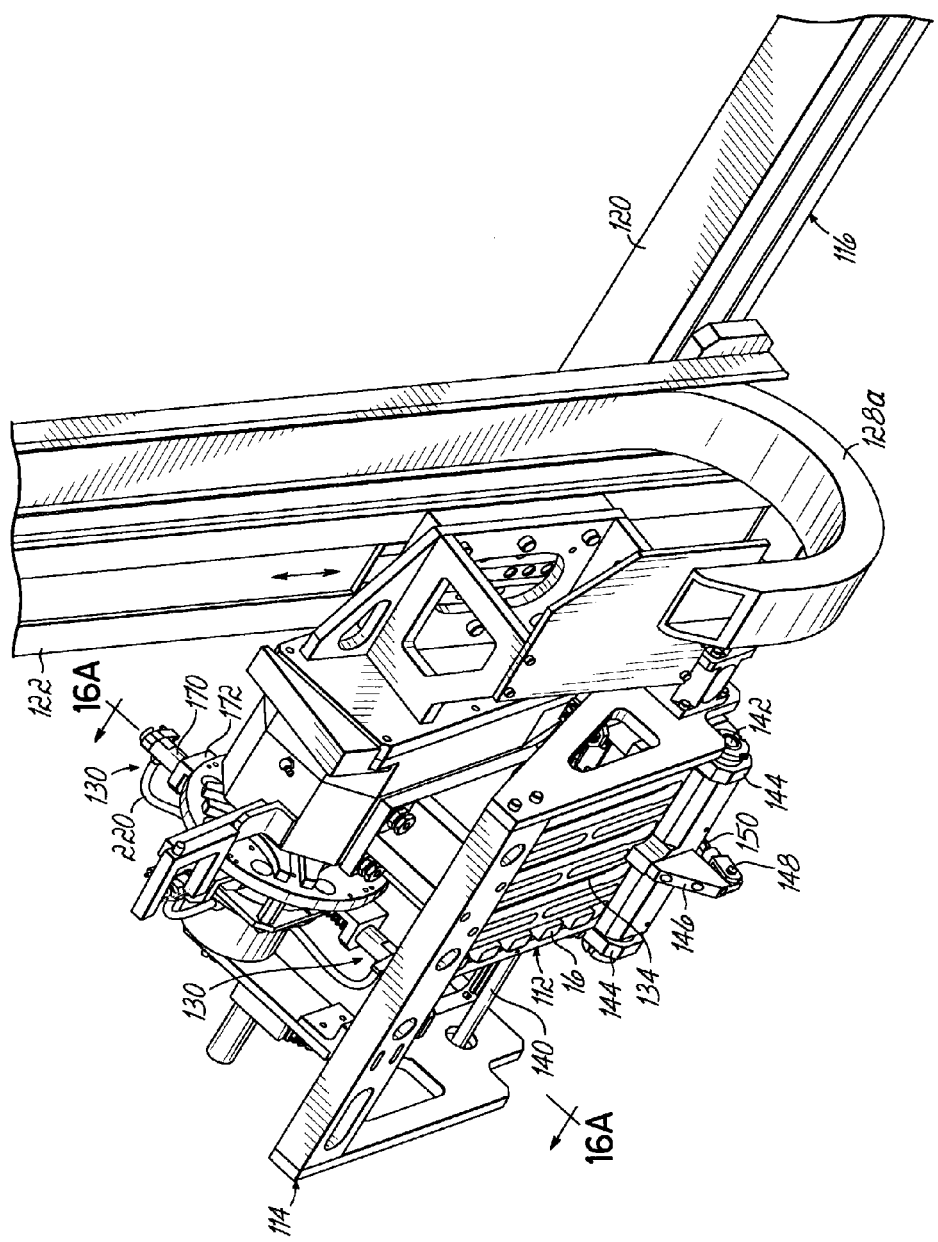

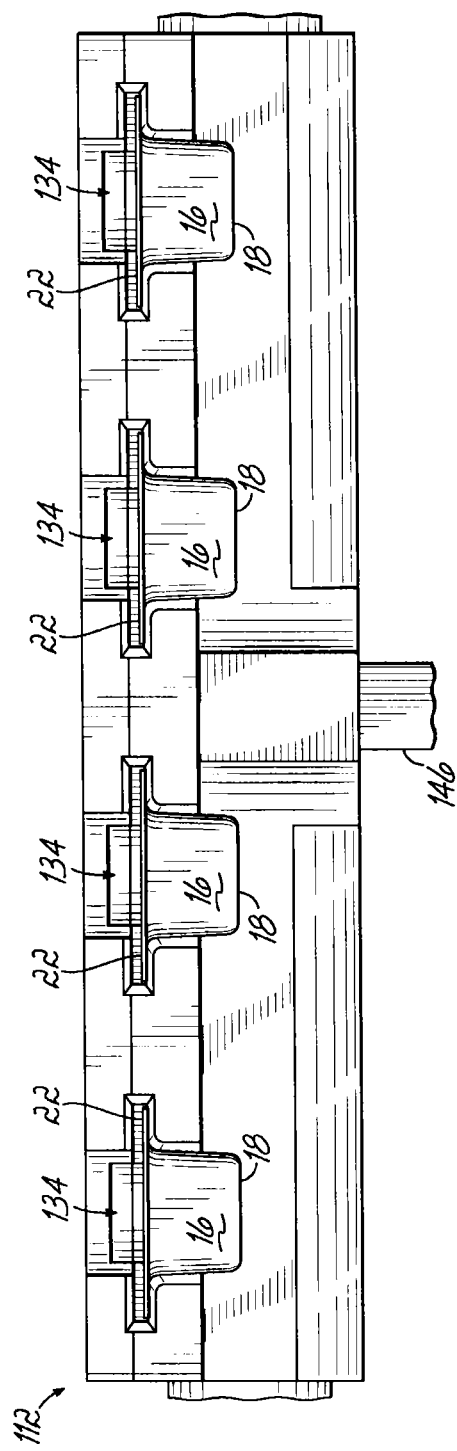

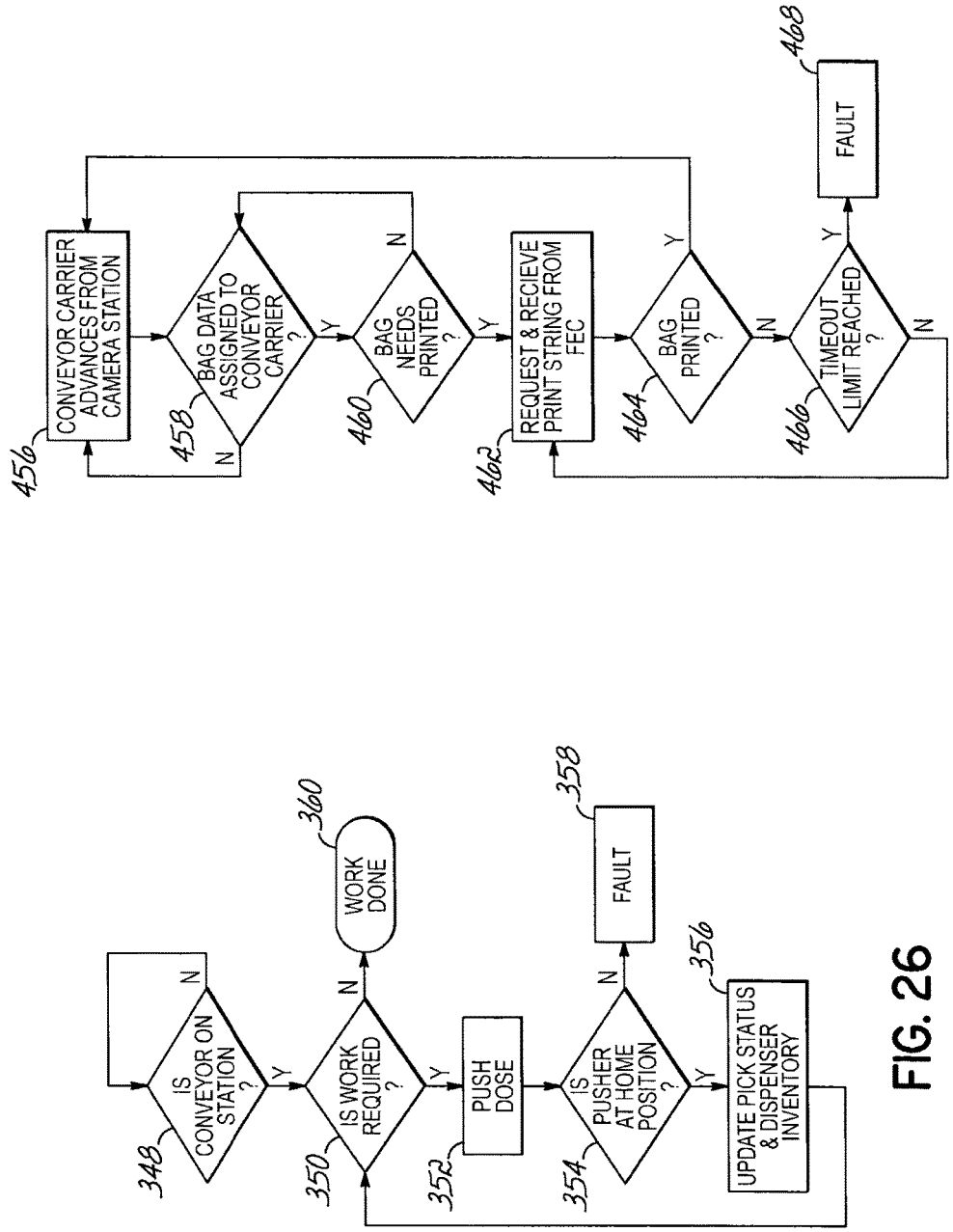

PHARMACEUTICAL DISPENSING SYSTEM AND ASSOCIATED METHOD

CROSS-REFERENCE TO RELATED APPLICATION

This application is a continuation application of, and claims the benefit of priority under 35 U.S.C. §120 from, U.S. application Ser. No. 12/559,630, filed Sep. 15, 2009, which claims priority from, U.S. Provisional Patent Application Ser. No. 61/120,209, filed Dec. 5, 2008. The entire contents of each of the above applications are incorporated herein by reference.

BACKGROUND OF THE INVENTION

This invention relates generally to systems and associated methods for distributing pharmaceutical products and, more particularly, to automated dispensing systems and associated methods for distributing pharmaceutical products for individual patients in health care facilities.

Hospitals, long term care and other health care facilities distribute and administer pharmaceutical products to patients in individual doses numerous times per day. Pharmaceutical products such as prescription medications, nutritional supplements and the like are often stored in bulk by pharmacies and are repackaged into containers of multiple doses based on individual prescriptions for retail or outpatient distribution. For inpatient or in-facility distribution, pharmacies also often repackage bulk pharmaceuticals into "unit of use" or "unit dose" packages, for example, multiple blister packs that are connected together in a strip that contain multiple single doses of the pharmaceutical product.

The traditional method for distributing individual dosage units of pharmaceutical products to patients begins with the generation of a patient order by a physician for particular medications. The patient order is delivered to the pharmacy. There, the process of interpreting the patient order, pulling the specified medication or supplements from the drug storage areas, packaging the medication or supplements, and labeling the package is routinely done manually by pharmacy support personnel. After a final check by the facility pharmacist, the packaged individual dosage units are ready for distribution. In large facilities, the packages containing the patient's order are forwarded to individual nursing units where nursing staffers distribute and administer them to the patients.

There are several disadvantages associated with the traditional method of distributing individual dosage units of pharmaceutical products. To begin with, the process is labor and cost intensive. Many separate labor steps are required to fill a single patient order. In large facilities servicing hundreds of patients each day, the staffing requirements to rapidly process patient orders are substantial. In addition, with so many human inputs required in the existing process, there may also be a risk of human error.

As an attempt to address at least some of the issues with respect to staffing requirements and human error, a variety of automated medication dispensing systems have been developed. The current landscape for automated medication dispensing is dominated by a 30-day system utilizing either "bingo cards" or unit doses supplied in 30-day box. The known systems provide a 30-day or other multi-day supply for each patient pass-time for each prescription on a relatively long term basis. In the event the patient is discharged or the treatment is changed, the unused portion of the 30-day supply cannot be cost effectively reused even though the product may be labeled appropriately. The labor cost required to reintroduce the pharmaceutical products back into the distribution system and to maintain the integrity and traceability of manufacturer and expiration data exceeds the value of the pharmaceutical products, even if the substantial restocking fees are paid by the healthcare system. As a result, such unused pharmaceutical products are returned to the pharmacy for disposal. This disposal of unused pharmaceutical products is a significant waste of those resources as well as a detriment to the environment.

One known pharmaceutical package dispensing system automates various aspects of the task of filling patient orders for units of use pharmaceuticals. The system employs a number of storage cartridges arranged in stacked rows on a frame. The cartridges contain strips of unit dose packages of pharmaceutical products. The packages consist of individual unit dose blisters. Each of the blisters contains a unit of use, e.g., a single tablet or capsule. Several blister packages are joined together to form the linear strips such that a given cartridge may contain several such strips stacked vertically or in roll form. Each cartridge is provided with a forward-facing opening through which a portion of the lowermost blister strip contained therein projects. A pick device is movable adjacent a respective row of cartridges to a desired location adjacent a cartridge. The pick device pulls the blister strip out of the cartridge and a cutting blade mounted on the pick device cuts an individual blister from the strip. The severed blister pack free-falls onto a conveyor or into a bin on the pick device or elsewhere and when the pick device has finished picking blisters for the order, it discharges the blisters in the bin onto a tray. The tray serves as an accumulation point servicing multiple pick devices. The tray is moved to a discharge location to dump the blisters by gravity from the tray into a funnel of a packaging station.

The drug dispensing machine described above and similar such systems have several disadvantages. To begin with, only one tray and discharge slide for the multiple pick devices is provided. Therefore, a pick device may have to wait for a tray to empty, which significantly reduces the picking efficiency of the pick devices and throughput of the dispensing machine. Second, the cartridge, pick device and bin design can lead to difficulties when a given blister strip is pulled, cut and dropped from the cartridge. The opening through which the blister strips project allows for significant lateral play by the strips. Further, the size of the unit doses may vary greatly and pick device retrieval and cutting mechanisms must be adjusted to accommodate unit doses of different sizes. This can lead to misalignments with the cutting blade. The gravity free-fall of the severed unit doses often results in missing or jammed unit doses producing incomplete orders and requiring manual intervention to dislodge, retrieve and/or collect the errant unit doses.

Hence, there is a continuing need to improve a system and overall methodology for dispensing medication orders for individual patients in health care facilities.

SUMMARY OF THE INVENTION

This invention has many aspects and embodiments generally directed to a process or method and associated system and sub-systems to provide a turnkey solution for dispensing medications and nutritional supplements to be taken administered in health care settings, including but not limited to long term care (LTC) and assisted living settings. Bulk pharmaceutical products are converted to individual packaged unit doses and ultimately individually packaged pass-time bags for each patient on a 24-hour schedule. Additionally, inventory management is also automated. The various safeguards and measures built into the system of this invention include unit dose scanning at various steps as well as personal inspections, as needed, to increase patient safety, eliminate waste and increase labor efficiency by reducing and/or minimizing the disposal of unused pharmaceutical products.

One objective of this system and methodology is to avoid the need for disposal of prescriptions medications and nutritional supplements thereby attacking the waste and inefficiency issues at their source. This invention in one embodiment is a pharmaceutical dispenser for prescriptions, medication and nutritional supplements. Positive control of each unit dose package is maintained throughout the entire process. In other words, gravity feed and the random nature of medications freefalling through the system is avoided according to one aspect of this invention.

The individual pharmaceutical products are packaged in unit dose packages and multiple such unit dose packages are arranged in a storage tube. After the filled storage tubes are prepared and entered into the inventory database, they are loaded into an automated dispenser at appropriate locations for the automated filling and packaging of individual med pass patient orders. The dispenser provides an automated solution to the efficient and timely preparation of med pass orders handled in LTC and assisted living settings by filling individual med pass orders for each patient and assembling them in a bag of unit dose pharmaceutical products and staking individual bags together. The dispensing system of this invention may be located remotely from the LTC facility and will serve multiple facilities. The staked bags are then packed in a tote and delivered to the LTC for distribution. At each step in the process, the unit dose pharmaceutical products are tracked via a bar code scanner and the status of each unit dose is cataloged and regularly updated in the information management system database.

The design of the overall system and its individual components according to this invention allows for physical control of each unit dose from start to finish without any unit dose "free fall" in the system. This process is automated and does not rely upon manual sorting. The med pass bags are consolidated into the final shipping container and do not require manual sorting and packing.

The dispenser according to one embodiment of this invention utilizes two distinct dispensing modules or schemes for dispensing the unit dose packages; however, each of the unit dose packages are housed within storage tubes in the dispenser. One aspect of this invention is multiple buffers in which unit dose packages for a particular patient order are selected from the storage tubes in advance of their being assembled into the patient's order thereby enhancing the speed and efficiency of filling patient orders.

The dispensing system according to one aspect of this invention is an automated medication/supplement dispenser configured to store and dispense individual unit doses of pharmaceutical products and to assembly the dispensed pharmaceutical products into individual time-pass medication (med pass) orders to be delivered to a healthcare or LTC facility. The dispenser is divided into distinct dispensing modules dedicated to dispensing pharmaceutical products based on the frequency of demand of these items. A first dispensing module of the dispenser stores and dispensing high-demand pharmaceutical products, and a second dispensing module of the dispenser is configured to store and dispense low/medium demand pharmaceutical products.

BRIEF DESCRIPTION OF THE DRAWINGS

The various features and advantages of this invention, and the manner of attaining them, will become more apparent and the invention itself will be better understood by reference to the following description of embodiments of the invention taken in conjunction with the accompanying drawings, wherein:

FIG. 15 is a front elevational view of a pick device and associated gantry for moving the pick device relative to the bank in the second module of the dispensing system according to one embodiment of this invention;

FIG. 15A is a partial cross-sectional view taken along line 15A-15A of FIG. 22;

FIG. 26 is a flow chart depicting the operation of a high-demand dispensing module according to one embodiment of the dispensing system of this invention;

FIG. 30 is a flow diagram depicting a printer for the bagging system associated with one embodiment of this invention.

DETAILED DESCRIPTION OF THE INVENTION

Figure 1:
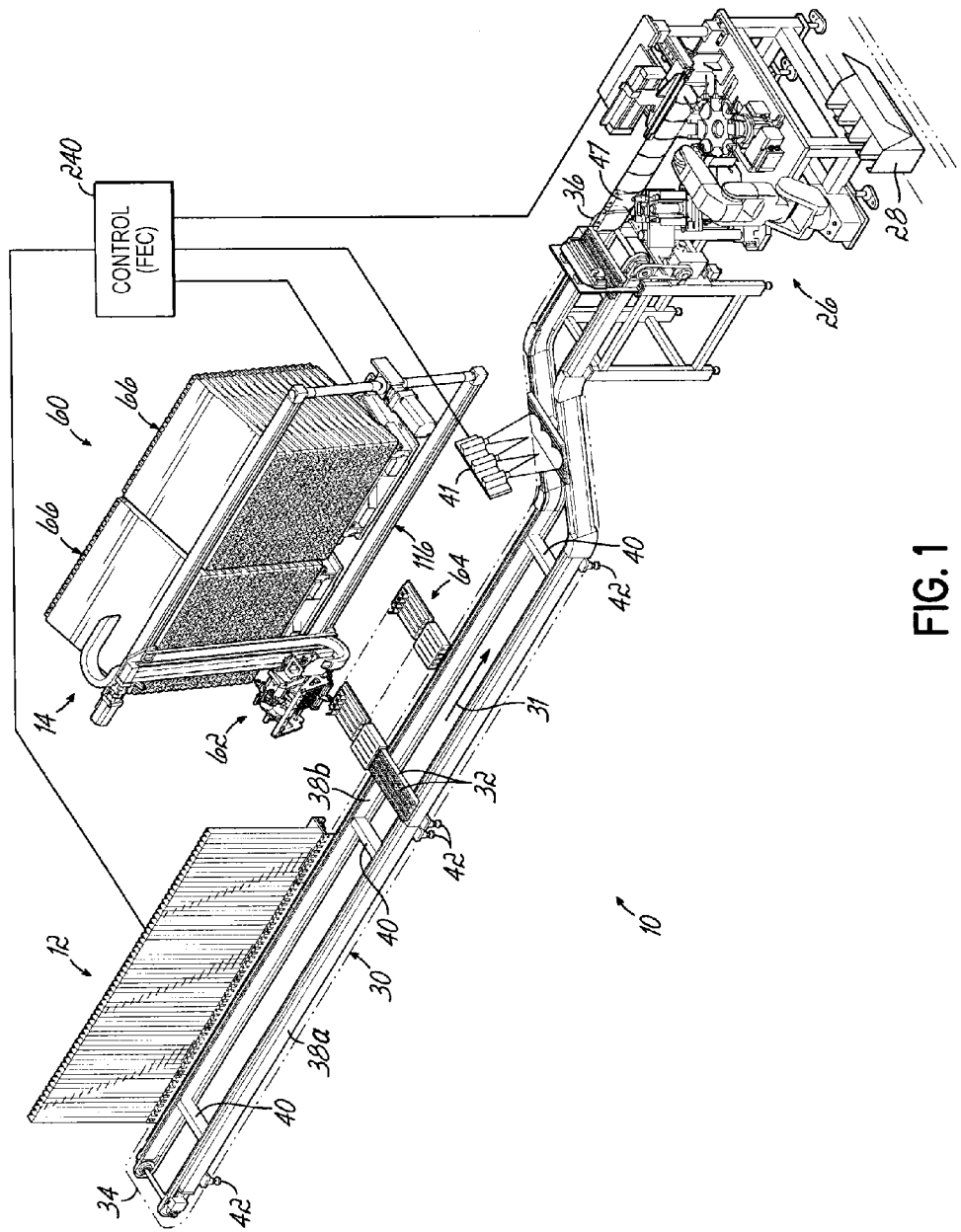
FIG. 1 is a perspective view of a pharmaceutical dispensing system according to one embodiment of this invention.

A dispensing system 10 according to one embodiment is shown in FIG. 1 and is configured to store and dispense individually packaged and labeled doses of medications/supplements, and to assemble the dispensed medications/supplements into individual medication orders, such as time-pass medication orders to be delivered to a long-term care (LTC) facility, for example. It will be appreciated, however, that a dispensing system 10 in accordance with this disclosure may alternatively be configured to dispense other items. The dispensing system 10 is divided into distinct modules that are dedicated to dispensing the medications/supplements based on the demand, or order frequency, of those items. In the embodiment shown, a first module 12 is configured to dispense medications/supplements having a relatively high-demand or order frequency, and a second module 14 of the dispensing system 10 is configured to store and dispense medications/supplements having a relatively lower demand or order frequency.

In the embodiment shown and described herein, the medications/supplements are provided in packages 16 sized to receive an individual dose of a particular medication/supplement, commonly referred to as a blister pack. With reference to FIG. 2A, an exemplary package 16 includes a base portion 18 defining a cavity for receiving the individual dose of the medication/supplement 20, and a generally planar closure 22 disposed over an open end of the base portion 18. The peripheral dimensions of the blister capsule base portion 18 of the unit dose packages are smaller than the perimeter dimensions of the upper, generally planar closure 22 of the packages 16. The packages 16 may be provided with information 24 related to the medication/supplement 20 contained in the packages 16, such as the name of the medication/supplement 20, the manufacturer, the date manufactured, the lot number, and/or other information. In the embodiment shown, information 24 is provided on the closure portion 22 and includes machine-readable information, such as a barcode, that may be used to facilitate the automated storing, tracking, dispensing, and packaging of orders.

With continued reference to FIG. 1, the dispensing system 10 further includes an endless conveyor 30 with a plurality of carriers 32 that move past the first, high-demand module 12 and the second, low-demand module 14 to collect ordered medications/supplements and carry them to a designated location for further processing. In the embodiment shown, a first, upstream end 34 of the conveyor 30 is positioned adjacent the high-demand module 12. The carriers 32 are moved along the conveyor 30 past the high-demand module 12 and the low-demand module 14 toward a second, downstream end 36 where the medications/supplements are packaged in packaging or bagger station 26 into boxes, cartons or totes 28 for delivery to the LTC facility. Each carrier 32 defines a dedicated or designated space on the conveyor 30 for a particular order.

In the embodiment shown in FIG. 1, the conveyor 30 has a pair of oppositely disposed, longitudinally extending rails 38a, and 38b supporting the plurality of carriers 32. The conveyor 30 may further have cross-members 40 extending between the rails 38a, 38b and support legs 42 configured to support the longitudinally extending rails 38a, 38b a distance above a floor surface. The endless conveyor 30 carries the plurality of carriers 32 linked together along a conveyor path 31. The conveyor 30 and associated conveyor path 31 extends from an upstream end 34 toward the downstream end 36 of the dispensing system 10. The various components, modules and stations of the dispensing system are each coupled to an operator's control station 240 for command and control of the dispensing system 10.

Figure 3:
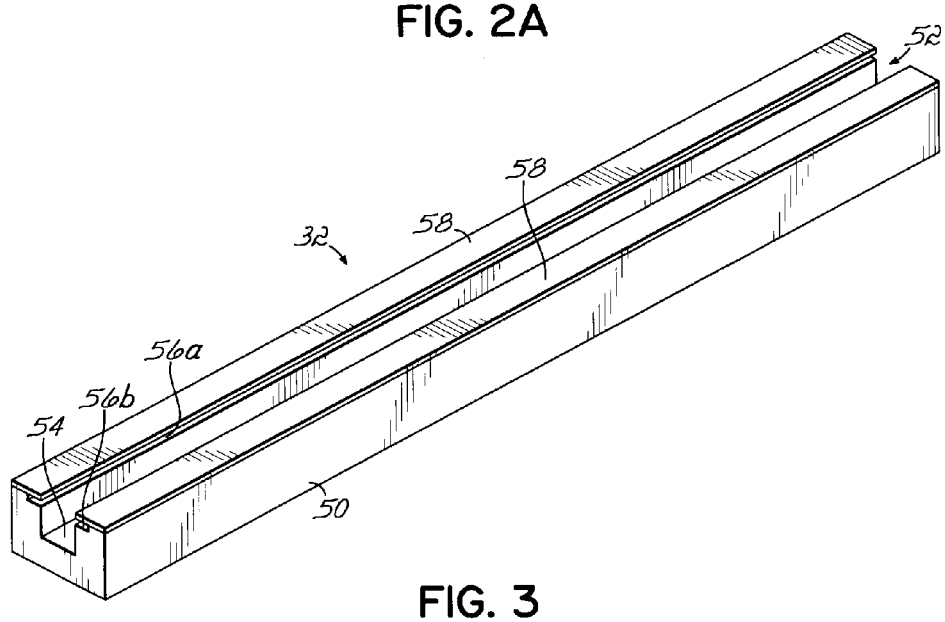
FIGS. 3 and 4 are perspective and end views, respectively, of a channel nest carrier adapted to be mounted on the conveyor of the dispensing system and to receive individual packages of unit dose pharmaceutical products on the channel nest carrier.
Figure 4:
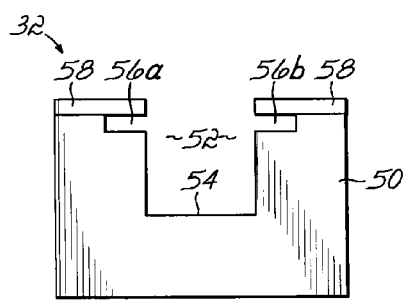

FIGS. 3 and 4 depict an exemplary carrier 32 having an elongate, generally rectangular body 50 having a longitudinal slot or channel 52 formed into one side and extending between the longitudinal ends of the body 50. The channel 52 is shaped complementarily to the shape of the packages 16 and includes a deep central portion 54 and shallower side portions 56a, 56b disposed on opposite sides of the central portion 54, so that a package 16 can be received in the channel 52 with the base portion 18 positioned in the central portion 54 and the sides of the closure 22 supported on the side portions 56a, 56b. The channel 52 is open at both ends to permit unit dose package 16 to be inserted from either end and into the channel 52 during assembly of a particular order. The channel 52 is uniquely shaped to receive unit dose packages 16 containing individual doses of medications/supplements. The side portions 56a, 56b are enclosed at their upper ends, such as by top plates 58 or other structure so that packages 16 received in the channel 52 are constrained for movement only along a longitudinal direction of the channel 52. The carriers 32 are moved along the conveyor path 31 past each of the modules 12, 14 to receive the medications/supplements that make up a particular order. Depending on the number of medications/supplements in a particular order, one or more of the carriers 32 may be assigned to the order. After receiving the unit dose packages 16 from each module 12, 14, the carriers 32 are advanced downstream by the conveyor 30 along the conveyor path 31 to the packaging station 26. In one embodiment, the conveyor 30 is configured to incrementally move the carriers 32 from the upstream end 34 to the downstream end 36 such that a carrier 32 is indexed approximately every 3 seconds.

While the dispensing system 10 shown in FIG. 1 shows a single first module 12 and a single second module 14 located on the same side of the conveyor 30, one of ordinary skill in the art will appreciate that other arrangements for the modules 12, 14 relative to the conveyor 30 are encompassed within the scope of this invention. For example, the dispensing system 10 may include multiple first modules 12 arranged on the same side of the conveyor 30 and/or on opposite sides of the conveyor 30; likewise, multiple second modules 14 can be included with the dispensing system 10 on the same side and/or opposite sides of the conveyor 30. Likewise, in some embodiments of the dispensing system 10, the first or second module 12, 14 may be omitted for certain applications or multiple first or second modules 12, 14 may be included with only a single second or first module 12, 14 as is appropriate for the particular application.

Figure 2:
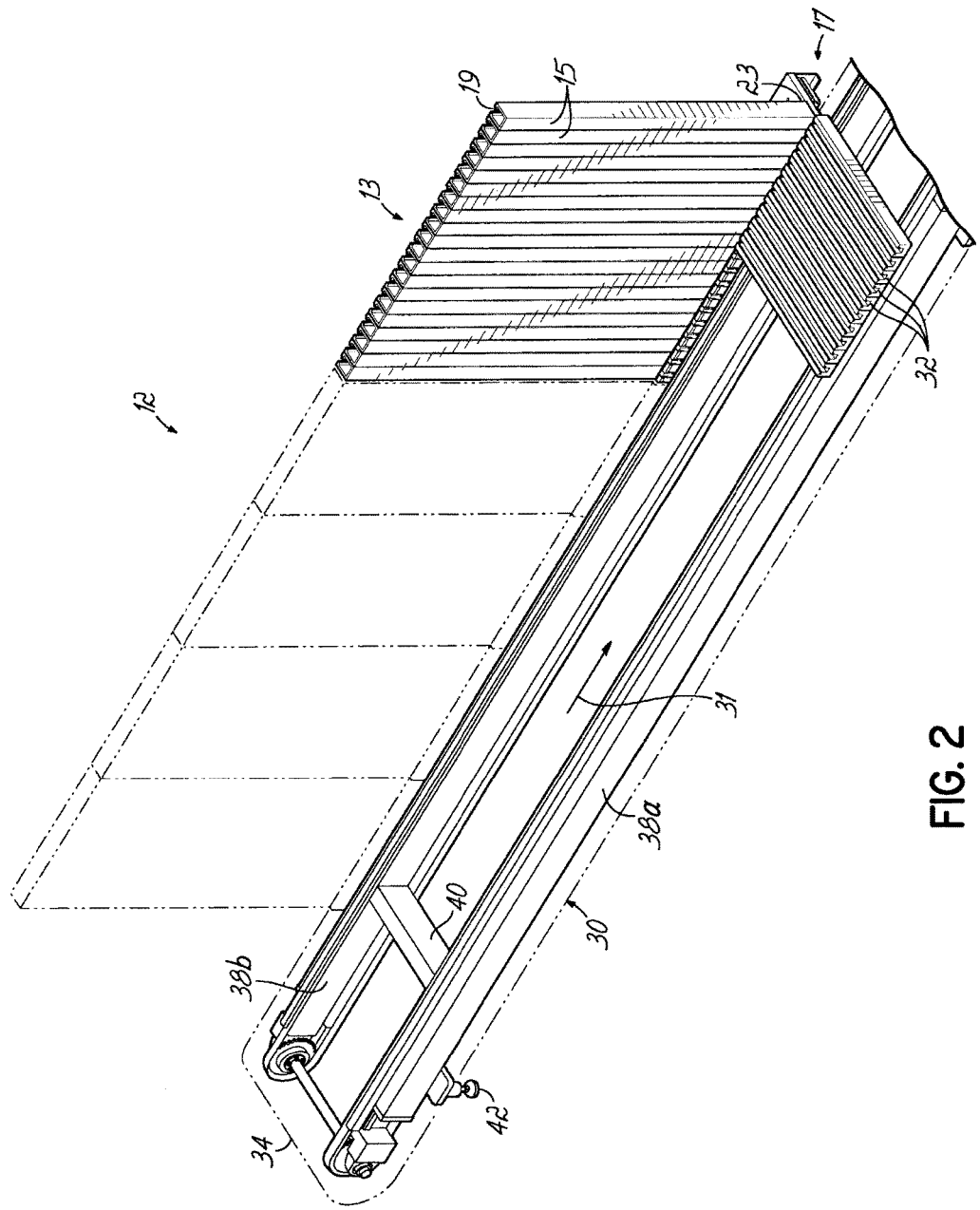
FIG. 2 is a perspective view of a first dispensing module and an adjacent portion of a conveyor of the dispensing system of FIG. 1.
Figure 2A:
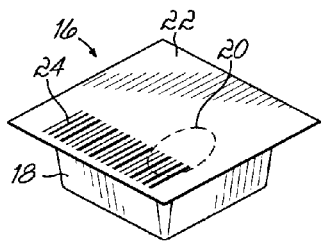
FIG. 2A is a perspective view of one embodiment of an individual unit dose pharmaceutical package containing a single dose of medication or supplement.

As shown in FIGS. 1-2, the first or high-demand module 12 of the dispensing system 10 is located upstream from the second or low-demand module 14 along the conveyor path 31 of the conveyor 30 and travel of the carriers 32. The high-demand module 12 in one embodiment includes two units or banks 13 of storage tubes 15, each positioned on opposite sides of the conveyor 30, although only one unit 13 is shown in FIGS. 1 and 2 for clarity. Each unit 13 of the high-demand module 12 includes a number of vertically oriented storage tubes 15 such that the unit dose packages 16 in each tube 15 are stacked vertically one upon another. The unit dose packages 16 are loaded in storage tubes 15 in a generally vertical stack and similarly oriented with the base portion 18 depending downwardly from the upper planar closure portion 22 of the package 16.

Figure 5:
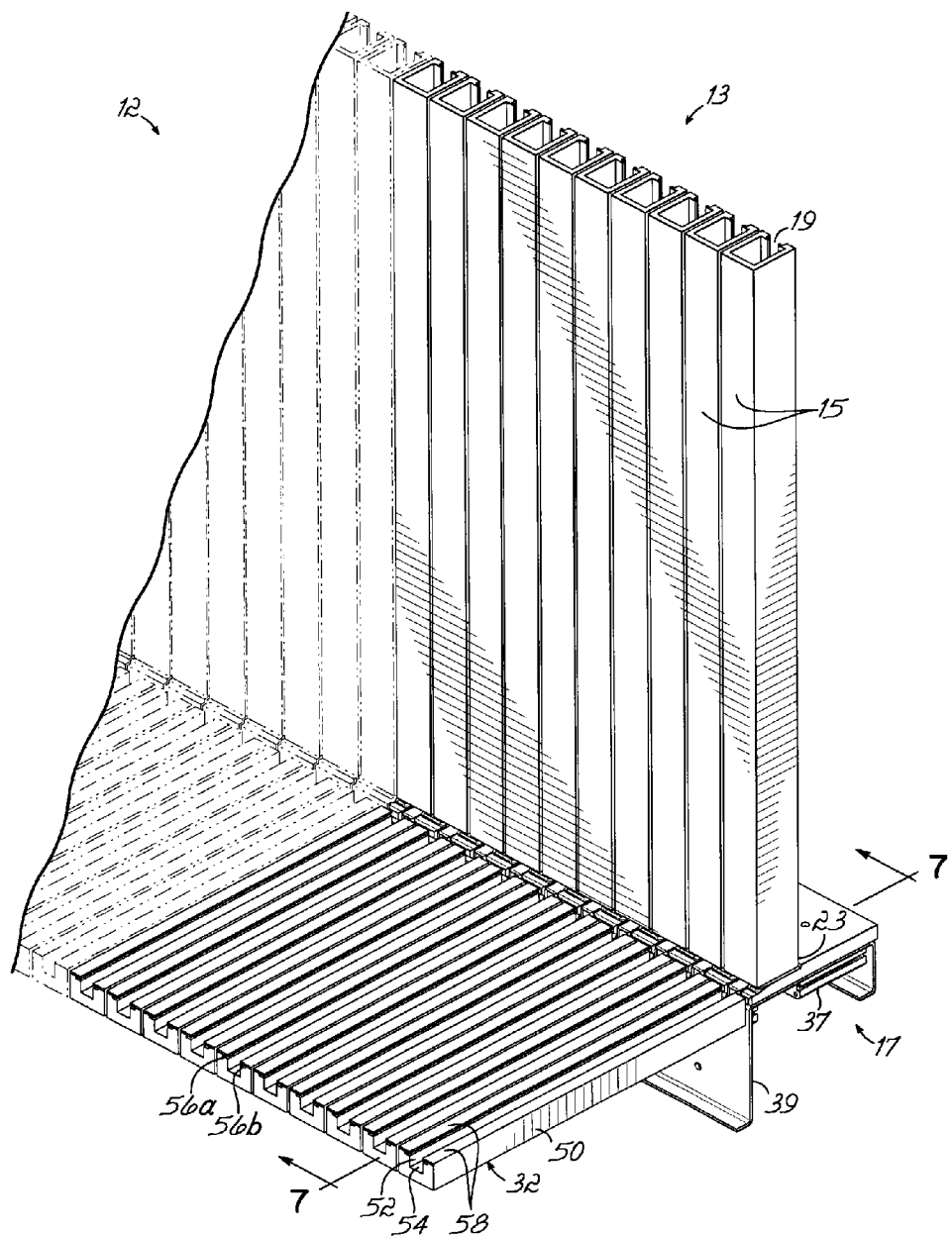
FIG. 5 is a perspective view partially broken away of a bank of storage tubes holding unit dose pharmaceutical packages adjacent channel nest carriers in the first dispensing module of the dispensing system according to one embodiment of this invention.
Figure 6:
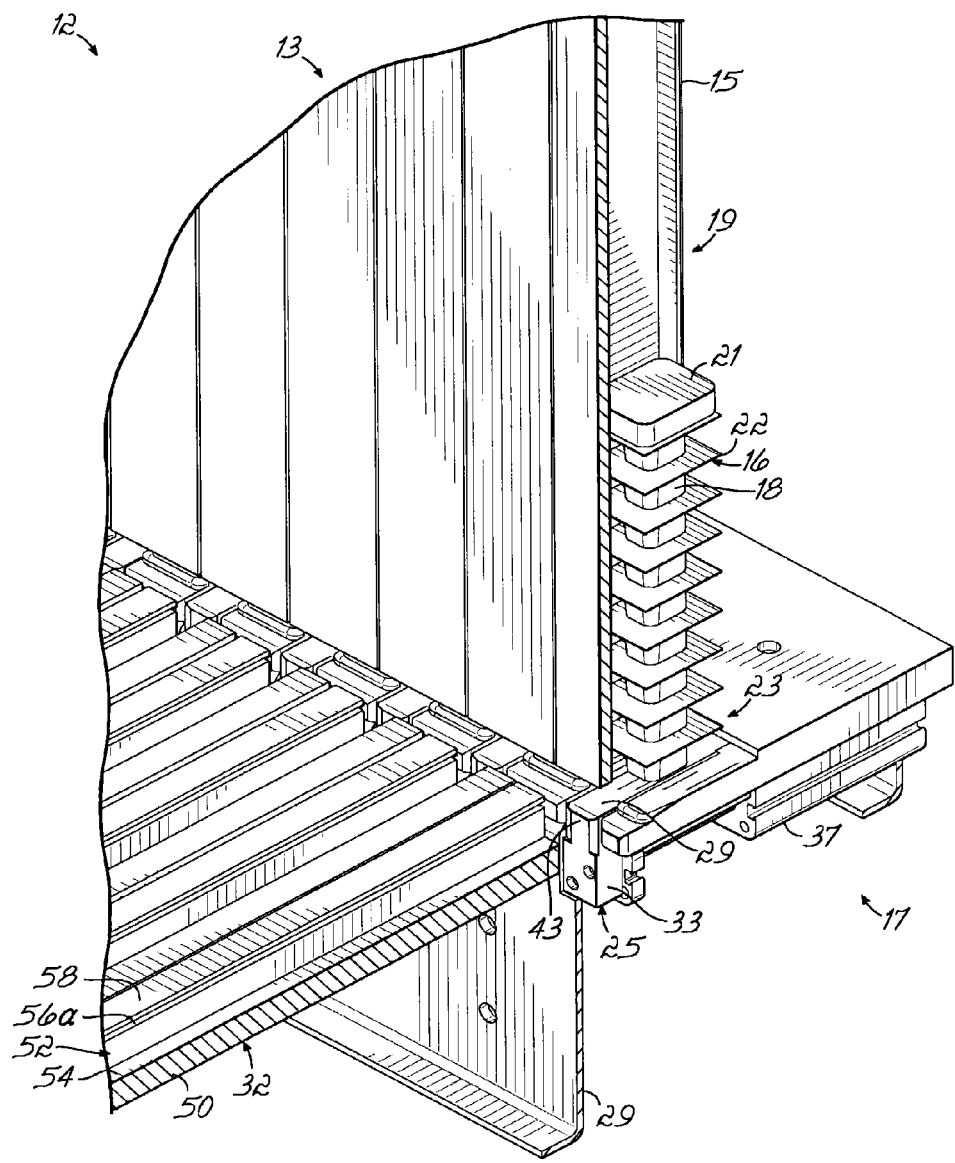
FIG. 6 is an enlarged view similar to FIG. 5 with one of the storage tubes and channel nest carriers partially broken away.

Each storage tube 15 in each of the units 13 of the high-demand module 12 has a generally U-shaped cross-sectional configuration (FIG. 5). The storage tubes 15 are releasably mounted to an insertion plunger mechanism 17 of the high-demand module 12 so that empty or partially empty tubes 15 may be removed and replaced on the high-demand module 12 with filled tubes 15. Alternatively, the tubes 15 in the high-demand module 12 can be refilled from a portable storage tube (not shown) through the open upper end of the tube 15 without removal of the tube 15 from the module 12. An open longitudinal slot 19 of each storage tube 15 is oriented outwardly and away from the conveyor 30 when the storage tube 15 is mounted on the high-demand module 12. As shown in FIG. 6, a weight 21 is at the top of each stack of unit dose packages 16 housed in a storage tube 15 to partially compress the stack and force it downward toward a bottom dispensing end 23 of the vertically oriented storage tube 15.

Figure 7:
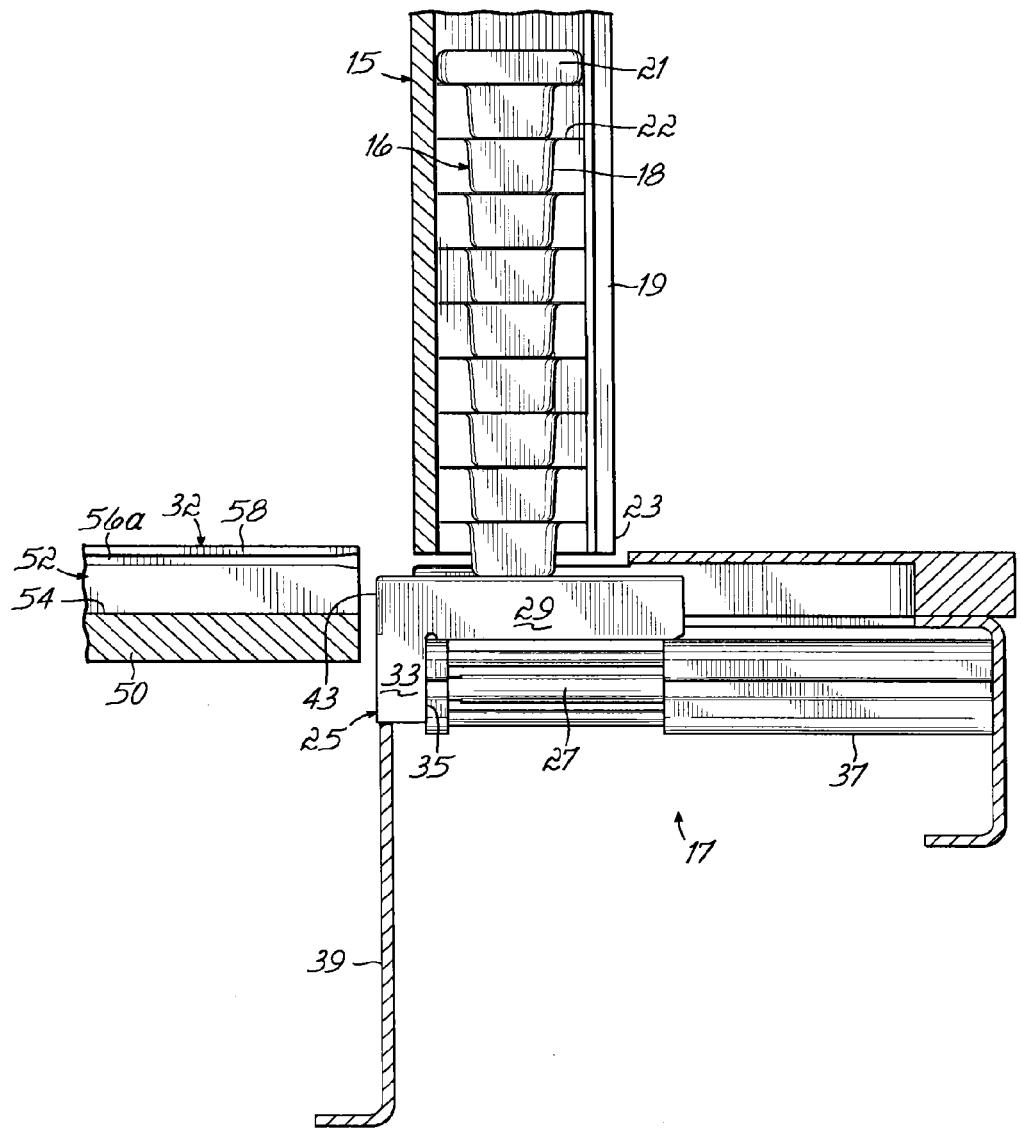
FIGS. 7-9 are cross-sectional side-elevational views of the operation of an insertion plunger mechanism inserting individual unit dose pharmaceutical packages from the storage tubes of the first dispensing module into the channel nest carriers on the conveyor according to one embodiment of this invention.
Figure 8:
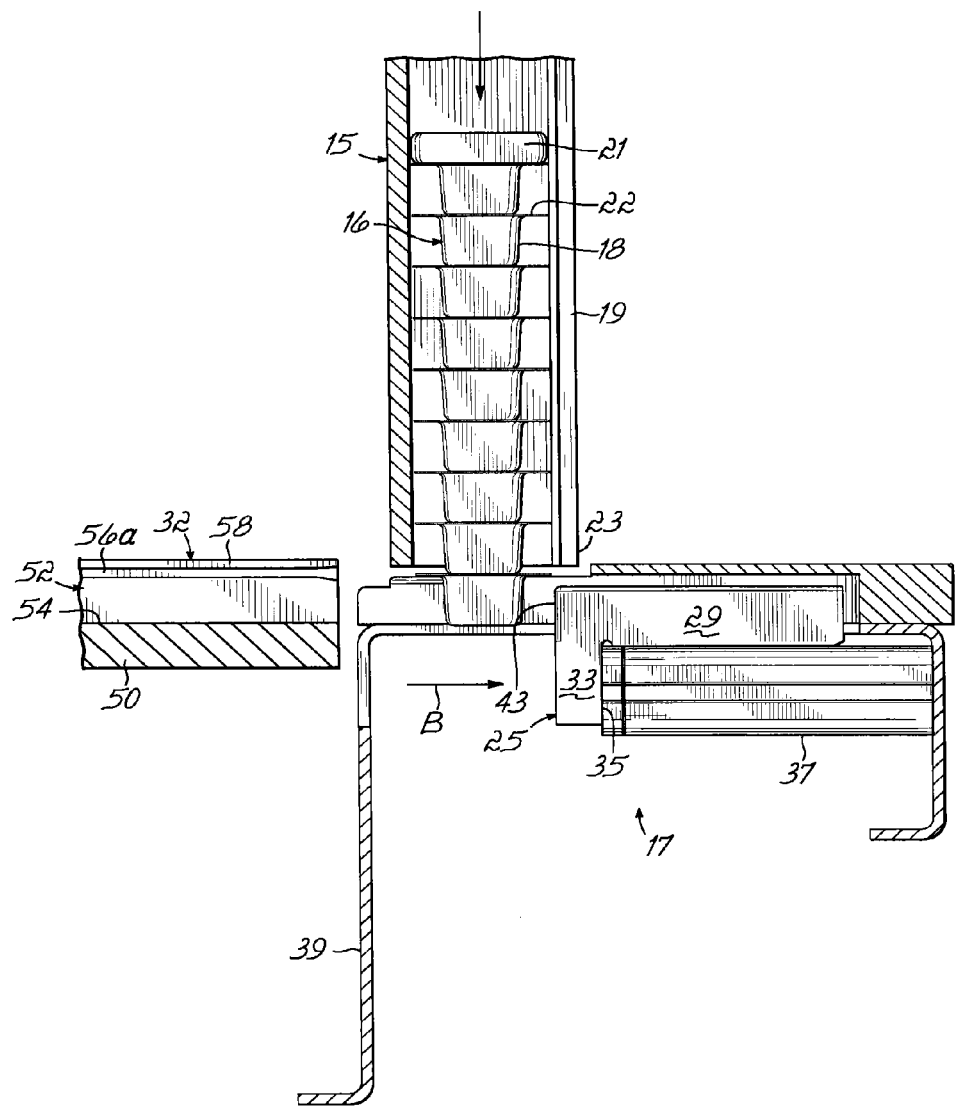
Figure 9:
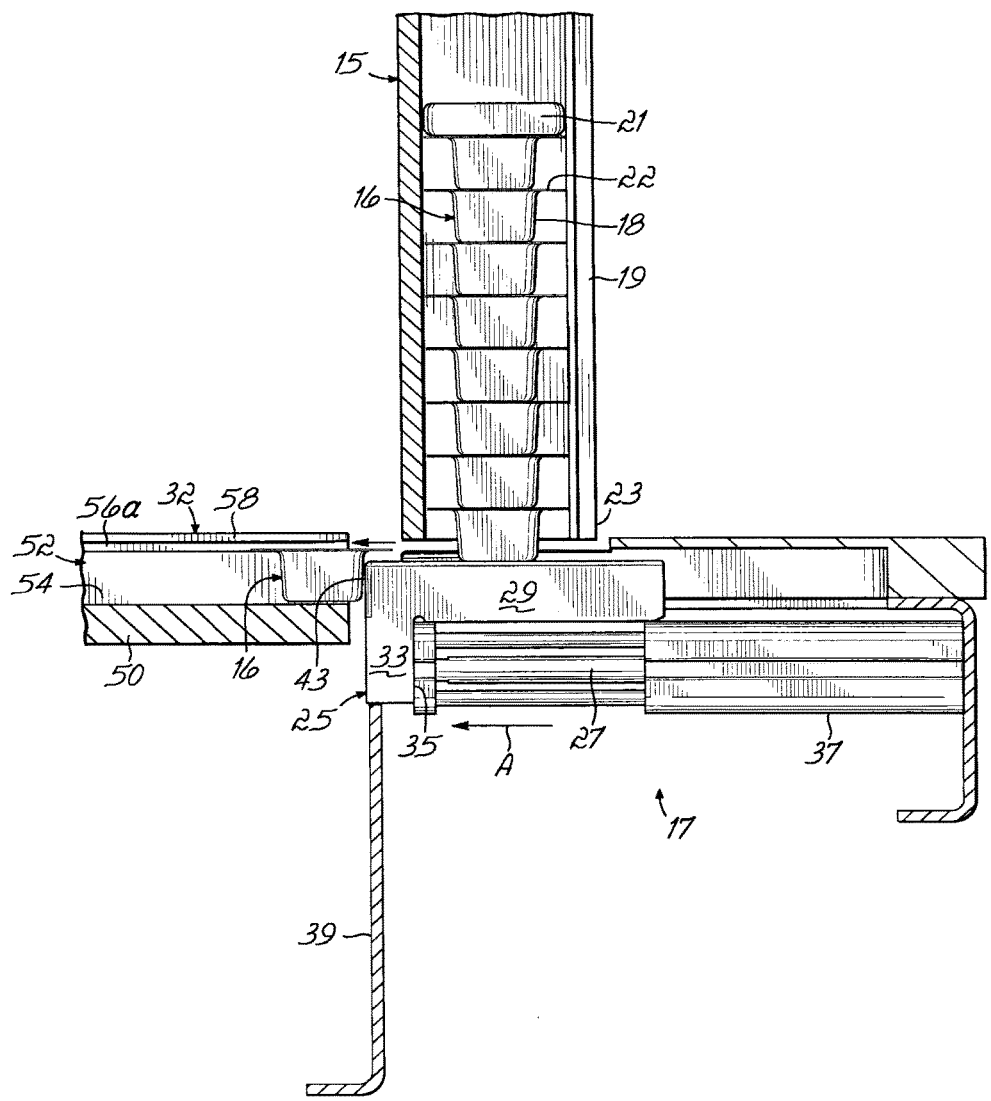

Referring to FIGS. 6-9, each storage tube 15 mounted in the high-demand module 12 has an insertion plunger mechanism 17 associated with it and positioned adjacent the bottom dispensing end 23 of the storage tube 15. The insertion plunger mechanism 17 has a support housing 39 and a generally L-shaped plunger 25 mounted to a pneumatically actuated rod 27 which reciprocates toward and away from the conveyor 30 in a direction generally parallel with the orientation of the carriers 32 on the conveyor 30. The rod 27 is coupled to a pneumatic actuator 37. A longer leg 29 of the plunger 25 is oriented generally horizontally and is also aligned with the carriers 32 on the conveyor 30. A leading upper edge 43 of the plunger 25 is at the juncture between the long leg 29 and a short leg 33 of the plunger 25 with the short leg 33 depending vertically downward from the upper long leg 29. An interior face 35 of the shorter leg 33 is connected to the reciprocating rod 27 of the insertion plunger mechanism 17. The extended, rest position of the plunger 25 effectively seals the end of the carriers 32 of the conveyor 30 and the dispensing end 23 of the tube 15 to inhibit loss of unit dose packages 16 (FIG. 7).

As the respective carriers 32 advance on the conveyor 30, they are sequentially aligned with the individual storage tubes 15 in the high-demand module 12. Each of the storage tubes 15 in the high-demand module 12 includes similar medications/supplements 20 and more than one storage tube 15 in the high-demand module 12 may include unit dose packages 16 filled with the same medication/supplement 20 as another storage tube 15 in the high-demand module 12 so as to provide increased capacity for more frequently prescribed medications/supplements 20. When an identified carrier 32 is aligned with a storage tube 15 in the high-demand module that houses a unit dose package 16 containing a medication/supplement 20 to be included in the specified order, the rod 27 retracts in the direction of arrow A in FIG. 8 such that the upper edge 43 of the L-shaped plunger 25 is positioned on an outboard side of the downwardly depending base portion 18 of the lowermost unit dose package 16 in the storage tube 15. The rod 27 then extends in the direction of arrow B in FIG. 9 from the housing of the insertion plunger mechanism 17 thereby pushing the plunger 25 toward the conveyor 30 and carrier 32. The plunger 25 likewise pushes the lowermost unit dose package 16 from the storage tube 15 toward and into the aligned carrier 32 on the conveyor 30. Each carrier 32 is generally U-shaped and has the channel 52 to receive the opposed edges of the upper planar closure portion 22 of the unit dose package 16. As the unit dose package 16 is inserted into the carrier 32, the plunger 25 remains resident below the storage tube 15 and the upper, longer leg 29 of the plunger 25 retains the now lowest unit dose package 16 in the tube 15 until such time as that unit dose package 16 is to be dispensed from the storage tube 15 and into an appropriate carrier 32 on the conveyor 30.

The plunger 25 can be actuated multiple times per conveyor index. This capability, combined with the use of opposing units 13 of storage tubes 15 on opposite sides of the conveyor 30 in the high-demand module 12, allow for the opposite sides of each carrier 32 to be filled simultaneously with unit dose packages 16 from the appropriate storage tubes 15 thereby increasing the throughput of the high-demand module 12.

The low-demand module 14 is downstream from the high-demand module 12 (FIG. 1) and includes two banks or units 66 of medication/supplement storage tubes 74, one unit 66 positioned on each lateral side of the conveyor 30 although the units 66 on only one side of the conveyor 30 are shown in FIG. 1 for clarity. As is the case with the high-demand module 12, the units 66 may feed unit dose packages 16 to the opposite ends of the carriers 32, although this is not accomplished simultaneously from the opposite ends of the carriers to inhibit the unit dose packages 16 from being pushed to the opposing unit 66.

When the carriers 32 on the conveyor 30 that are assigned to a particular order are aligned with slots on a transfer station 64 adjacent the conveyor 30 in the low-demand module 14 that contain the packages 16 for that particular order, the medications/supplements 20 are pushed into the assigned carrier 32. The assigned carrier 32 may already have unit dose packages 16 therein from the upstream high-demand module 12.

The conveyor 30 thereafter carries the carriers 32 to the packaging station 26 for final packaging and assembly of the patient orders. During movement of the packages 16, the carriers 32, transfer nests, and transfer stations are each configured to maintain positive control of the medications/supplements 20 such that no medication/supplement 20 is allowed to "free fall" during the dispensing process.

Figure 10:
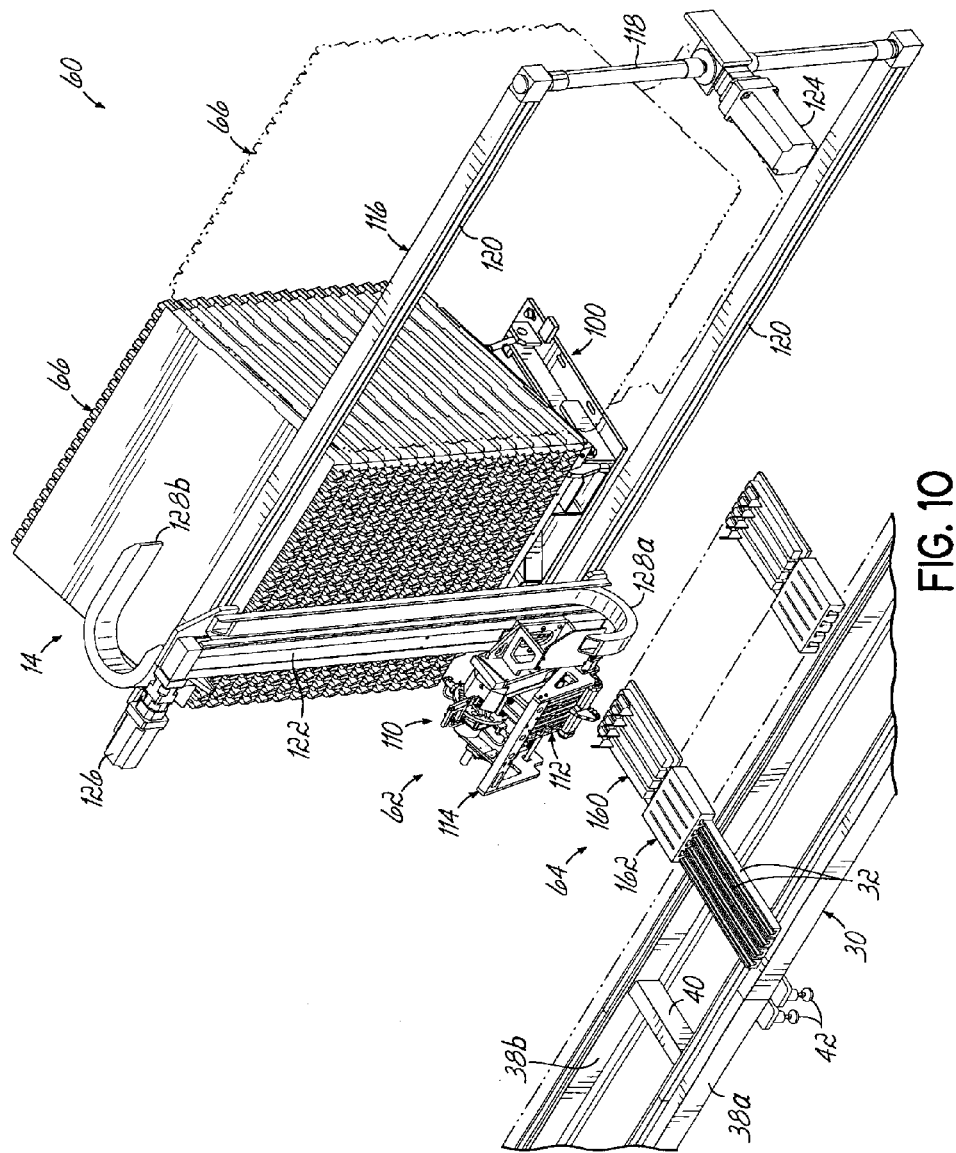
FIG. 10 is a perspective view of one embodiment of a second dispensing module of the dispensing system of FIG. 1 according to one embodiment of this invention.

Referring now to FIG. 10, the low-demand module 14 includes a storage module 60 for storing the individually packaged and labeled medications/supplements, a pick device 62 for retrieving selected medications/supplements from the storage module 60, and a transfer station 64 for delivering the selected medications/supplements to the carriers 32 of the conveyor 30 to fill orders. The storage module 60 has one or more storage units 66 positioned alongside the conveyor 30, as may be desired, to accommodate storage of the medications/supplements needed to fill the medical orders. With continued reference to FIG. 10, and referring further to FIGS. 11-13, each storage unit 66 has a plurality of generally rectangular, vertically-spaced plates 68 and a plurality of laterally spaced walls 70 disposed between each plate 68 to define an array of elongate bins 72 configured to receive storage modules or tubes 74 containing stacked packages 16 of the individually packaged medications/supplements.

The storage tubes 74 are slidably received in the respective bins 72 at first, receiving ends 76 of the bins 72. In the embodiment shown, the plates 68 and walls 70 of the storage unit 66 are formed from aluminum sheet material. The walls 70 are formed with notches 78 and tabs 80, and the plates 68 are formed with corresponding slots (not shown) whereby the walls 70 and plates 68 may be assembled together to form the array of bins 72. In the embodiment shown, the bins 72 have a generally rectangular cross-sectional shape, as do the storage tubes 74 that are received within the respective bins 72. In this embodiment, the tubes 74 are formed from extruded plastic material and an end cap 82 disposed at one end of the tube 74 facilitates dispensing the packages 16 there from.

Figure 13:
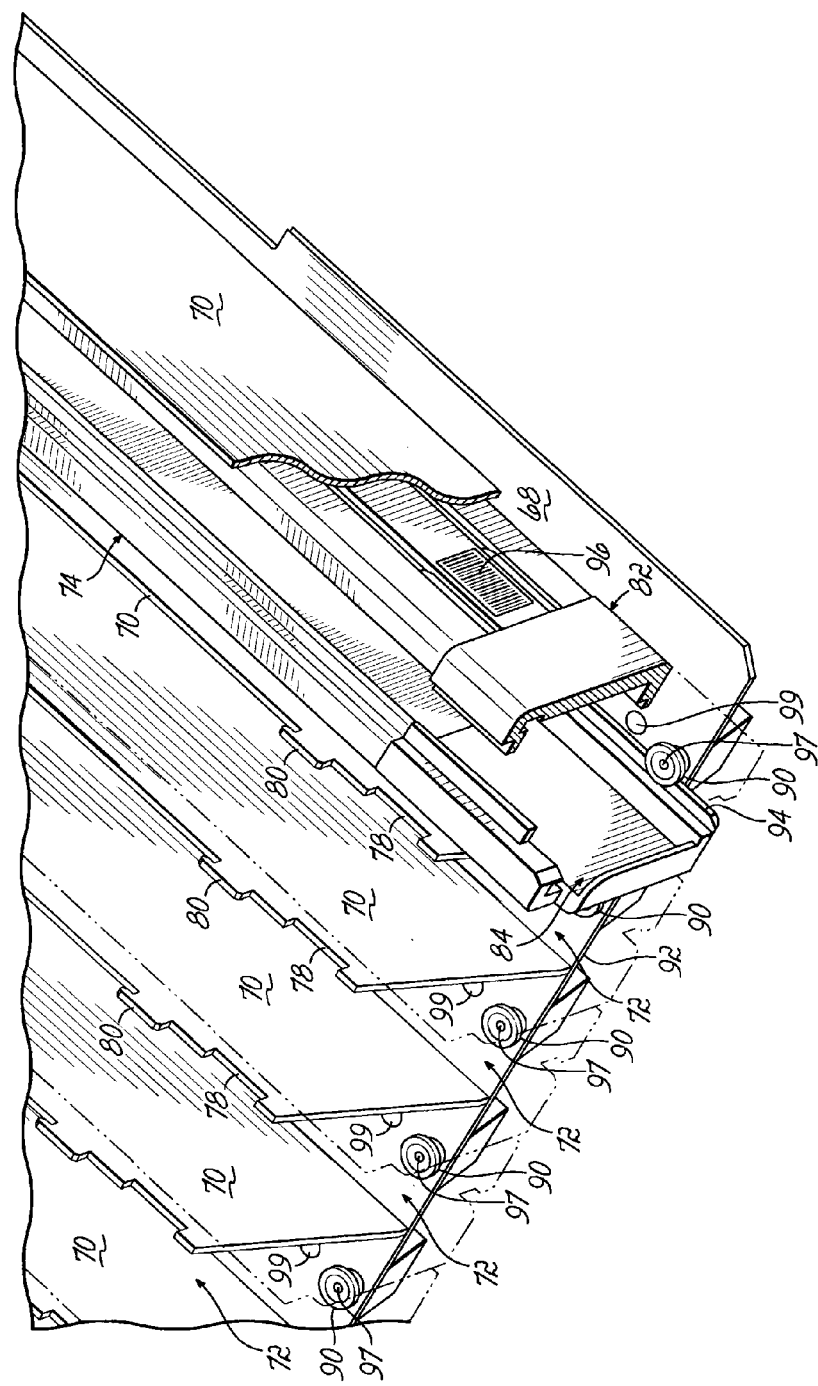
FIG. 13 is an enlarged perspective view of a portion of the row of FIG. 12 with the storage tube retained therein.

As shown in FIG. 13, the end cap 82 includes a slot 84 along an upwardly facing side of the storage tube 74 whereby an individual unit dose package 16 may be moved in a direction transverse to the longitudinal axis of the storage tube 74 for removal of the package 16 from the storage tube 74 through the slot 84. With continued reference to FIG. 13, each bin 72 is provided with a registration pin 90 proximate a second, dispensing end 92 that faces the pick device 62. As the storage tubes 74 are placed within the respective bins 72, the registration pins 90 engage another slot 94 formed on the end cap 82 to position the end cap 82 at a location that facilitates engagement and retrieval of the individual unit dose package 16 stored in the tube 74 by the pick device 62, as will be described in more detail below.

Figure 11:
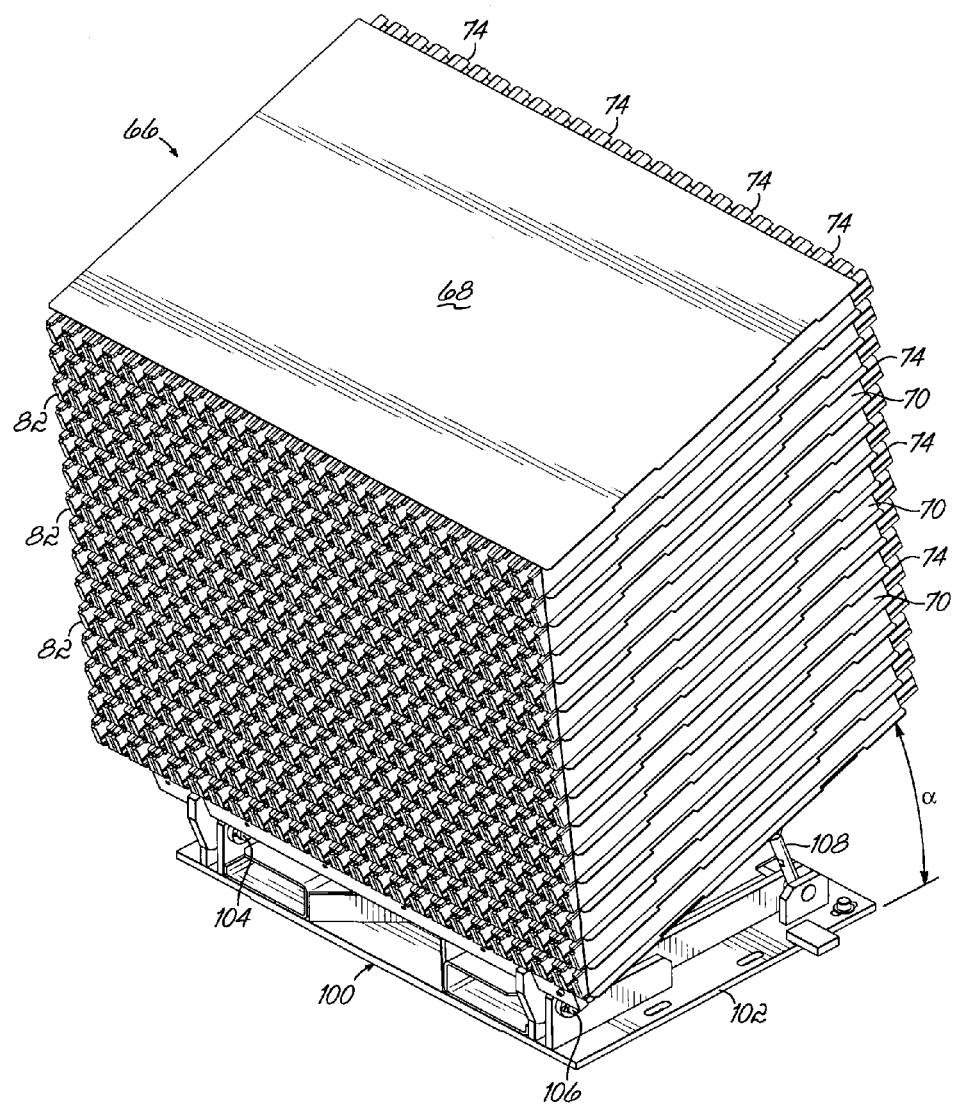
FIG. 11 is a perspective view of a bank of storage tubes containing unit dose pharmaceutical packages in the second dispensing module of the dispensing system shown in FIG. 10.
Figure 12:
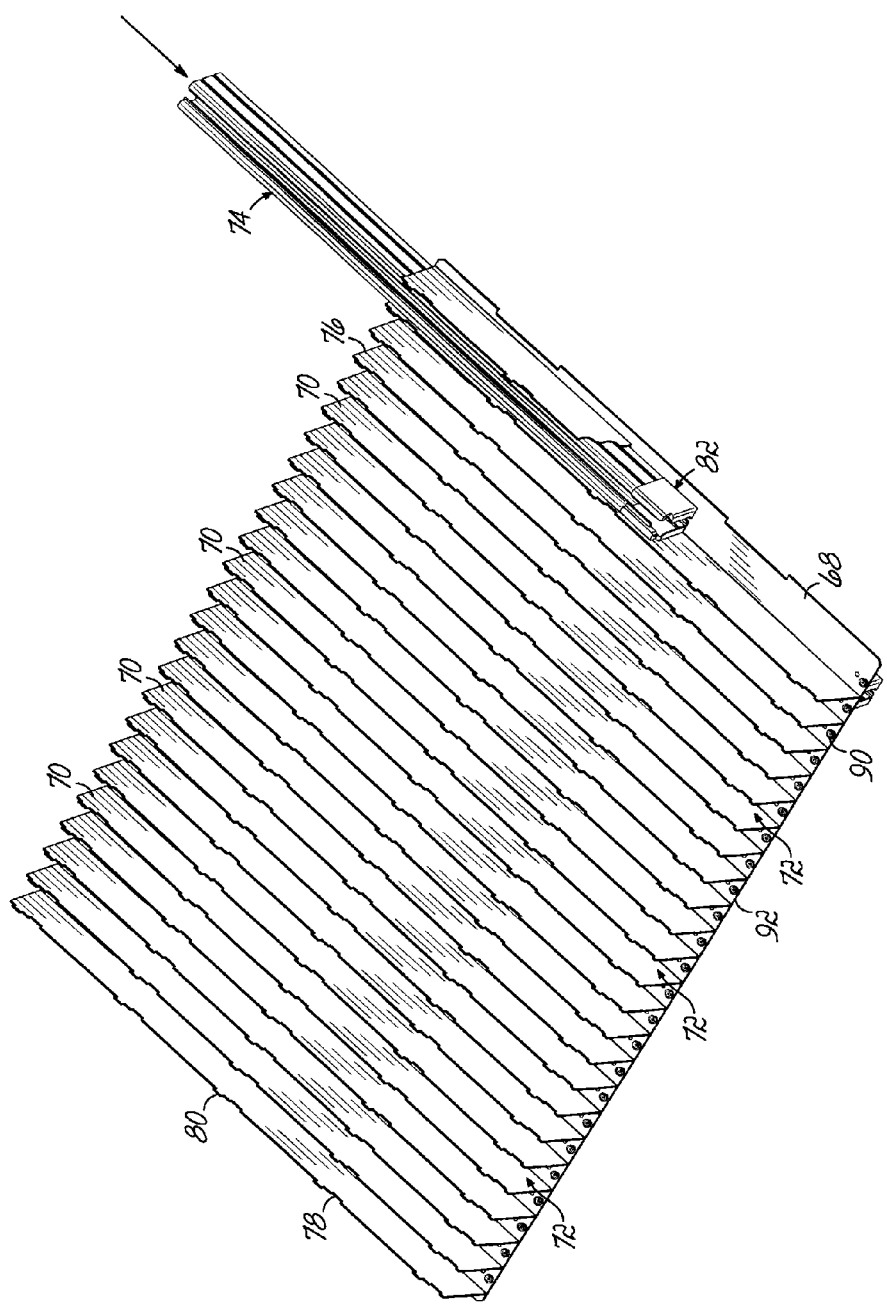
FIG. 12 is a perspective view of one row of the bank of FIG. 11 with a storage tube being inserted therein.

As depicted in FIG. 11, each storage unit 66 is supported on a base 100 so that storage tubes 74 supported in the bins 72 of the storage unit 66 may be positioned for proper access by the pick device 62. The base 100 includes a generally flat plate 102 that may be bolted or otherwise secured to the floor surface. The array of bins 72 may be pivotally coupled to the plate 102 by appropriate pin connections 104, 106, and may be adjusted to have a desired inclination angle relative to the floor surface by an adjustable link 108 coupled between the array of bins 72 and the plate 102. The inclined orientation of the bins 72 of the storage unit 66 places the dispensing ends 92 of the bins 72 at a lower elevation than the receiving ends 76. The packages 16 of medications/supplements 20 are stacked one atop another within the storage tubes 74, and the storage tubes 74 are slidably received within the respective bins 72 of the storage unit 66. The storage tubes 74 are inserted with the end caps 82 positioned at the dispensing ends 92 of the bins 72 such that the stacked packages 16 within the tubes 74 are urged by gravity in a direction toward the end caps 82 at the dispensing ends 92 of the bins 72. A weight (not shown) may be provided on top of the uppermost package 16 within each storage tube 74 to facilitate movement of the packages 16 toward the end caps 82.

Figure 16A:
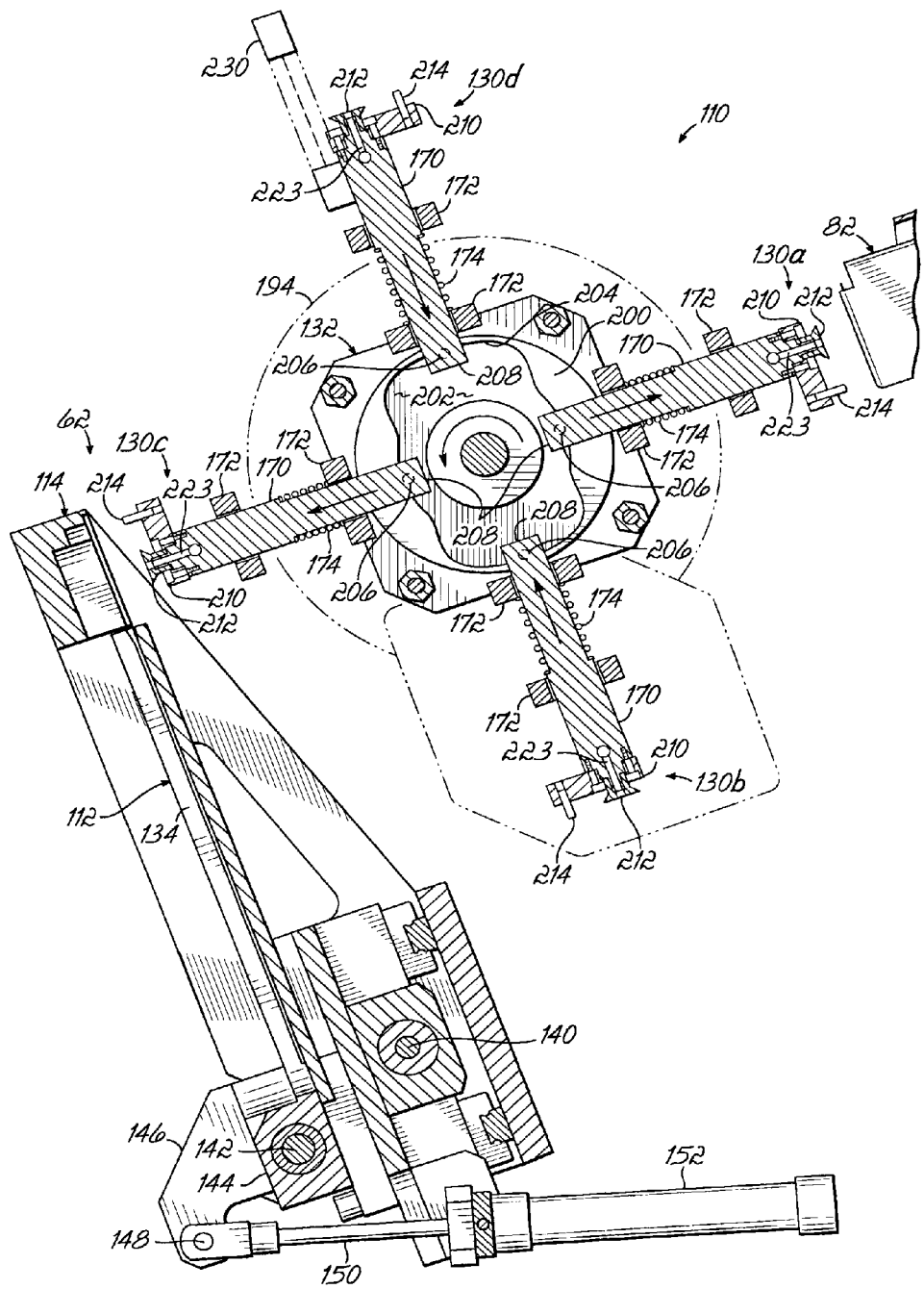
FIG. 16A is a cross-sectional side-elevational view of the pick device and an associated transfer mechanism of the second dispensing module taken along line 16A-16A of FIG. 15.
Figure 16B:
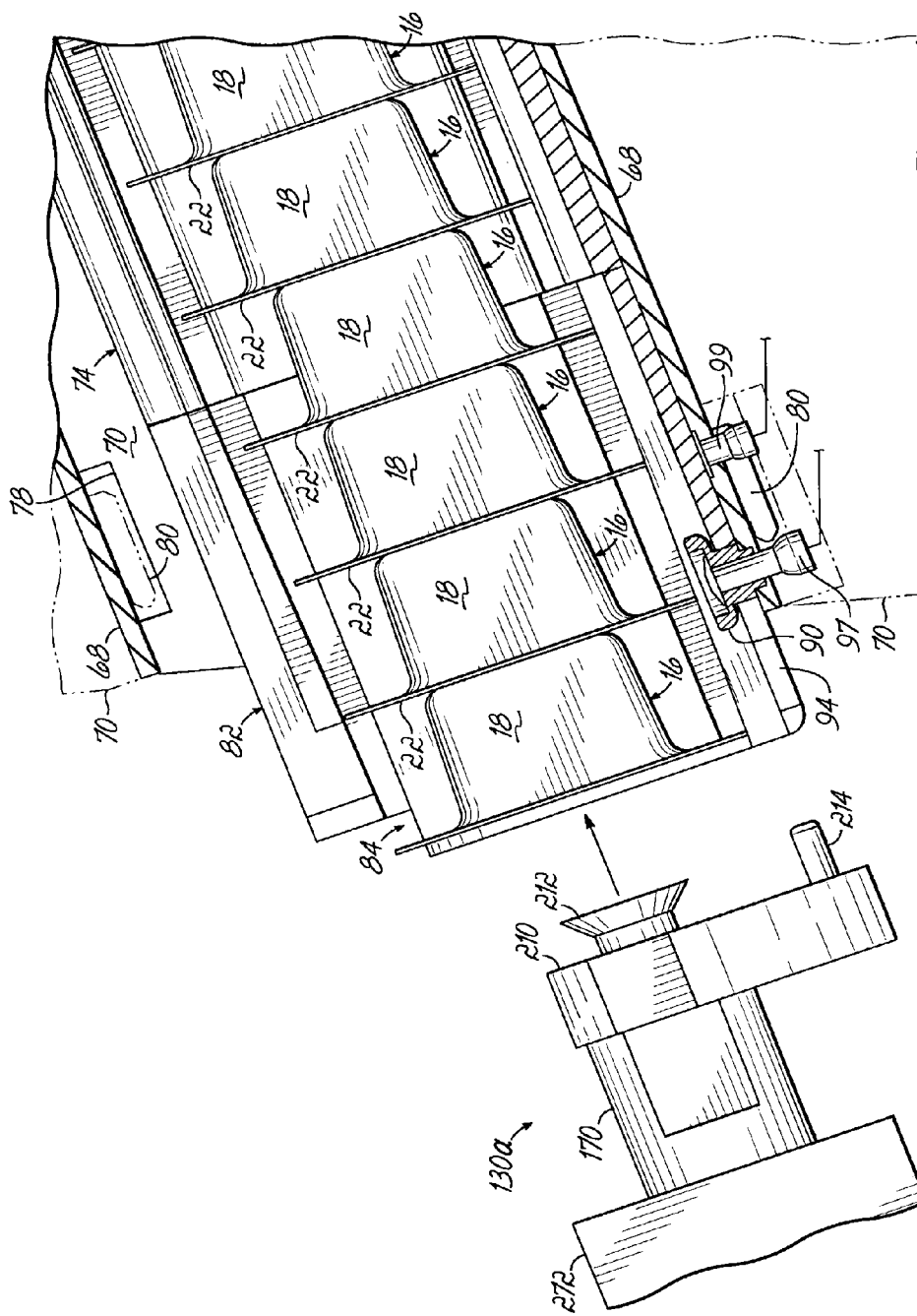
FIG. 16B is an enlarged cross-sectional view of a gripper on the pick device engaging a unit dose pharmaceutical package in a storage tube on the second dispensing module.
Figure 18A:
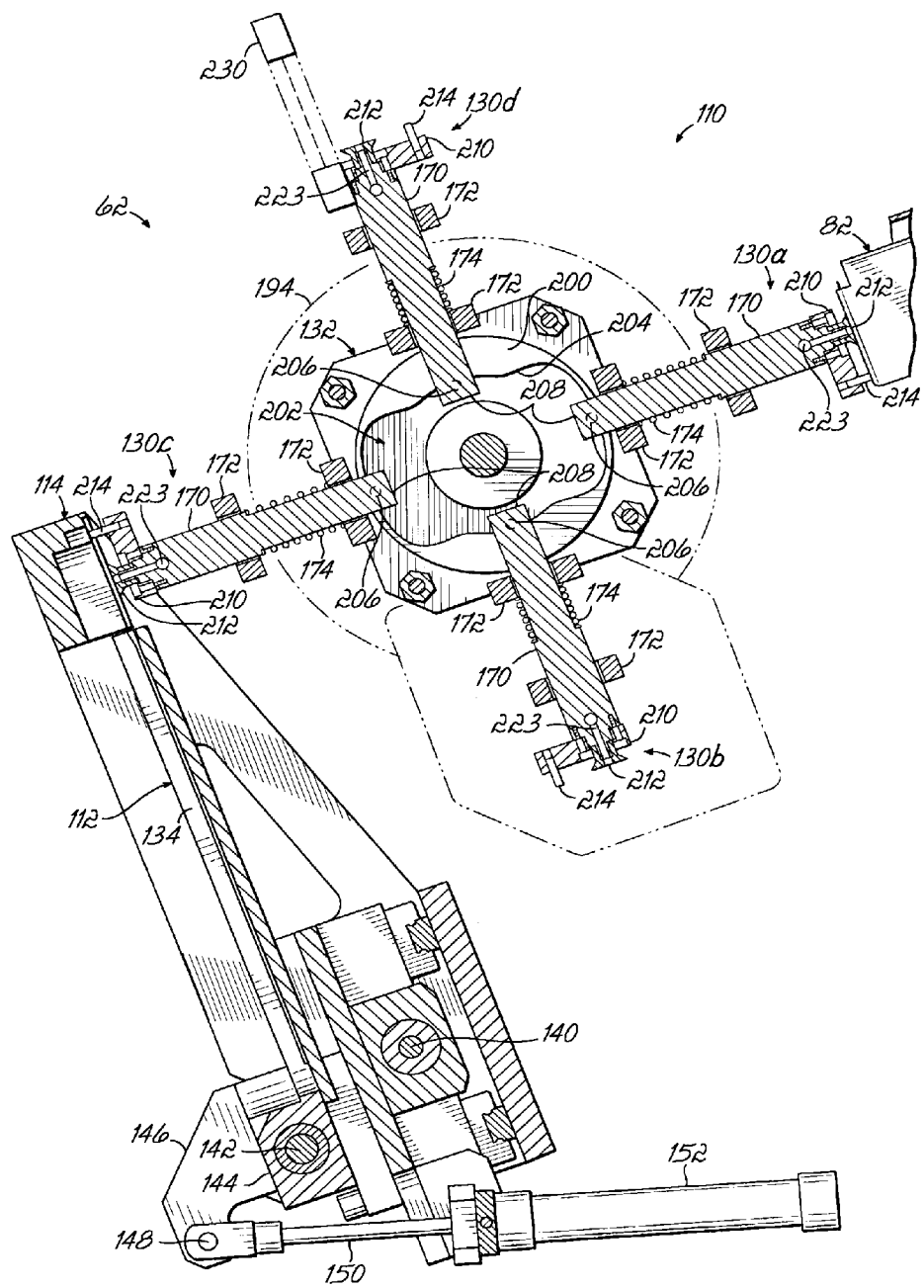
FIGS. 18A-18D, 19A-19C, 20A-20C and 21 are sequential cross-sectional views of the pick device operation of the second dispensing demand module retrieving a unit dose pharmaceutical package from the bank and transferring it to a transfer mechanism according to one embodiment of this invention.
Figure 18B:
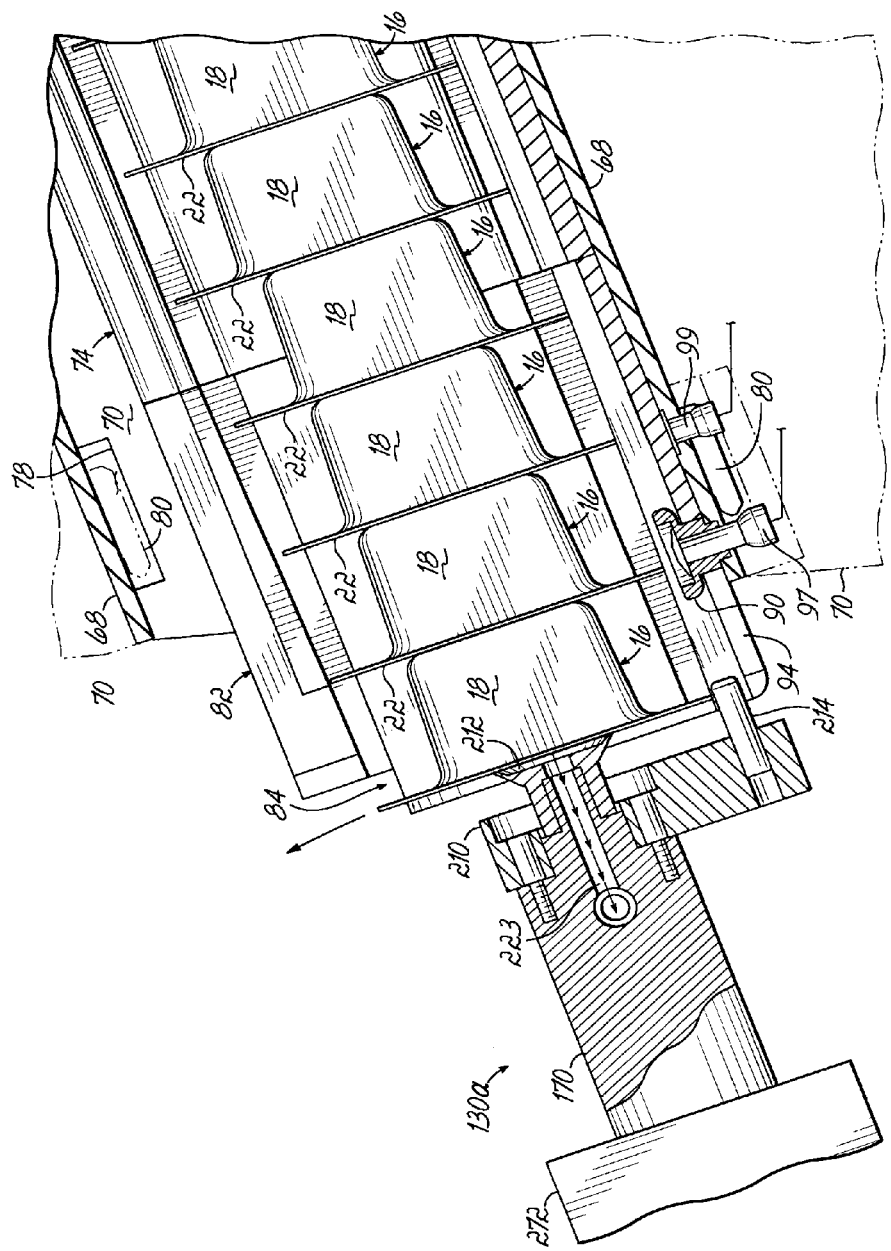
Figure 18C:
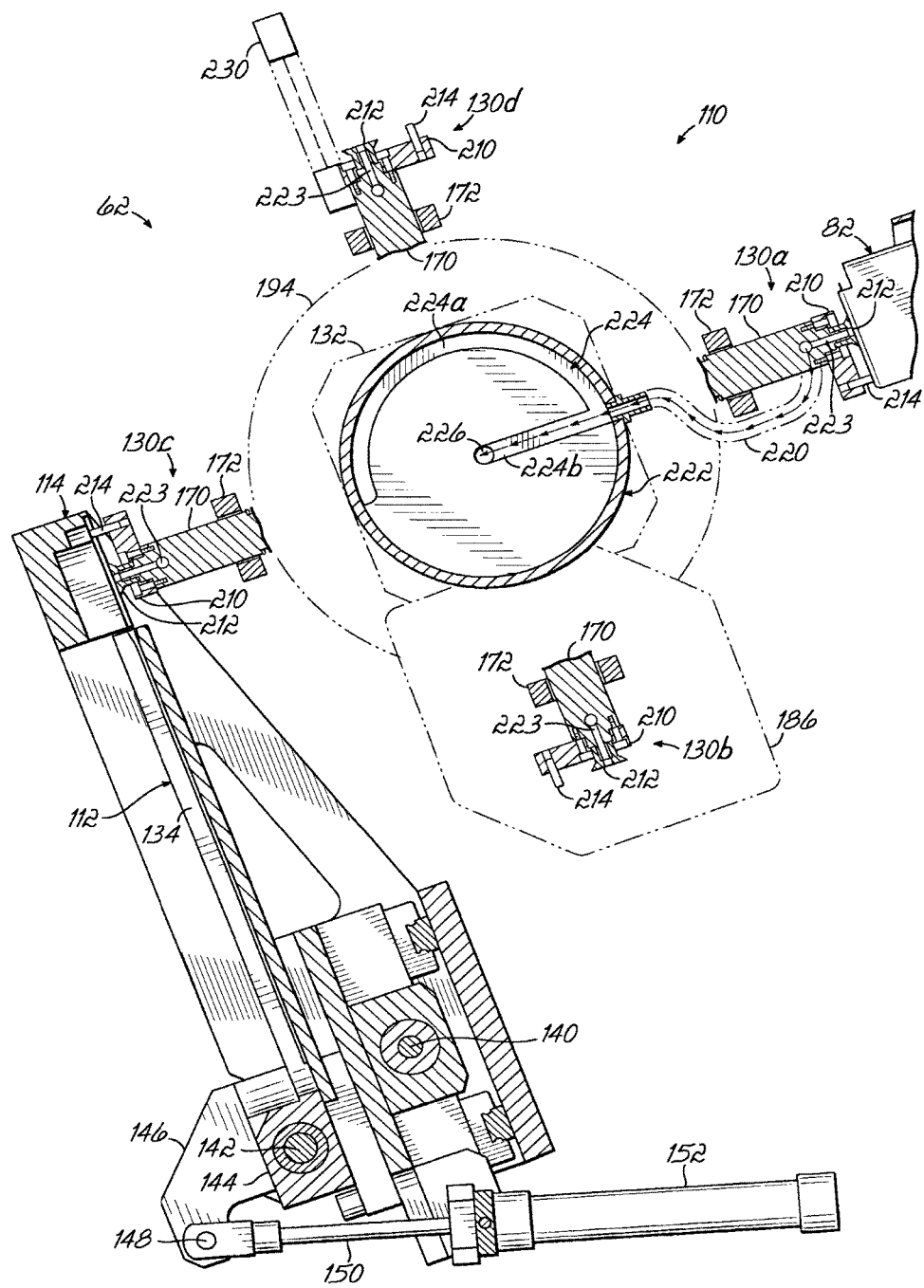

As depicted in FIG. 16B, each bin 72 may be provided with a sensor 97 proximate the dispensing end 92 for detecting the presence of packages 16 within the storage tube 74 supported in the bin 72, and for communicating with a control 240 to indicate when the storage tube 74 needs to be replaced with a storage tube 74 filled with packages 16. The bins 72 may also be provided with one or more sensors 99 for detecting the presence of a storage tube 74 in the bin, and for communicating with the control 240 when a storage tube 74 is not in the bin 72. In the embodiment shown, in FIGS. 16B and 18B, sensors 97 for detecting the presence of packages 16 in a storage tube 74 are located with the registration pin 90. Each storage tube 74 contains only a single type of medication/supplement 20, and the storage tubes 74 may be provided with information 96 identifying the particular type of medication/supplement contained within the packages 16 stacked within the tube 74 (FIG. 13). In one embodiment, the information provided on the storage tubes 74 includes machine readable information, such as bar codes, RFID, or other types of machine readable information, to facilitate the automated storage, tracking and dispensing of the medications/supplements.

Figure 14:
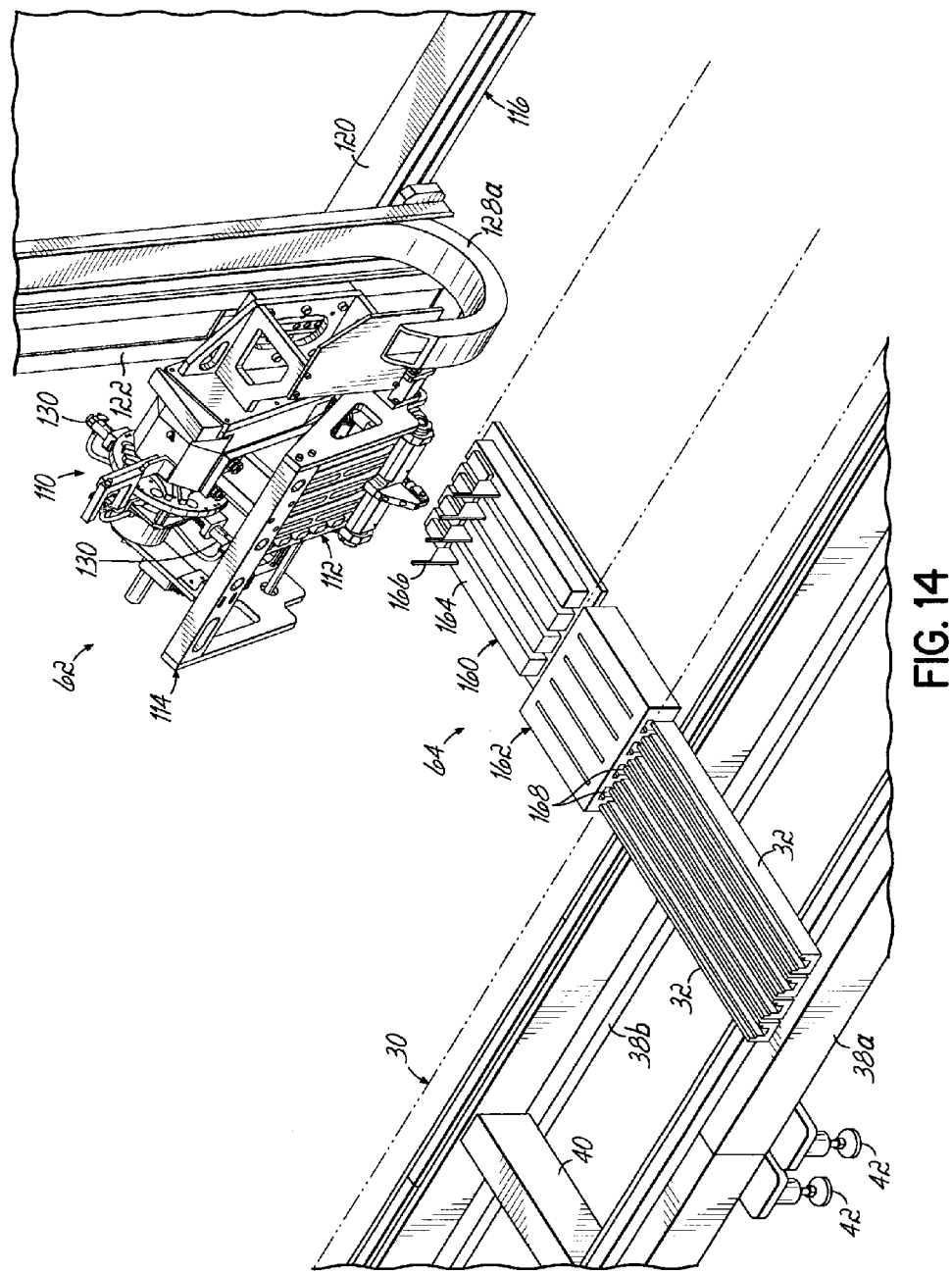
FIG. 14 is a perspective view depicting a pick device and transfer station of the second dispensing module.

The medications/supplements 20 stored in the array of bins 72 of the storage units 66 of the storage module 60 are retrieved by the pick device 62 and are delivered to a transfer station 64 for subsequent transfer to a designated carrier 32 as the carrier 32 moves past the transfer station 64 on the conveyor 30, as will be described in more detail below. With reference to FIGS. 10 and 14, the pick device 62 includes a pick head 110 and a transfer nest 112 supported on a transfer frame 114 that moves with the pick head 110. The pick device 62 is supported on a vertically inclined gantry 116 having vertical frame members 118 and horizontal frame members 120 positioned proximate the dispensing ends 92 of the bins 72 of the storage module 60 for access to the storage tubes 74. A gantry cross member 122 is driven by a first motor 124 for movement longitudinally along the horizontal frame members 120, and a second drive motor 126 moves the pick device 62 vertically along the gantry cross member 122 so that the pick head 110 can access any of the plurality of storage tubes 74 housed in the storage module 60. Flexible cable guides 128a, 128b may be provided adjacent the gantry cross member 122 and/or the horizontal frame members 120 to house cables or wires extending between the pick device 62 and corresponding power supplies and/or control modules.

As shown in FIGS. 15 and 16A, the pick head 110 includes a plurality of grippers 130 extending from a rotatable housing 132 for engaging and retrieving selected packages 16 from the storage tubes 74 supported in the storage module 60. Four grippers 130a, 130b, 130c, 130d are depicted and are collectively referred to as "grippers 130" herein. The transfer nest 112 is supported within a transfer frame 114 coupled to the pick head 110 for movement therewith, such that packages 16 selected by the pick head 110 may be received onto the transfer nest 112 and subsequently delivered to the transfer station 64. In the embodiment shown, the transfer nest 112 includes four slots 134 for receiving the packages 16 of medications/supplements from the grippers 130 of the pick head 110. It will be appreciated, however, that the transfer nest 112 may alternatively have a fewer number or a greater number of slots 134, as may be desired. The slots 134 of the transfer nest 112 are configured to receive the packages 16 from the grippers 130 of the pick head 110 and to maintain positive control over the motion of the packages 16 as they are moved to the transfer station 64. To this end, the slots 134 are shaped complementarily to the shape of the packages 16, in a manner similar to the channels 52 of carriers 32 and as depicted in FIG. 15A.

The transfer nest 112 is movable along a shaft 140 in a longitudinal direction relative to the pick head no so that the selected packages 16 of medications/supplements may be received in one of the plurality of slots 134 on the transfer nest 112 by aligning a selected slot 134 in registration to receive a package 16 from the grippers 130 of the pick head no. The transfer nest 112 is also pivotable about a shaft 142 coupled to the transfer frame 114 to position the transfer nest 112 adjacent the transfer station 64 for delivery of the selected packages 16 of medications/supplements to the transfer station 64. In the embodiment shown, the transfer nest 112 is pivotally coupled to the transfer frame 114 by a shaft 142 received in shaft supports 144 extending from the transfer frame 114. A bracket 146 extending from the transfer nest 112 is coupled at a pivot joint 148 to the end of a drive rod 150 of a pneumatic piston 152, whereby the transfer nest 112 can be pivoted around the shaft 142 by actuation of the pneumatic piston 152, from a first position wherein the transfer nest 112 is located adjacent the pick head 110 for receiving the selected packages 16 of medications/supplements (depicted in FIGS. 14 and 15), to a second position wherein the transfer nest 112 is positioned adjacent the transfer station 64 (depicted in FIG. 22).

Referring again to FIG. 14, the transfer station 64 includes a slide assembly 160 for moving the packages 16 of medications/supplements 20 from the transfer nest 112, and a queue support 162 for receiving the packages 16 of medications/supplements from the transfer nest 112 and supporting them until the carrier 32 assigned to receive the packages 16 of medications/supplements for a particular order is positioned at the queue support 162 in registration for receiving the packages 16. The slide assembly 160 has a plurality of individually actuatable slide members 164 having upwardly extendable prongs 166 that engage the packages 16 of medications/supplements supported on the transfer nest 112 when the transfer nest 112 has pivoted to the second position. The prongs 166 slide the packages 16 of medications/supplements from the transfer nest 112 into corresponding channels 168 formed in the queue support 162 of the transfer station 64. In the embodiment shown, the channels 168 formed in the queue support 162 are shaped complementarily to the shape of the packages 16 of medications/supplements, in a manner similar to the channels 52 of carriers 32, such that the packages 16 received in the respective channels 168 of the queue support 162 are constrained and allow for movement only along longitudinal directions of the channels 168.

With continued reference to FIG. 15, and referring further to FIG. 16A, operation of the pick device 62 to retrieve selected packages 16 of medications/supplements from the storage tubes 74 supported in the array of bins 72 of the storage units 66 and to place the selected packages 16 in the transfer nest 112 for subsequent transfer to the transfer station 64 will now be described. The pick device 62 has a pick head 110 having four grippers 130 disposed generally circumferentially around a housing 132 of the pick head 110 and arranged such that pairs of grippers 130a, 130c and 130b, 130d are positioned on diametrically opposite sides of the housing 132. Each gripper 130 has a gripper arm 170 slidably received in guides 172 coupled to the housing 132 to facilitate movement of the gripper arms 170 along radial directions relative to the housing 132. Springs 174 coupled to the gripper arms 170 and contacting the guides 172 bias the gripper arms 170 in directions radially outwardly from the housing 132. The housing 132 of the pick head no is rotatable to index the grippers 130 from positions adjacent the storage tubes 74, for engaging and retrieving packages 16 of medications/supplements, to positions adjacent the transfer nest 112 for placing the selected packages 16 into one or more slots 134 of the transfer nest 112.

Figure 18D:
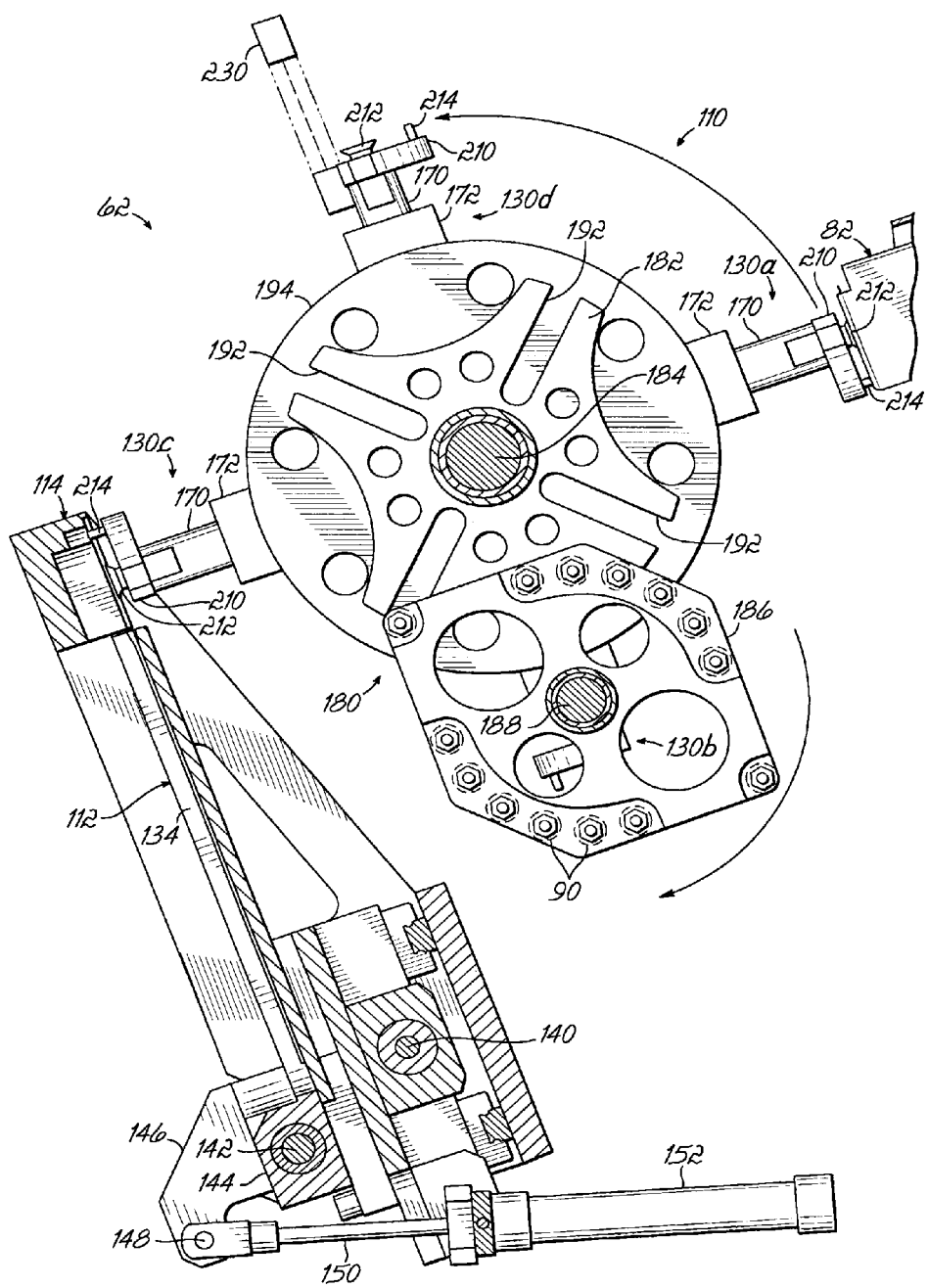

As depicted in FIG. 18D, the pick head 110 of the embodiment shown is rotatably indexed by a Geneva drive mechanism 180 for successive, intermittent positioning of the respective grippers 130 adjacent the storage module 60 and the transfer nest 112. A driven wheel 182 is rotatably supported on a central shaft 184 of the pick head 110 and is driven for intermittent rotation by a drive wheel 186 supported on a rotating drive shaft 188 spaced from the central shaft 184. As the drive wheel 186 rotates, engagement rods 190 positioned on diametrically opposed sides of the drive wheel 186 engage corresponding slots 192 formed in the driven wheel 182 to rotate the driven wheel 182. The driven wheel 182 is coupled to an index plate 194, which is in turn coupled to the pick head housing 132, whereby intermittent rotational motion is imparted to the housing 132 to move the grippers 130.

The pick head 110 is also configured to move the gripper arms 170 along directions extending radially from the housing 132 to facilitate engaging the packages 16 of medications/supplements stored in the storage tubes 74 and placing the selected packages 16 within slots 134 on the transfer nest 112. Radial movement of the gripper arms 170 is controlled by a rotating cam plate 200 disposed within the pick head housing 132. An aperture 202 formed in the cam plate 200 defines a cam surface 204 that engages follower pins 206 coupled to the proximal ends 208 of the gripper arms 170. In the embodiment shown, the cam surface 204 is configured to move one pair of diametrically opposed gripper arms 170 radially outwardly (associated with grippers 130b and 130d, for example) while the other oppositely disposed pair of gripper arms 170 is moved radially inwardly (associated with grippers 130a and 130c, for example). The inward/outward motion of the gripper arm pairs is alternated as the cam plate 200 rotates within the pick head housing 132.

Figure 17:
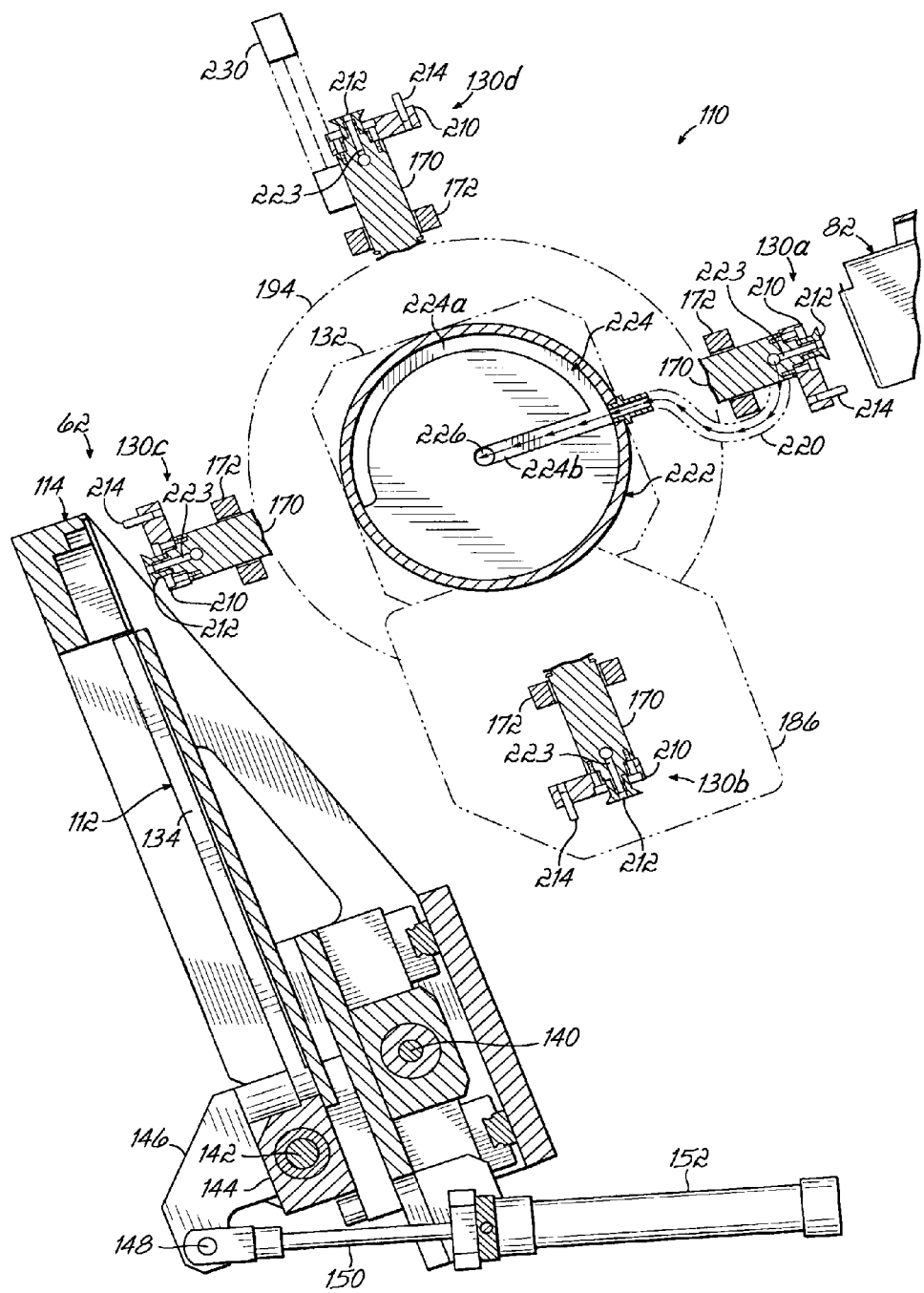
FIG. 17 is a partial cross-sectional view depicting a vacuum manifold of the pick device.

The distal end 210 of each gripper arm 170 includes a suction cup 212 for applying vacuum pressure to the planar closure 22 of a package 16 positioned adjacent the dispensing slot 84 of a storage tube 74. The distal end 210 of each gripper arm 170 may include a pin 214 for positively engaging an edge of the closure 22 of the package 16 to facilitate lifting the package 16 from the dispensing slot 84 of the storage tube 74. However, the pin 214 may be eliminated to avoid possible damage to the packages 16 during transfer to the slots 134. Vacuum pressure is supplied to the suction cups 212 by conduits 220 that are operatively coupled to a vacuum manifold 222 disposed within the pick head housing 132 and to a vacuum passage 223 in the gripper arm 170. As shown in more detail in FIG. 17, the vacuum manifold 222 comprises a vacuum passage 224 configured to provide vacuum pressure to the suction cups 212 of the respective grippers 130 at appropriate positions of the grippers 130 relative to the pick head housing 132 to facilitate retaining the packages 16 on the distal ends 210 of the gripper arms 170 from the time that the packages 16 are retrieved from the storage tubes 74 until the packages 16 are placed in the slots 134 of the transfer nest 112. To this end, the vacuum passage 224 has a first portion 224a that extends generally circumferentially around a portion of the pick head housing 132, and a second portion 224b extending in a radial direction along the manifold 222 and communicating with an outlet port 226 coupled to a source of vacuum pressure.

With continued reference to FIGS. 16A and 16B, the retrieval of a selected package 16 from a storage tube 74 by the pick head 110 will now be described. In FIG. 16A, the pick head 110 has been moved to a location relative to the storage module 60 to position a first gripper 130a adjacent a storage tube 74 supported in the storage module 60 and containing a plurality of packages 16 of a particular medication/supplement required to fill an order. The distal end 210 of the first gripper arm 170 is spaced from the end cap 82 of the storage tube 74. With the first gripper 130a positioned adjacent the storage tube 74, vacuum pressure is supplied to the suction cup 212 by the vacuum manifold 222. The cam plate 200 rotates to move the first gripper arm 170 in a direction toward the end cap 82 of the storage tube 74 such that the suction cup 212 engages the surface of the closure 22 of the lower-most package 16 in the storage tube 74, and the pin 214 engages the side edge of the package 16, as depicted in FIGS. 12A and 12B. The vacuum pressure applied at the suction cup 212 draws the package 16 firmly against the distal end 210 of the first gripper 130a, and lifts the package 16 through the dispensing slot 84 of the end cap 82 as the Geneva drive mechanism 180 is indexed to the next position, as depicted in FIGS. 18D and 19A.

Figure 19A:
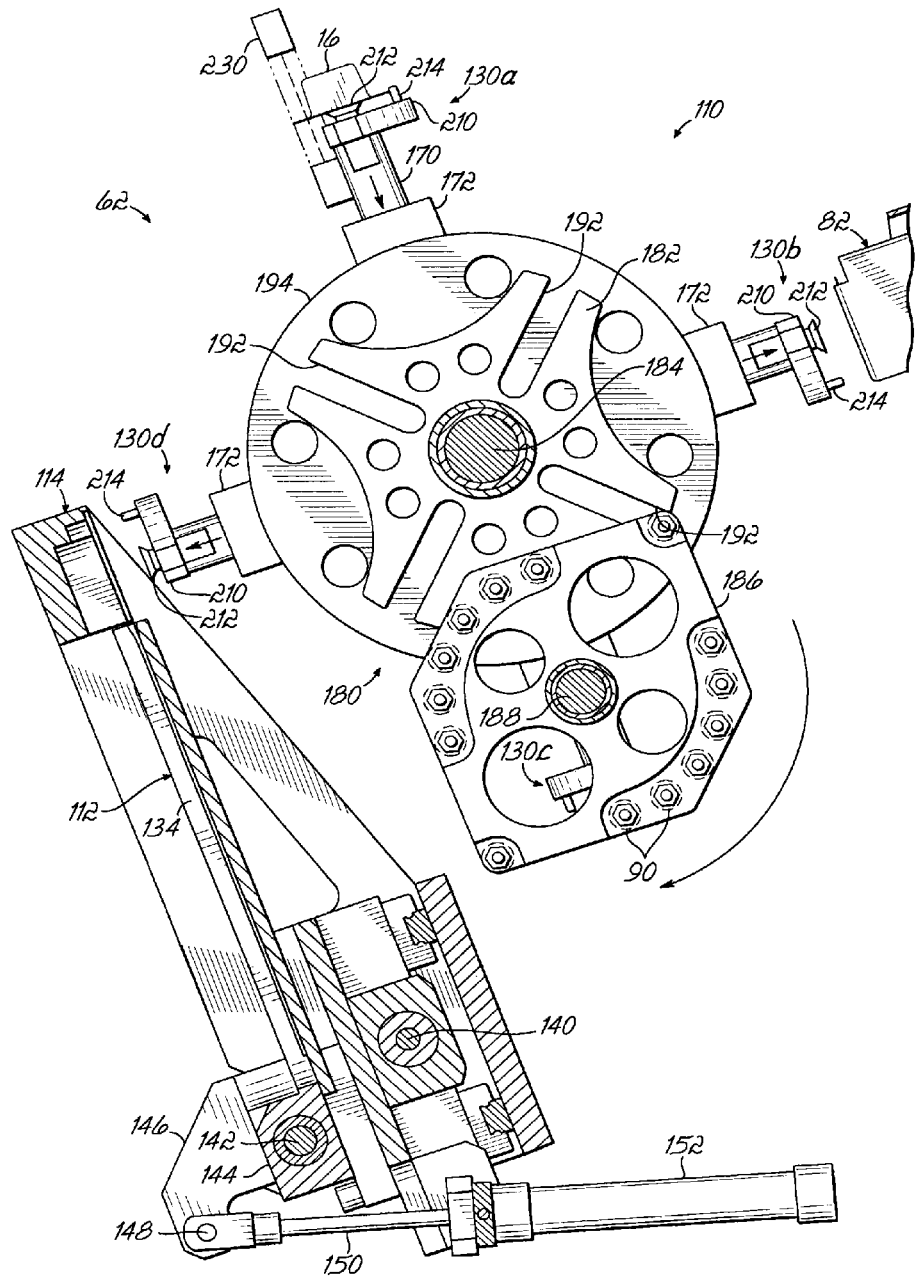
Figure 19B:
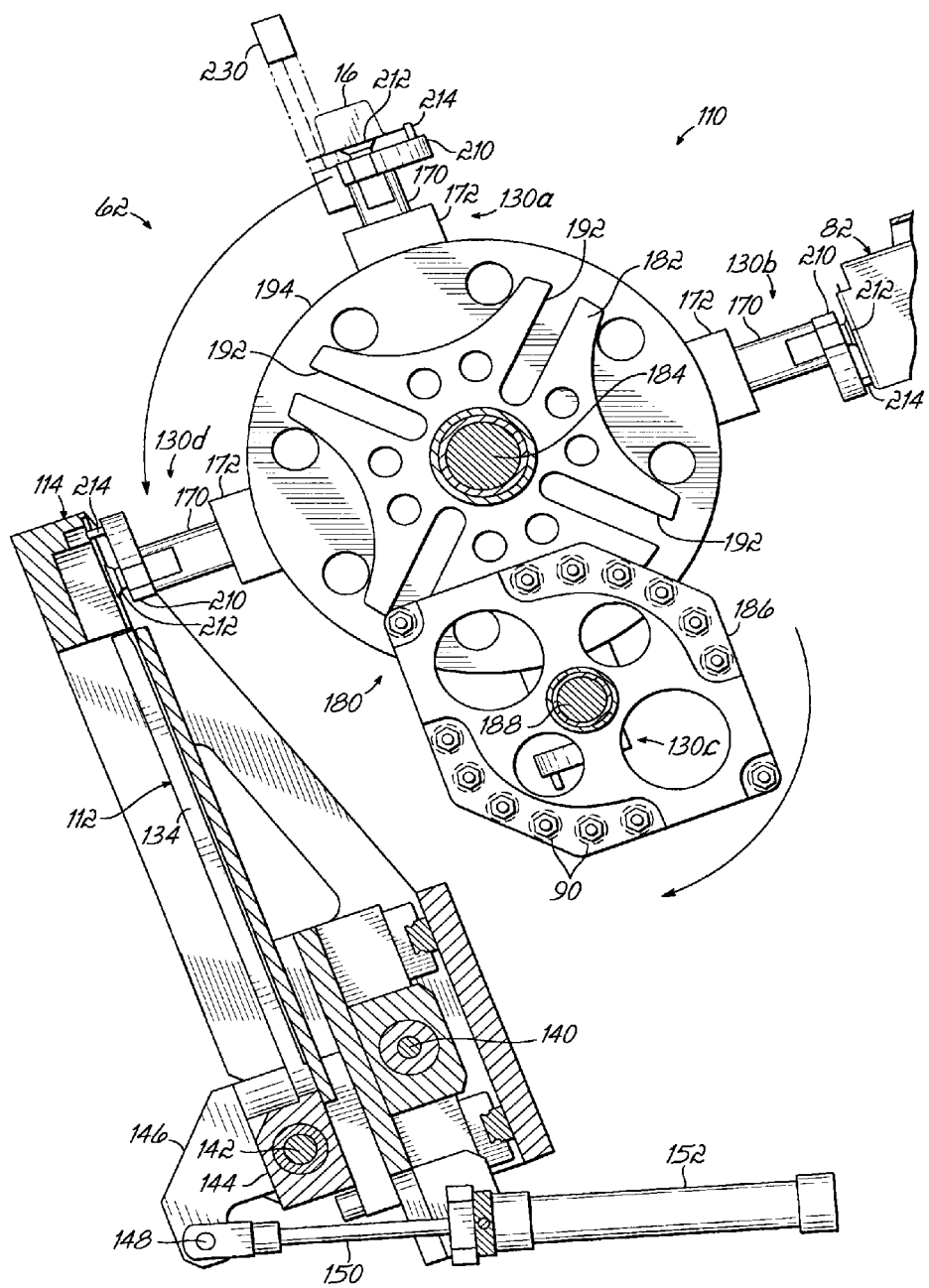

Referring now to FIG. 19A, the selected package 16 is supported on the distal end 210 of the first gripper 130a adjacent a sensor 230 configured to detect the presence of a package 16 on the first gripper 130a. The sensor 230 may also be configured to read machine readable information provided on the package 16. The sensor 230 can therefore be used to confirm that a package 16 was retrieved by the first gripper 130a and that the selected package 16 is the package 16 intended to be selected to fill the order. Indexing of the Geneva drive mechanism 180 to move the first gripper 130a and the package 16 supported thereon adjacent the sensor 230 also moves the second gripper 130b into a position for engaging and retrieving another package 16 from the storage tube 74, in the event that more than one dose of the medication/supplement is required to fill the order. If a different medication/supplement is required, the pick device 62 may be moved on the gantry 116 to position the second gripper 130b adjacent an appropriate storage tube 74 containing packages 16 of the desired medication/supplement.

Figure 19C:
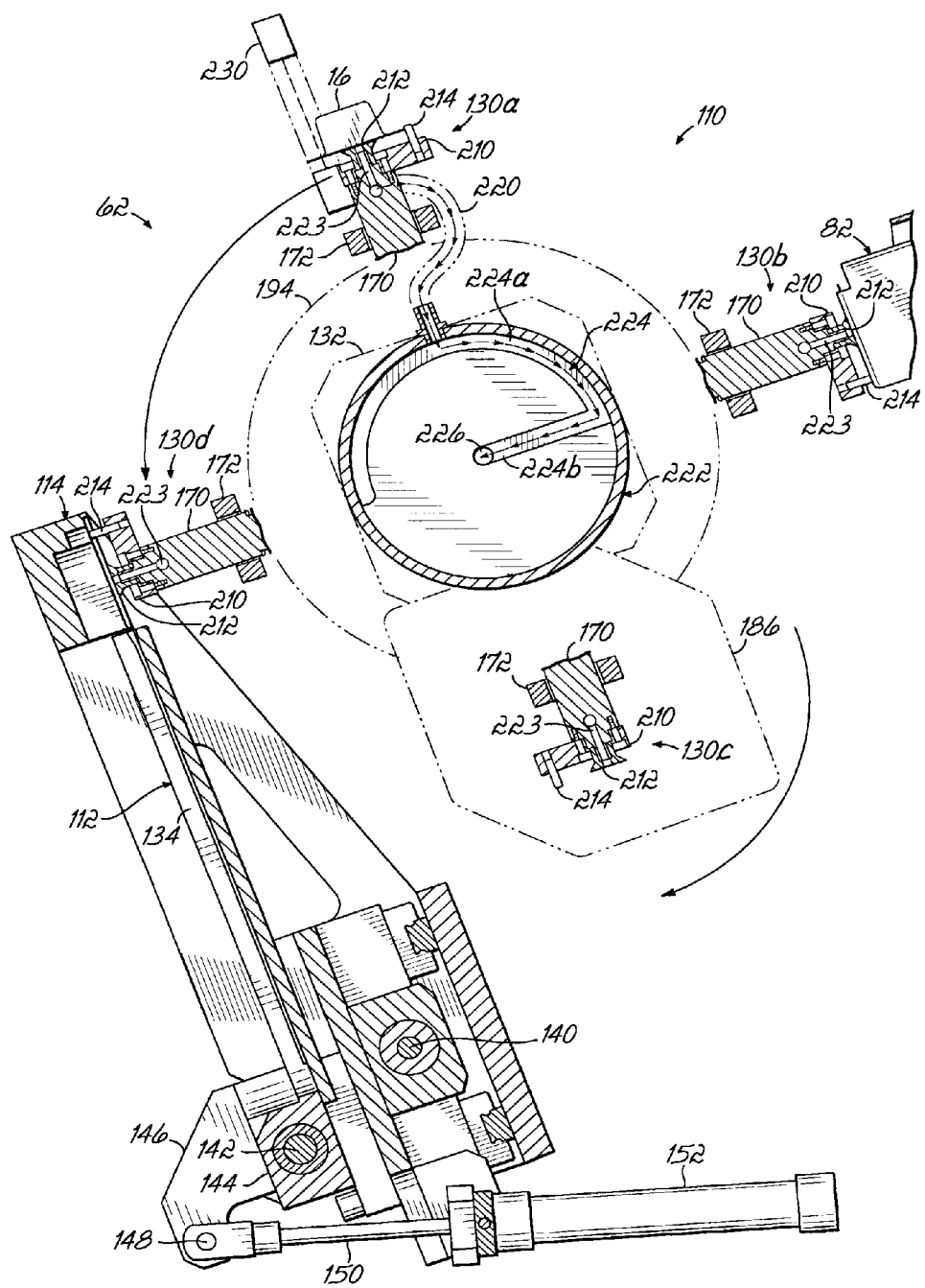

The cam plate 200 then rotates to move the first gripper 130a supporting the package 16 in a direction radially inwardly toward the pick head housing 132, while at the same time the second gripper 130b is moved radially outwardly to engage a subsequent package 16 supported in a respective storage tube 74 for retrieval of the package 16 as described above. FIG. 19C depicts the vacuum manifold 222 and illustrates how vacuum pressure is maintained at the suction cup 212 of the first gripper 130a adjacent the sensors 230.

Figure 20A:
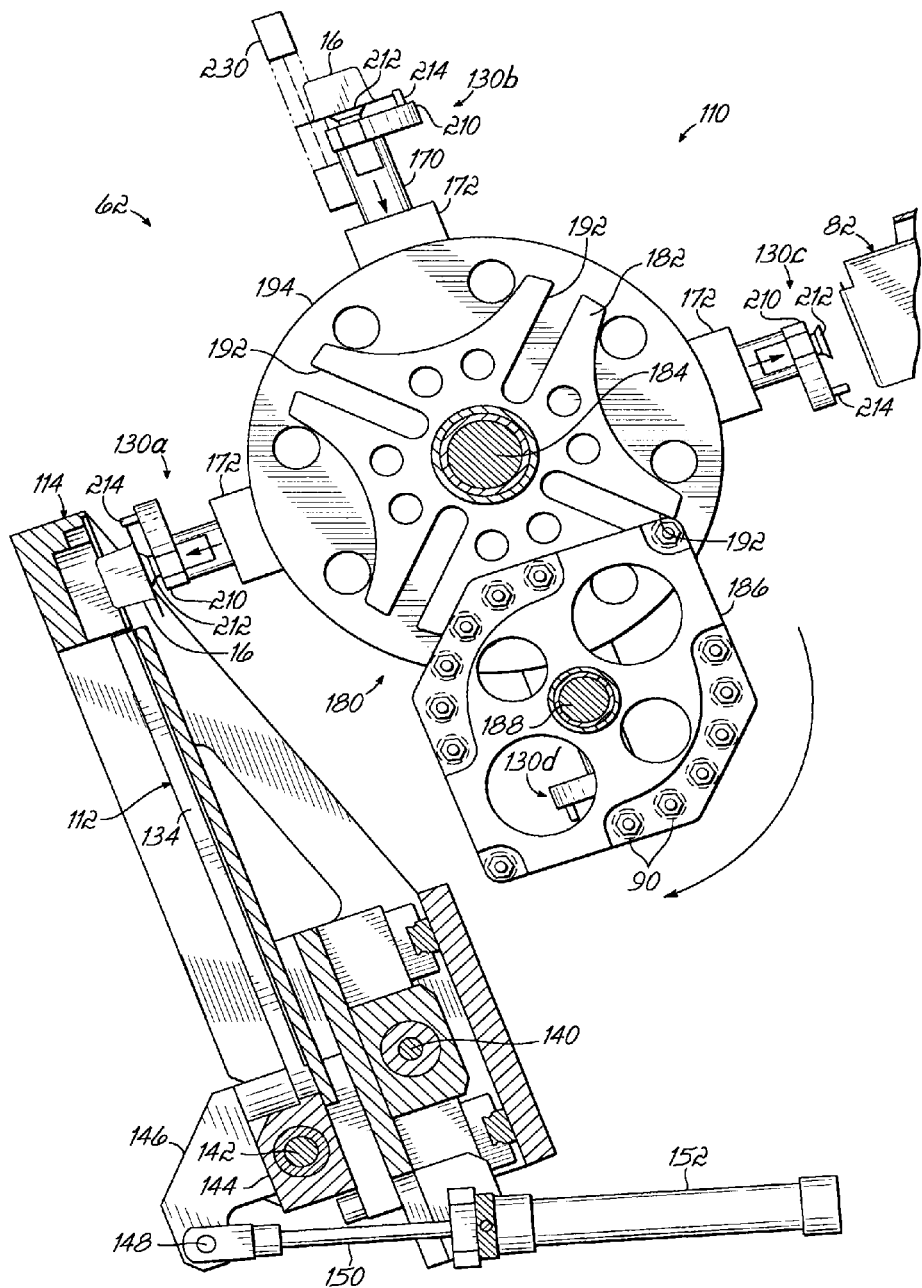
Figure 20B:
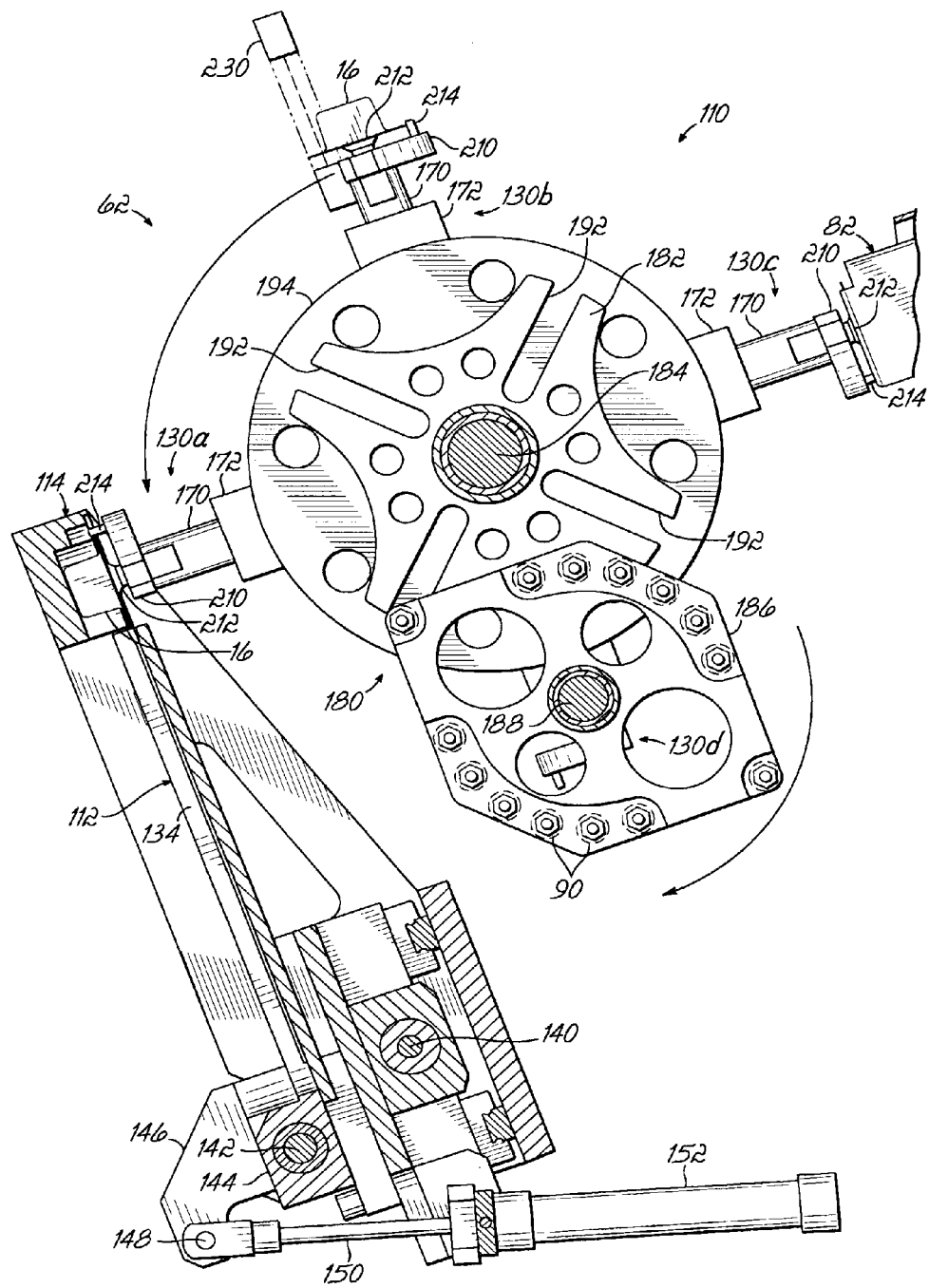
Figure 20C:
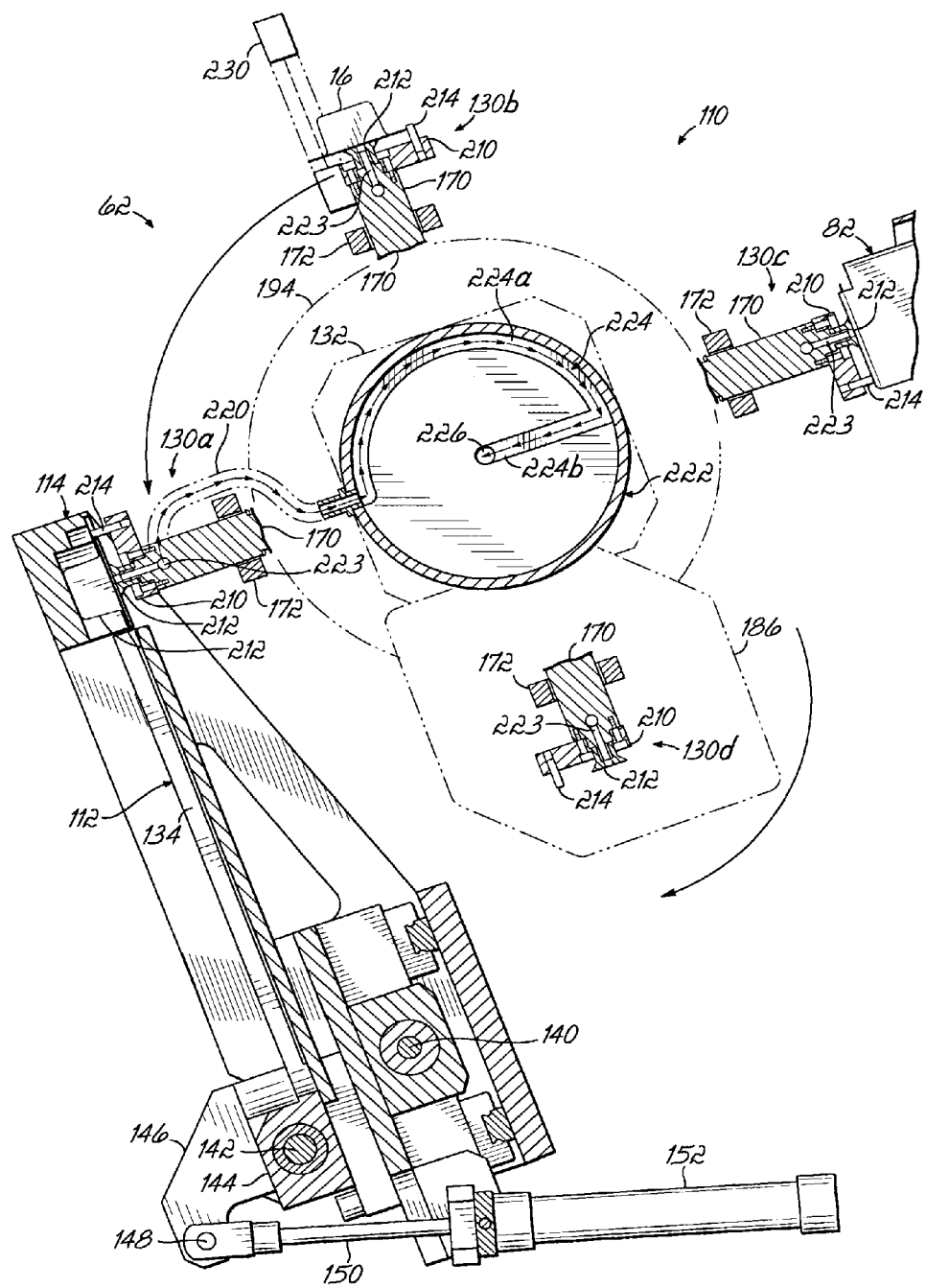
Figure 21:
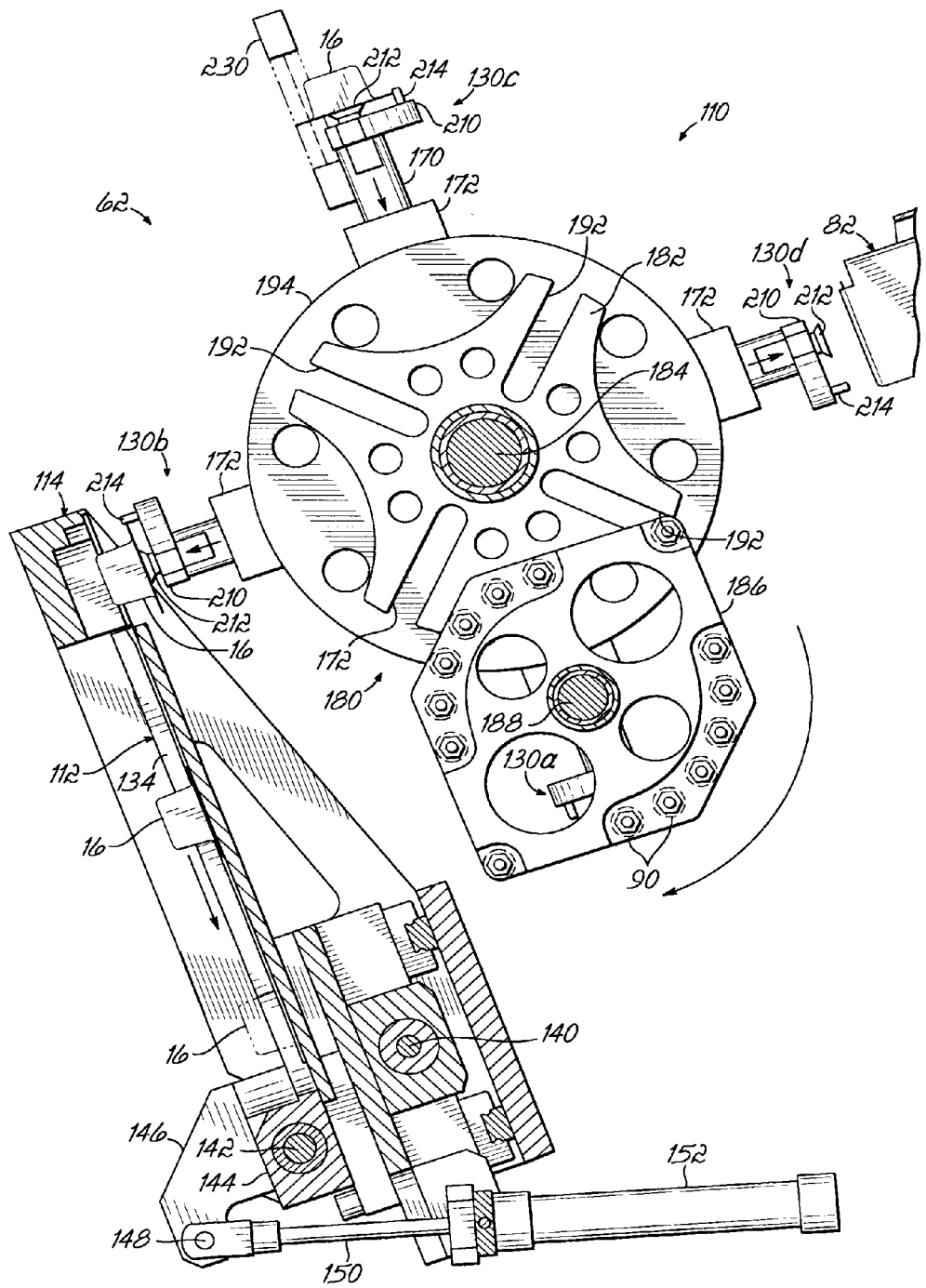

Referring now to FIG. 20A, the Geneva drive mechanism 180 indexes the first gripper 130a to a position adjacent the transfer nest 112, while simultaneously moving the second gripper 130b (now supporting a package 16) adjacent the sensor 230, and moving the third gripper 130c adjacent the storage module 60 to a position to retrieve a subsequent package 16 from the same storage tube 74, or from a different storage tube 74, as may be required. As the drive wheel 186 of the Geneva drive mechanism 180 continues to rotate, the cam plate 200 rotates to move the first gripper 130a radially outwardly to position the package 16 in registration with a selected slot 134 of the transfer nest 112, as depicted in FIG. 20B. Simultaneously, the second gripper 130b is moved in a direction radially inwardly, while the third gripper 130c is moved radially outwardly to engage a subsequent package 16. FIG. 14C illustrates the vacuum manifold 222 with the first gripper 130a adjacent the transfer nest 112 and shows how vacuum pressure is applied to the suction cup 212 at this position. As the first gripper 130a is subsequently indexed to the next position, vacuum pressure applied through the first portion 224a of the vacuum passage 224 is shut off to the conduit 220, and the package 16 is released into the slot 134 on the transfer nest 112, as illustrated in FIG. 21, which depicts the pick head 110 indexed to the next successive position by the Geneva drive mechanism 180, whereby the second gripper 130b is in position to place a package 16 supported on the second gripper 130b onto the transfer nest 112. After the last package 16 in an order is picked, the Gantry 116 moves the pick device 62 to a location between the storage units 66, where there are no storage tubes 74. Since there are no packages 16 present, the pick device 62 can advance two positions thereby transferring the packages already supported by the remaining two grippers 130 into the slot 134 of the transfer nest 112 without acquiring additional packages 16, completing the order.

Figure 22:
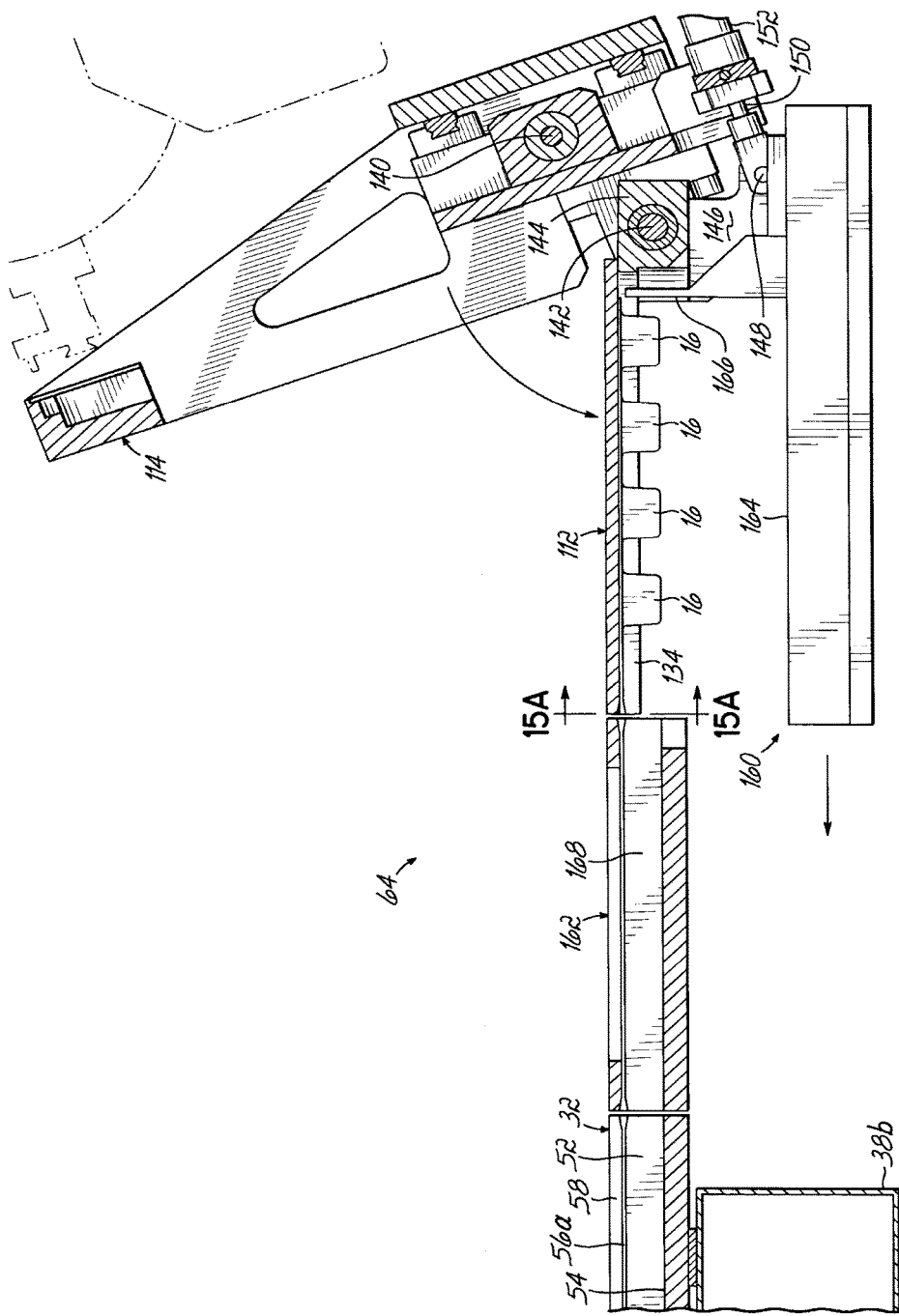
FIGS. 22-24 are sequential cross-sectional side-elevational views of the transfer mechanism on the pick device transferring unit dose pharmaceutical packages to a transfer station adjacent the conveyor of the dispensing system according to one embodiment of this invention.
Figure 23:
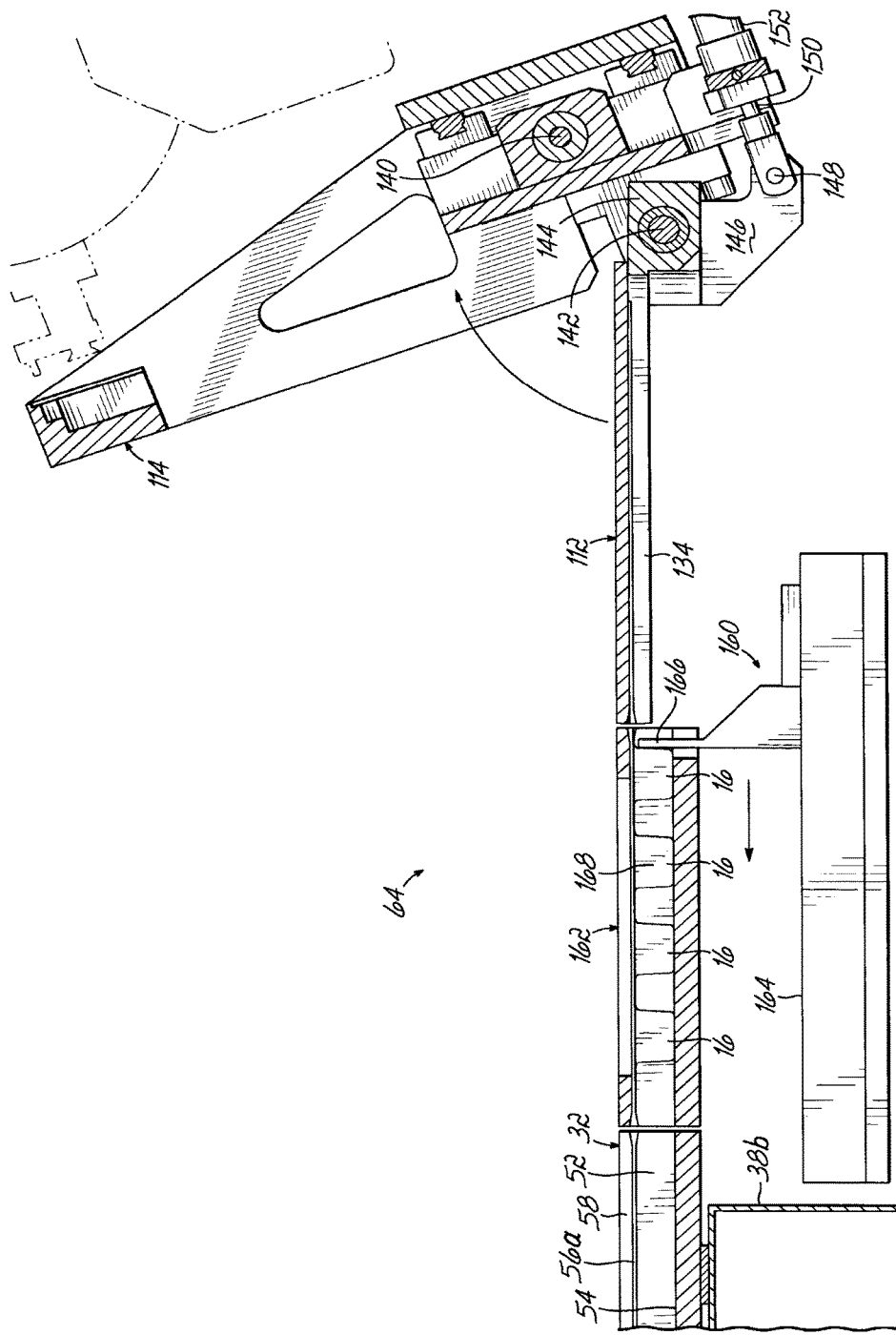
Figure 24:
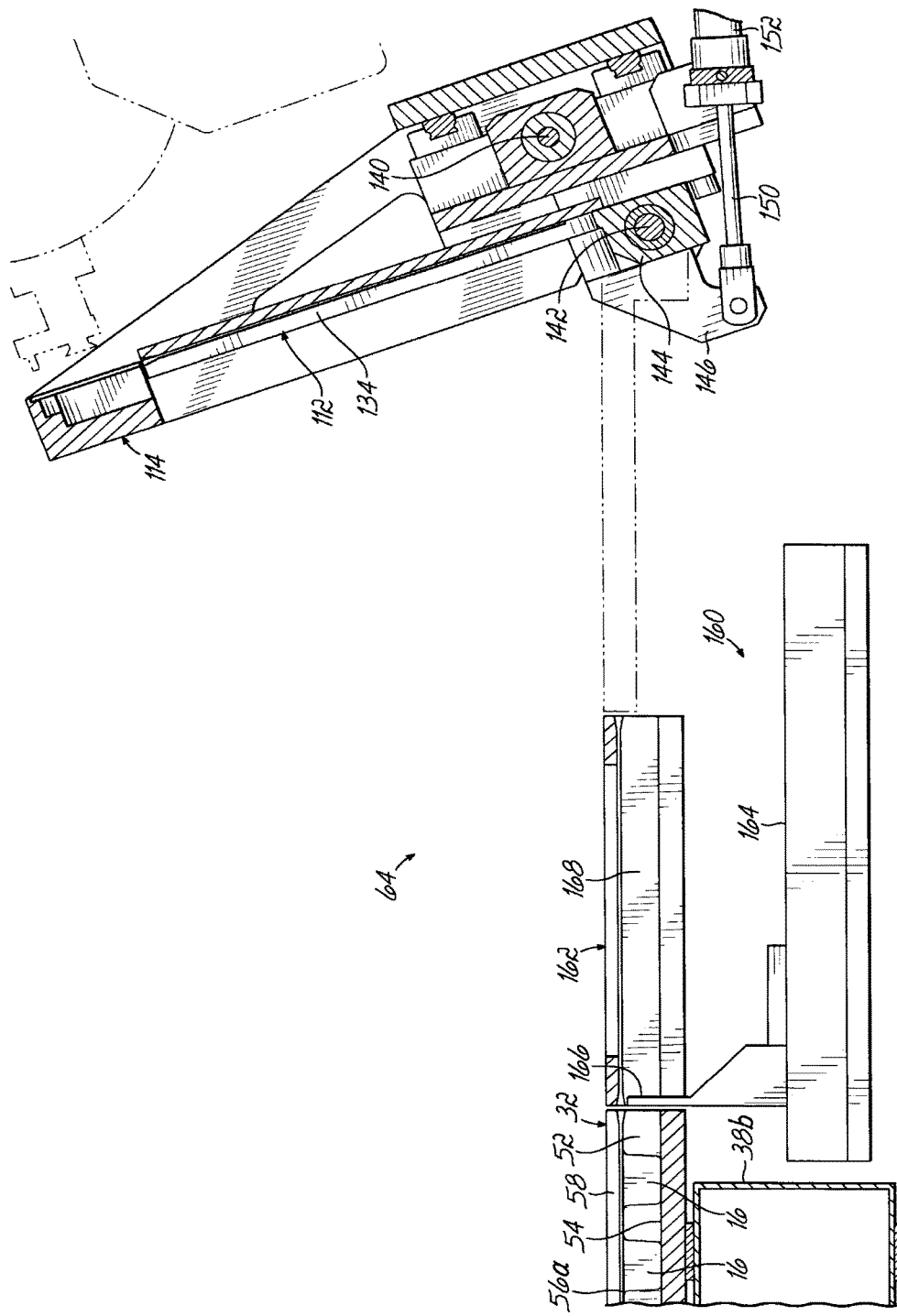

After the packages 16 of medications/supplements associated with one or more orders are placed on the transfer nest 112, the pick device 62 is moved by the gantry 116 to a position adjacent the transfer station 64. The pneumatic piston 152 is then actuated to pivot the transfer nest 112 from the first position adjacent the pick head 110 to the second position adjacent the slide assembly 160 of the transfer station 64, as depicted in FIG. 22. With the transfer nest 112 in the second position, one or more of the slide members 164 may be actuated to push the selected packages 16 from the slots 134 on the transfer nest 112 into corresponding channels 168 on the queue support 162 in registration with the slots 134 of the transfer nest 112, as depicted in FIG. 23. The packages 16 of medications/supplements supported in the queue support 162 are held until the designated carrier 32 assigned to receive the particular order associated with the medications/supplements is in position adjacent the corresponding channel 168 of the queue support 162. Thereafter, the prongs 166 of the slide member 164 are further actuated to push the corresponding packages 16 of medications/supplements from the queue support 162 into the appropriate carrier 32 on the conveyor 30, as depicted in FIG. 24.

After the packages 16 of medications/supplements have been moved from the transfer nest 112 to the slide assembly 160, the transfer nest 112 is pivoted from the second position back to the first position, adjacent the pick head 110, and the pick device 62 is moved on the gantry 116 to a position adjacent a selected storage tube 74 for retrieval of a package 16 required for the next order. The process described above is repeated to assemble additional orders. After the packages 16 of medications/supplements for an order have been transferred from the queue support 162 to the assigned carrier or carriers 32, the slide members 164 return to retracted positions as depicted in FIG. 22 to await the delivery of the next batch of packages 16 from the pick device 62. Having received all of the packages 16 of medications/supplements required to fill the orders, the carriers 32 continue along the conveyor 30 to a packaging station for subsequent processing into appropriate containers for delivery to the one or more long-term care facilities. A camera station with at least one sensor 41 is positioned downstream of the low-demand module 14 and upstream of the packaging or bagger station 26 to verify the medications/supplements 20 in the carriers 32 via the bar code 24 on each package 16 in the carrier 32.

The low-demand module 14 according to one embodiment of this invention is disclosed in related patent application Ser. No. 12/559,601, filed on Sep. 15, 2009 and incorporated by reference herein in its entirety.

In the embodiment shown, the low-demand module 14 of the dispensing system 10 includes five individual transfer stations 64 configured to receive packages 16 of medications/supplements for transfer to respectively assigned carriers 32 on the conveyor 30, as described above. It will be appreciated, however, that the dispensing system may alternatively include fewer than five transfer stations 64, or greater than five transfer stations 64, as may be desired for the particular requirements of the dispensing system 10. The provision of one or more transfer stations 64 enables the pick head 110 to preselect the packages 16 of medications/supplements associated with a plurality of orders and transfer the packages 16 into respective queue supports 162 to serve as a buffer and to accommodate substantially continuous operation of the conveyor 30.

The dispensing system 10 further includes a control 240 configured to receive orders for medications/supplements and to process the orders for delivery to a LTC facility. Orders may be electronically received by the control 240 from one or more LTC facilities, such as by transmission over a network, or by any other suitable method. Alternatively, orders can be input directly into the control 240 via an appropriate interface, such as a keyboard or other suitable devices. The control 240 identifies which medications/supplements 20 are required from the high-demand module 12 and the low-demand module 14 to fill each order. In one embodiment, the orders corresponding to each medication pass to be administered to a particular patient for that particular day are processed by the control 240 such that the packages 16 of medications/supplements 20 for each medication pass to be administered to the patient are assembled into a package, and the packages of medication passes are then grouped together in totes 28 for delivery to the LTC facility.

The control 240 assigns one or more carriers 32 to receive the packages 16 of medications/supplements for each order. The control 240 then controls the movement of the carriers 32 on conveyor 30 through the high-demand module 12 and the low-demand module 14 to receive the packages 16. The control 240 controls operation of the low-demand module 14 to retrieve the packages 16 of medications/supplements for the orders ahead of the arrival of the carriers 32 assigned to the orders and while the carriers 32 are receiving the ordered medications/supplements from the high-demand module 12 as the carriers 32 are moved past the high-demand module 12. The transfer stations 64 provide a buffer to accumulate the medications/supplements in advance of the arrival of the carrier 32 for the specific order. The control 240 is coupled to an order entry database and via a web service the orders are passed to the dispensing system 10 one at a time. Alternatively, multiple orders may be passed at a time, for example, ten orders passed at a time. As such, the remaining, subsequent orders are buffered in the database.

In another embodiment, the dispensing system 10 may be configured to receive and process short turn-around time orders ("stat orders") that are received separately from the periodically received orders from the LTC facilities. The control 240 integrates the stat orders into the orders being processed and may direct the assembled stat order to a separate location for subsequent handling. The control 240 may also be configured to receive signals from various sensors associated with the dispensing system 10 to facilitate managing operation of the dispensing system 10. For example, in one embodiment, the control 240 is configured to receive signals from sensors 97, 99, 230 of the low-demand module 14 related to the detection of packages 16 in a storage tube 74, the presence of storage tubes 74 in a bin 72, and the presence of a package 16 supported on a gripper 130, respectively. When the control 240 receives a signal from a sensor 97 indicating that the storage tube 74 associated with the sensor 97 is empty, control 240 provides a signal to an operator indicating that the storage tube needs to be replaced or replenished. When control 240 receives a signal from a sensor 99 indicating that a storage tube 74 is not detected in the associated bin 72, the control may provide a signal to an operator indicating the detected absence of a storage tube 74. Inventory status is maintained in the control 240 and the sensor 230 provides a fail-safe check in case the inventory is not correct in that the control 240 will not direct the pick device 62 to pick from an empty location. When control 240 receives a signal from a sensor 230 indicating that a package 16 was not detected on a gripper 130, the control may provide a signal to an operator that the package 16 was not detected. The control 240 may also flag the order associated with the detected absence of the package 16 based on input from camera station with at least one sensor 41 for separate processing to confirm that the order is faulty and, optionally, to correct the error in filling the order. The control 240 may also be configured to stop operation of the dispensing system 10 when a detected error will adversely affect operation of the dispensing system 10 to fill orders.

The control 240 may also be configured to optimize the picking of packages 16 from the storage module 60 and the transfer of the packages 16 to the carriers 32. In particular, the control 240 may be configured to monitor the order frequency of the medications/supplements and to assign locations for the storage tubes 15 or 74 in the bins 72 of the storage modules 60, 13 based on order frequency. For example, the control 240 may assign locations for storage tubes 74 containing medications/supplements 20 that have a relatively higher order frequency to be placed in bins 72 that are located relatively lower in the storage units 66 and/or are positioned relatively closer to the transfer stations 64 so that the distance required to be traversed by the pick device 62 to retrieve packages 16 of high-demand medications/supplements is minimized, thereby decreasing the time required to transfer packages 16 for the orders in the queue supports 162. Accordingly, the particular locations of the storage tubes 15, 74 of the storage modules 13, 60 can be dynamic and may be modified by the control 240, as may be desired for efficient processing of orders.

In another aspect, the control 240 may be configured to track the dispensing of medications/supplements from the storage tubes 15, 74 within the modules 12, 14 and to provide signals to an operator when the supply of packages 16 in a given storage tube 15, 74 is becoming low. This allows replacement of the storage tubes 15, 74 or, alternatively, replenishment of the packages 16 within the storage tubes 15, 74, at convenient times. The dispensing system 10 is also configured to facilitate replacement of the storage tubes 15, 74 or, alternatively, replenishment of the packages 16 within the storage tubes 15, 74, on-the-fly while the dispensing system 10 is operating to fill orders. In particular, the configuration of the storage modules 13, 60 facilitates access for removal and replacement of storage tubes 15, 74 while the dispensing system is operating to fill orders. In the event that the pick device 62 attempts to retrieve a package 16 from a storage tube 74 when the storage tube 74 has been removed for replacement, the control 240 receives a signal from sensor 99 associated with the bin 72 and may control the pick device 62 to wait until the storage tube 74 has been replaced before attempting to retrieve the package 16.

While FIG. 1 illustrates the dispensing system 10 as having a high-demand module 12 and a low-demand module 14 provided on only one side of the conveyor 30, the dispensing system 10 may alternatively be configured with high-demand modules 12 and low-demand modules 14 provided on both sides of the conveyor 30, to accommodate the quantity of medications/supplements and throughput requirements of the system, as may be desired. In such a configuration, the high-demand modules 12 and low-demand module 14 on both sides of the conveyor 30 are controlled by a common control 240, however, the packages 16 of medications/supplements may be transferred to the carriers 32 moving along the conveyor 30 from the high-demand modules 12 and low-demand modules 14 on both sides of the conveyor 30.

One aspect of the dispensing system of this invention is the structure and process for maintaining positive control (i.e., no free-fall or gravity induced movement of the unit dose packages) through the dispensing operation of each module 12, 14. This aspect minimizes mishandled, lost, errant or jammed packages 16 in the filling of patient orders.

Additionally, at least three levels of buffering for the advanced picking of medications/supplements 20 in the order filling process are provided with the dispensing system 10. The dispensing system 10 of this invention utilizes at least three distinct levels of buffering or picking packages 16 in advance of the arrival of the conveyor driven carrier 32. For example, the physical distance between the upstream high-demand module 12 and the downstream low-demand module 14 that the carriers 32 must travel allows for one level of buffering. With respect to the low-demand module 14, the multiple transfer nests located on the pick device allow for an additional level of buffering such that specific medications/supplements can be picked from the storage tubes 74 of the low-demand module 14 and placed in any of the five transfer nests on the pick device and remain there while additional medications/supplements 20 are picked in advance of the approaching carriers 32 assigned to the respective orders.

A third level of buffering is the transfer stations 64 positioned adjacent the conveyor path 31 in the low-demand module 14. The medications/supplements 20 picked and held in the transfer nests 112 on the pick device 62 can be transferred to one of the transfer stations 64 in advance of the arrival of the designated carriers 32 for the associated order. While those medications/supplements reside at the transfer station 64 awaiting transfer to the approaching designated carriers 32, the pick device 62 is free to return to the storage tubes 74 of the low-demand module 14 to pick medications/supplements 20 for subsequent orders. Therefore, the dispensing system 10 of this invention utilizes at least three levels of buffering and it is believed that this feature is both beneficial and efficient compared to known dispensing systems.

Labor savings and safety of the system have been previously identified herein. However, the fact that the control 240 may compare the unit dose package barcode 24 to the prescription order and the med pass bag 47 barcode compared to the carrier ID (and therefore back to the prescription order) at the time of prescription fill is an advantage. This feature is the basis for eliminating the need for added nurse or other practitioner checks often required in manual and other automated dispensing systems (the first being at order entry and the second being at conversion from bulk to unit dose in the prepack operation). This method of cross-checking both the unit dose packages 16 and the med pass bag 47 back to the original order are a beneficial aspect of this invention.

Figure 25A:
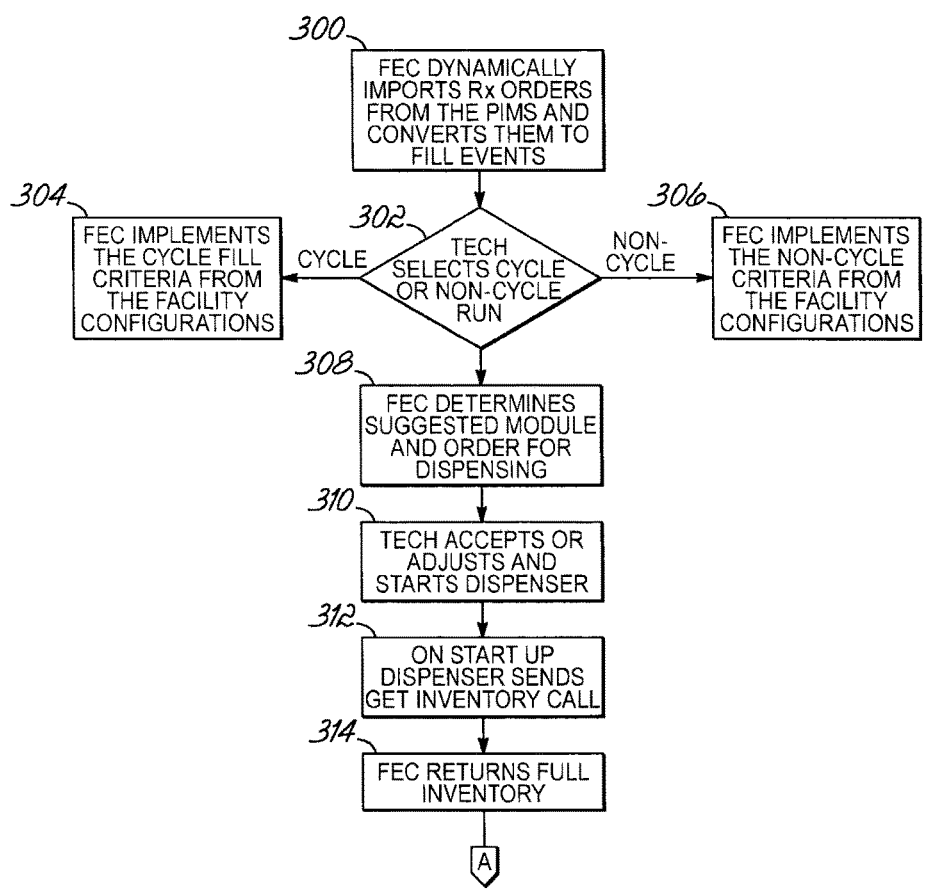
FIG. 25A-25B is a flow chart depicting the overall operation of the dispensing system according to one embodiment of this invention.

Referring to FIGS. 25A-31, flow charts depicting the operation of dispensing system 10 are presented. In FIGS. 25A-25B, a flow chart depicting the overall operation of the dispensing system 10 according to one embodiment of this system is shown. FIGS. 25A-25B outline the high level functions of the dispensing system 10 and its interactions with the control 240 or fill event configurator (FEC). The interaction between the components of the dispensing system 10 and the FEC or control 240 is facilitated by a group of web services that pass packets of data back and forth between the database and the components of the dispensing system 10.

The dispensing system 10 is an interrelated collection of the various stations that function independently and in coordination via the FEC or control 240 with one another to process patient orders for medications/supplements. The FEC or control 240 provides for each of the stations to have completed the work required to fill a particular order prior to the conveyor 30 and associated carriers 32 being indexed to the next position. As such, each of the stations or modules can function asynchronously to facilitate parallel processing of individual medications/orders. The dispensing system 10 continues to operate until each of the assigned tasks is accomplished and at that point, an additional data packet is requested and transferred to the FEC/controller 240. The dispensing system 10 continues to request data packets until a subsequent data packet is delivered or the dispensing system 10 is shut down.

Figure 25B:
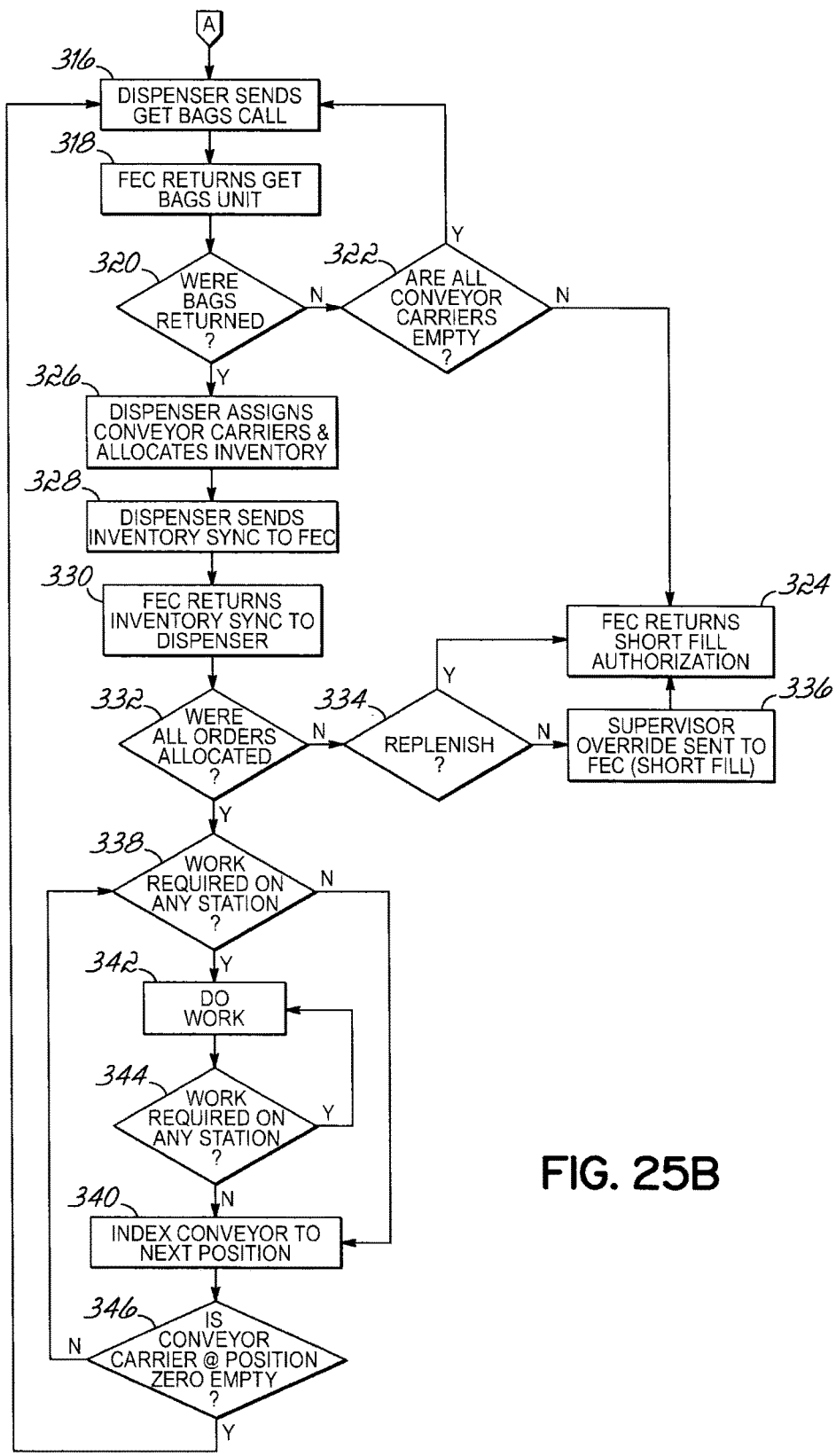

The dispensing system 10 as depicted in FIGS. 25A-25B accepts prescription orders from a pharmacy information management system (PIMS) through the FEC or control 240. The dispensing system 10 picks and packs the orders based on rules received from the FEC for such operation.

Referring to FIGS. 25A-25B, the dispensing system 10 operations can be described as follows. To begin filling and processing a prescription order for a medication/supplement, the control or FEC or control 240 at 300 dynamically imports the prescription order from the pharmacy information management system or PIMS. Then at 302 a technician selects a cycle run 304 or non-cycle run 306 and the FEC implements the criteria from designated facility configurations for processing the prescription order. For a non-cycle run 306, the criteria from the facility configuration is implemented on a non-cycle basis. Next, the FEC or control 240 determines the suggested module (high-demand or high-demand module) at 308 for the order. The technician then has the option of accepting or adjusting the suggested order at 310 and to start the dispensing system 10. Once the dispensing system 10 is started, the dispenser sends an inventory call to the FEC at 312 which then returns the full inventory listing at 314.

The overall operation continues in FIG. 25B at which the dispensing system 10 sends a signal at 316 to the bagging system. The FEC or control 240 then returns a get bags unit indicator 318 at which time the system determines at 320 whether the bags were returned with unused medications/supplements. If bags were not returned, then the FEC determines whether all conveyor carriers are empty at 322 and, if so, then the process is returned to the bag call step 316. If they conveyor carriers 32 were not returned empty, then the FEC returns a short-fill authorization signal at 324 for further attention and processing by the technician. If bags were returned at 320, then the dispensing system 10 assigns conveyor carriers 32 at 326 accordingly and allocates appropriate inventory. Next, the dispensing system 10 at 328 sends an inventory synchronization signal to the FEC. The FEC then returns an inventory synchronization signal at 330 to the dispensing system 10 and for determination whether all orders were allocated at 332. If it is determined that the orders were not allocated, then the FEC must determine whether to replenish 334 and, if so, then the process is returned to step 324 for a short-fill authorization. If replenish at 324 is not indicated then a supervisor override order 336 for a short fill is required. If all the orders were allocated, then the control 240 queries whether any work was required by the particular module or station 338 and if no work was required, then the conveyor is indexed to the next position 340. If work is required, then it is accomplished 342 and the work signal is once again queried 344 prior to indexing the conveyor 340 to the next position. Once the conveyor is indexed to the next position, the control 240 queries at 346 whether the conveyor carrier is at a zero empty position and, if so, then the system is returned to the bag call step 316.

Referring to FIG. 26, the operation of the high-demand module 12 is shown. The high-demand module 12 dispenses unit dose packages 16 directly into the carriers 32 on the conveyor 30 and can operate multiple times per conveyor index to increase the throughput of the entire dispensing system 10. The high-demand module 12 operation begins with the control query at 348 of whether the conveyor 30 and associated carriers 32 are on station at the high-demand module 12. If the response is yes, then the control 240 queries at 350 whether work is required for dispensing the unit dose package 16 from the aligned storage tube 15 of the high-demand module 12. If a positive response is indicated, then the package 16 is pushed into the aligned carrier 32 on the conveyor 30 at 352. If it is determined at 354 that the pusher or insertion plunger mechanism 17 is retracted at the home position (FIG. 8), then the control 240 updates the pick status and dispenser inventory at 356 and returns to the work required query step 350. If the insertion plunger mechanism 17 is not identified at its home position, then a fault is indicated 358.

Figure 27:
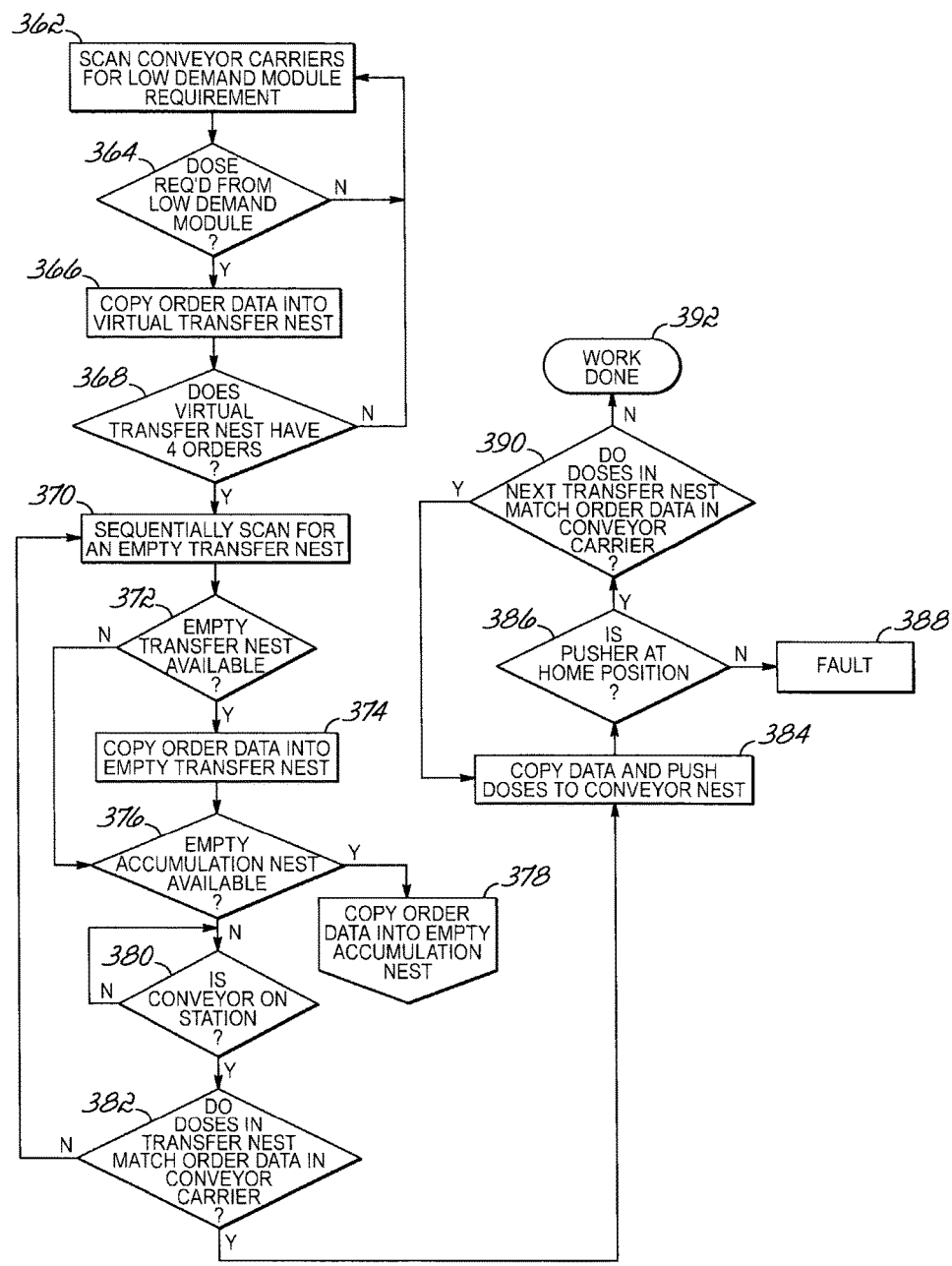
FIG. 27 is a flow chart depicting the operation of a portion of a high-demand dispensing module according to one embodiment of the dispensing system of this invention.

Referring to FIG. 27, the operation of the low-demand module 14 is depicted. The transfer stations 64 of the low-demand module 14 provides an intermediate cue for medications/supplements stored in the low-demand module 14 of the dispensing system 10. This allows the pick device 62 to pre-process orders before the assigned carrier 32 on the conveyor 30 reaches the predetermined transfer location.

As shown in FIG. 27, the operation of the low-demand module 14 begins with a scan 362 of the conveyor carriers 32 for requirements of medications/supplements for a given prescription order from the low-demand module 14. Next, the dose required from the low-demand module 14 is then determined at 364 and if such a requirement is identified, then the order data is copied at 366 into a virtual transfer nest data base which indicates the status of medications and supplements and associated packages 16 in the transfer stations 64 of the low-demand module 14. Next, a determination is made at 368 whether the transfer station 64 has four channels 168 for associated orders. It should be readily understood that this number is not a limitation on this invention and can be any appropriate number for the system requirements. If the virtual transfer nest does not have four orders, then the process returns to scan the conveyor carriers for other low-demand module requirements at 362. If the four channels of the virtual transfer nest are full, then the next step is a sequential scan 370 for empty transfer nests, and, if it is determined at 372 that one is available, then the order data is copied 374 into the transfer nest. If one is not available, then a determination is made at 376 if there is an empty transfer nest. If so, then data is copied into the empty nest 378. If the nest is not available at 376, then it is determined at 380 whether the conveyor 30 is aligned with the transfer station 64. If so, then the determination is made at 382 if the doses in the transfer nest correspond to the order data in the aligned conveyor carriers. If not, then the process is returned to the sequential scan 370 for an empty transfer nest. If so, then the data is copied 384 from the virtual transfer nest and determination is then made if the pusher is at the home position 386. If the pusher is not appropriately positioned, then a fault is detected 388. If the pusher is at the home position, then the associated packages are pushed 390 into the aligned conveyors for completion of this cycle of loading of packages 16 from the low-demand module 14 onto the conveyor carriers 32.

Figure 28:
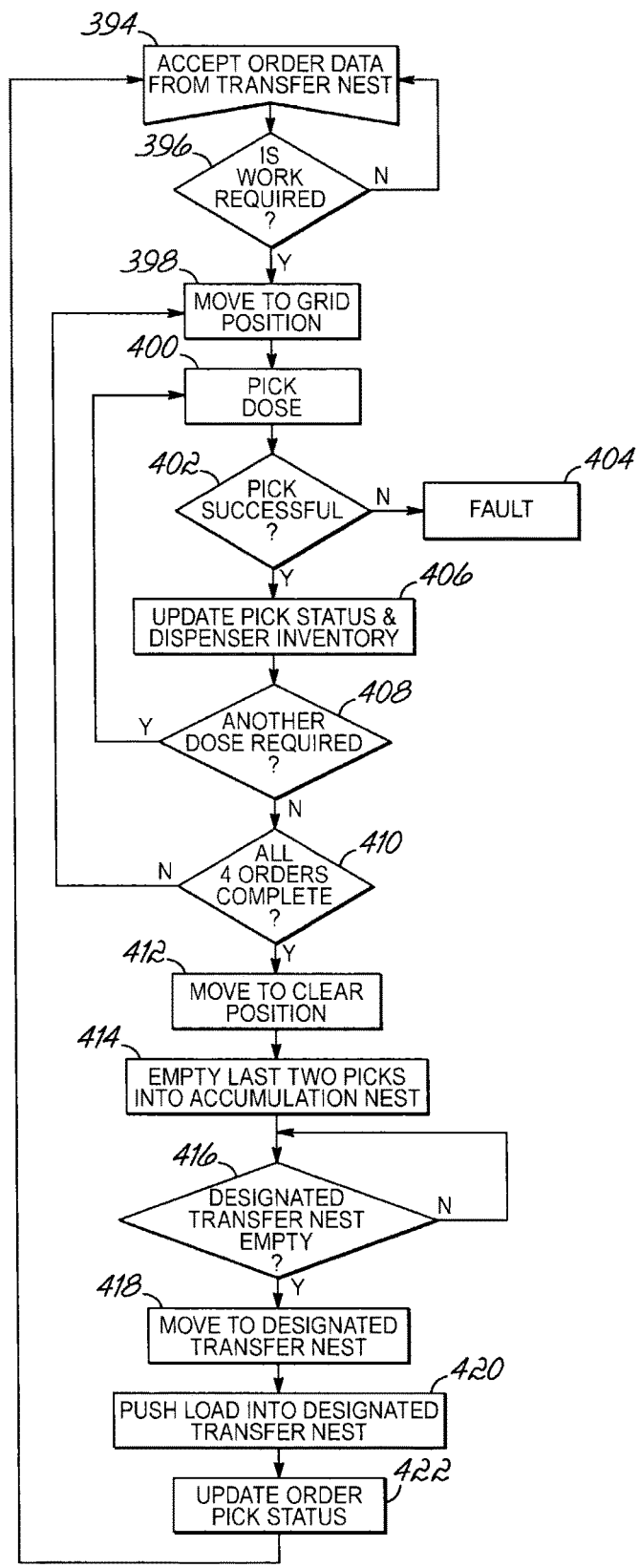
FIG. 28 is a flow diagram depicting the operation of a pick device associated with the high-demand dispensing module according to one embodiment of the dispensing system of this invention.

FIG. 28 shows the operation of the pick device 62 in the low-demand module 14. The pick device 62 functions asynchronously from the conveyor 30 to ensure that the transfer stations 64 (FIG. 27) have the prescribed medications/supplements to complete the orders as the appropriate carriers 32 on the conveyor 30 arrive at the module 14. As shown in FIG. 28, this process begins with an order acceptance step 394 from the transfer nest and then a determination is made 396 whether work is required for the low-demand module 14 to fill the prescription order. If no work is required, then the process returns to the order acceptance step 394. If work is required, then the pick device 62 is moved 398 to the appropriate position relative to the respective storage unit bin 72 to retrieve the appropriate medications/supplements. The pick device 62 then picks 400 the leading package 16 from the storage unit bin 72 and a determination 402 is made whether the pick was successful. If not, a fault indication is issued 404, but if the pick was successful, then the pick status and dispenser inventory is updated 406. The determination 408 is then made whether an additional dose is required from that bin 72 of the storage unit 66 and, if so, then the process is returned to the pick dose step 400. If no further packages 16 are required from that bin 72 of the storage unit 66, then a determination 410 is made whether all four orders are complete on the transfer stations 64 of the pick device 62. If not, then the pick device 62 is moved to the next grid bin position 398 for a subsequent medication/supplement. If all four orders are complete, then the pick device moves to a clear position 412. Then the most recent two medications/supplements picked from the storage unit 66 are emptied 414 into the transfer nest. Then a determination 416 is made whether the designated transfer station 64 is empty and if not, then the process is returned to the empty step 414. If the transfer stations 64 are empty, then the pick device is moved 418 to the designated transfer station 64 after which the load is pushed 420 into the transfer stations 64 and then the pick status order is updated 422 and the process returns to the order acceptance step 394 for subsequent order processing.

Figure 29:
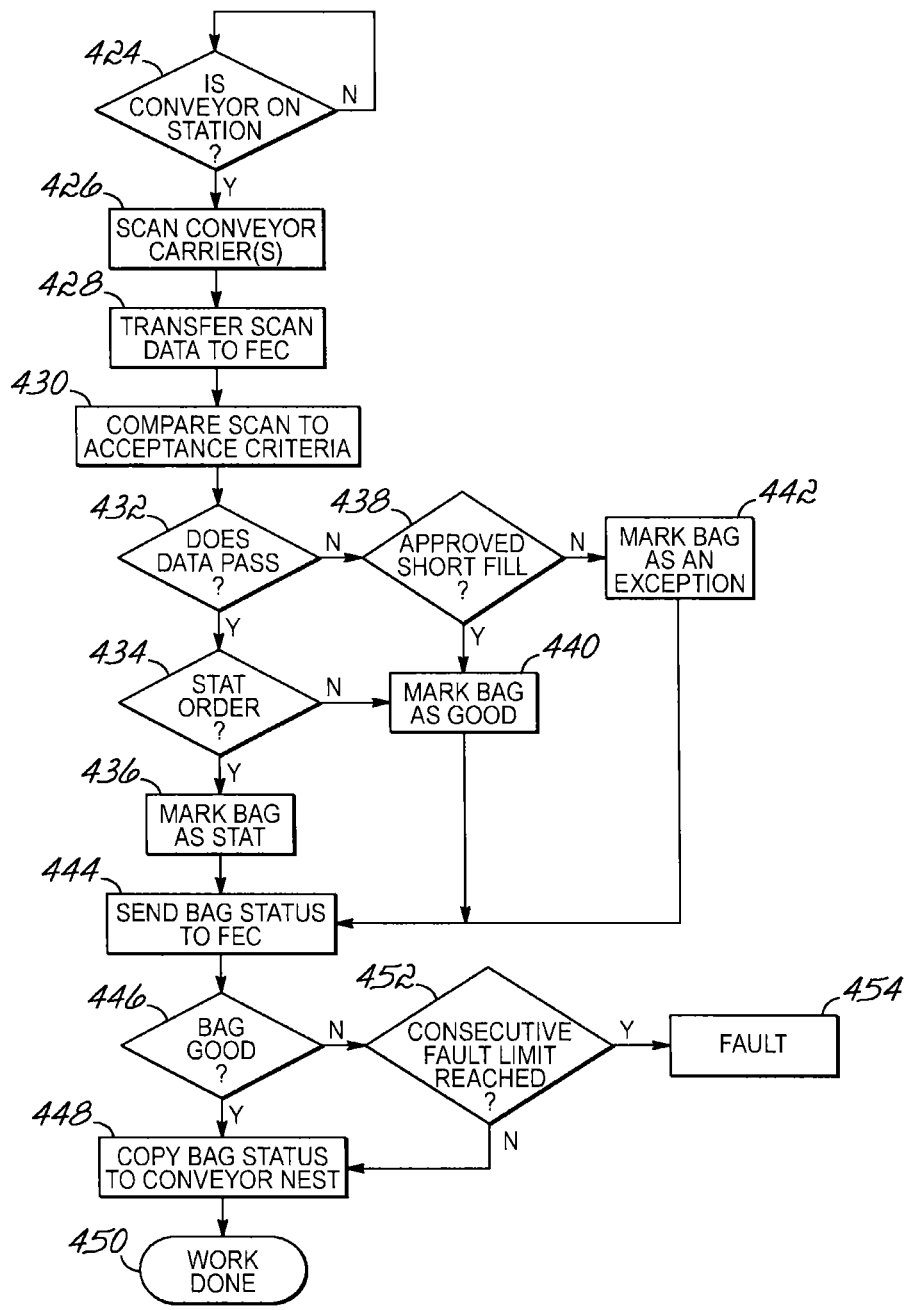
FIG. 29 is a flow diagram depicting the operation of a camera inspection system according to one embodiment of this invention.

Referring to FIG. 29, the operation of the camera station 41 is depicted. The camera station 41 scans the bar codes 24 on the packages 16 in the carriers 32 on the conveyor 30 and the FEC or control 240 compares the data collected from the camera scan with the data assigned to the conveyor carrier 32. The operation of the camera station 41 begins with a determination 424 of whether the conveyor 30 and the associated carriers 32 are appropriately positioned at the camera station 41. If not, then this process is delayed until such time as the carriers 32 carrying the associated order are at the camera station 41. If so, then the carriers are scanned 426 and then the scanned information is transferred 428 to the FEC or control 240. A comparison 430 is then made between the data for the order in the FEC or control 240 and the data retrieved from the camera station 41. If the data from the camera station 41 matches 432 that in the FEC or control 240 for the respective prescription order, then a determination 434 is made whether that order is an urgent or stat order. If so, the bag is appropriately marked 436 as a stat order. If the data scanned from the camera station is not approved because it does not correspond to the associated data in the FEC or control 240, then a determination 438 is made whether to approve the short fill order and, if so, the bag is marked 440 appropriately. If the approval of the short fill order is not accepted, then the bag is marked 442 as an exception. Whether the bag is a stat, short fill or an exception, the status of the bag is sent at 444 to the FEC or control 240 as an update. If a determination is made that the bag satisfies the order appropriately 446, then the bag status is copied at 448 to the conveyor carrier and the work is completed 450. If the bag is determined to be inadequate and the consecutive fault limit having been reached 452, a fault indicator is issued 454.

Figure 31:
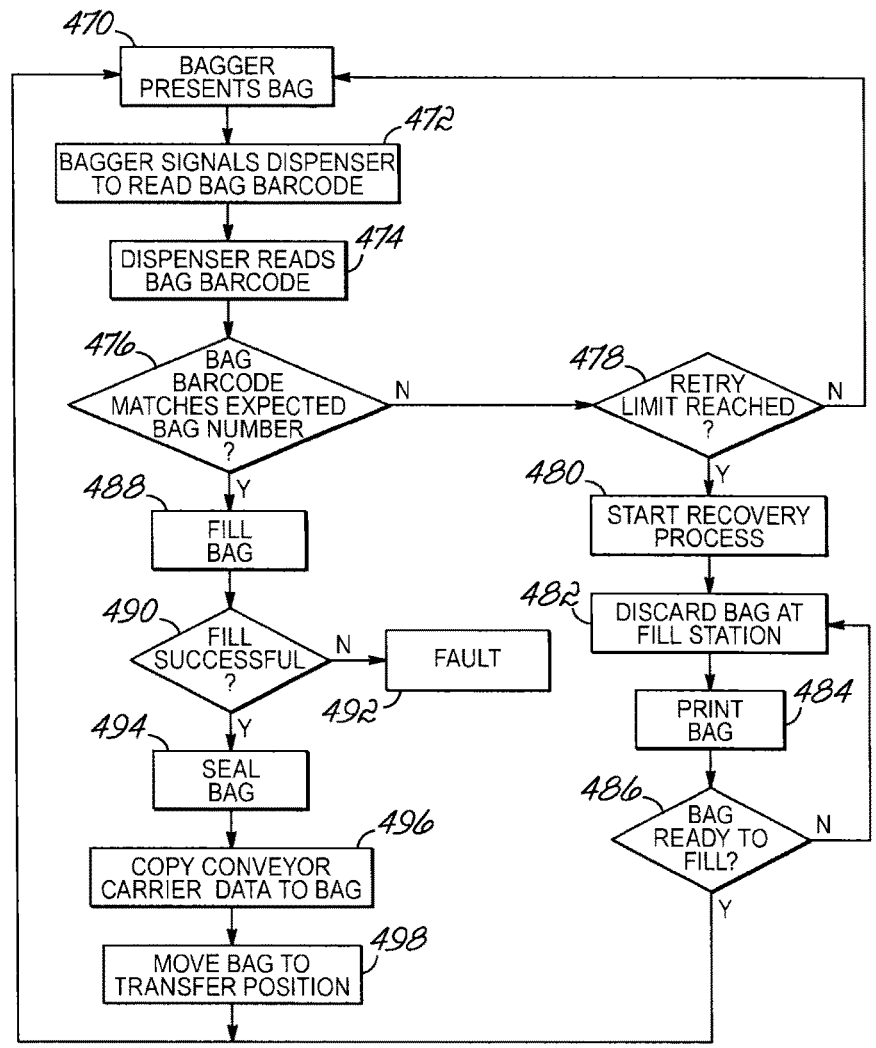
FIG. 31 is a flow diagram depicting the operation of a bagging system according to one embodiment of this invention.

The printing operation and bagging operation of embodiments of the dispensing system 10 according to this invention are shown in FIGS. 30 and 31, respectively. The bagging process is triggered by a valid bar code data being present at the packaging or bagger station 26. The print process is triggered by a valid data being assigned to the first conveyor carrier 32 processed past the camera station 41. The bag printing process operates asynchronously until a fault occurs which allows the dispensing system 10 to resolve print and bag feed errors with minimal impact on overall throughput.

Referring to FIG. 30, the operation of the printer according to one embodiment of the dispensing system 10 of this invention is described. Initially, the conveyor carrier 32 advances 456 from the camera station 41 and the bag data is assigned 458 to that conveyor carrier 32. If not, then the process begins once again. If so, a determination 460 is made whether the bag needs to be printed and, if not, then the bag data assignment step 458 is repeated. If a bag needs to be printed, then a request at 462 for information regarding the print string must be received from the FEC or control 240. Once that information is received, then the bag is printed 464 and the process returns to the initial step 456 for further operation. If the bag is not printed, then the determination 466 is made whether the time-out limit has been reached for printing of the bag and, if so, then a fault is issued 468. If not, then a subsequent request for the print string from the FEC 420 is issued at 462 until such time as the bag is printed successfully or a fault is issued.

The operation of the packaging or bagger station 26 according to one embodiment of the dispensing system 10 of this invention is described in FIG. 31 and begins with the bagger assembly presenting a bag 470. Then, the bagger signals at 472 the dispenser to read a bar code included on the bag. After the dispenser reads the bar code 474, a determination is made at 476 whether the bar code matches the bag number associated with the order to be put into the bag. If not, then a determination 478 is made whether to retry the bagger operation and to start a recovery process 480. If a recovery process is initiated, a bag is discarded at the fill station 482 and a new bag is printed 484 and, a determination is made at 486 whether the new bag is ready to be filled. If not, then that bag is discarded 482 and a subsequent bag is printed. If the bag is ready to be filled, then the process begins once again at the initial bagging operation step 470.

If the retry limit has not been reached after a mismatch is identified between the bar code on the bag and that of the prescription order at step 478, then the process begins once again at the initial step 470. If the bag bar code does match the information with the order, then the bag is filled 488 and a determination is made 490 whether the bag was filled successfully. If the bag fill was unsuccessful, then a fault signal is issued 492. If the bag was successfully filled, then the bag is sealed 494 and the next step is copying 496 the conveyor carrier data onto the bag and the bag is then moved 498 to a transfer position for ultimate delivery to the LTC facility.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

The invention claimed is:

1. An automation apparatus for dispensing individually packaged products, the apparatus comprising:
   a storage arrangement adapted to store a plurality of products each contained in an individual package, wherein the storage arrangement comprises a first and a second module, wherein the first module is adapted to store high demand products having a first frequency demand meeting a first threshold and the second module is adapted to store lower demand products having a second frequency demand meeting a second threshold that is lower than the first threshold;
   a first discharge assembly adapted to move selected ones of the individual packages from the first module of the storage arrangement without free-fall, during the selection of each of the selected individual packages;
   a second discharge assembly being of a different type than the first discharge assembly, the second discharge assembly adapted to move selected ones of the individual packages from the second module of the storage arrangement without free-fall, during the selection of each of the selected individual packages;
   a transfer station adapted to receive and hold the individual packages selected from the second discharge assembly without free-fall, during the transfer to the transfer station, of each of the selected individual packages; and
   a conveyor adapted to receive the selected individual packages from the first discharge assembly and the transfer station without free-fall, during the transfer to the conveyor, of each of the selected individual packages.

2. The apparatus of claim 1, further comprising:
   a sensor to inspect the individual packages; and
   a control device to verify that the individual packages are correct.

3. The apparatus of claim 2, wherein each individually packaged product is a medication or a supplement.

4. The apparatus of claim 1, wherein the storage arrangement further comprises:
   a plurality of storage tubes each adapted to contain a plurality of one type of product in individual packages.

5. The apparatus of claim 4, wherein the storage tubes of the first module are arranged in a linear array and oriented perpendicularly relative to a direction of travel of the conveyor and the storage tubes of the second module are arranged in a two-dimensional array and oriented obliquely relative to the conveyor direction of travel.

6. The apparatus of claim 5, wherein the second discharge assembly further comprises:
- a pick device moveable relative to the storage tubes of the second module to move selected individual packages from any of the storage tubes in the second module.

7. The apparatus of claim 1, wherein the conveyor further comprises:
- a plurality of carriers each fixedly mounted relative to each other and movable along a conveyor path, each carrier being adapted to receive a plurality of the individual packages without free-fall of each individual package received.

8. The apparatus of claim 1, wherein the discharge assembly further comprises:
- a pick device having at least one gripper movable from a first position for engaging and picking an individual package to at least a second position;
- a transfer nest proximate the gripper, the transfer nest including at least one slot for receiving one or more individual packages from the gripper, the transfer nest movable from a first position wherein the individual package can be received in the slot from the gripper, to a second position for delivering the individual package to the conveyor; and
- an actuator cooperating with the transfer nest to move the individual package from the transfer nest to the conveyor.

9. The apparatus of claim 8, wherein the transfer station is adapted to hold the individual package delivered from the transfer nest prior to delivery toward the conveyor.

10. The apparatus of claim 1, wherein the conveyor is further adapted to allow for fully unloading a filled order made up of the individual packages at a predetermined location.

11. An automation apparatus for dispensing individually packaged products, the apparatus comprising:
- a first and a second storage module each adapted to store a plurality of products each contained in an individual package, wherein the first module is adapted to store high demand products having a first frequency demand meeting a first threshold and the second module is adapted to store lower demand products having a second frequency demand meeting a second threshold that is lower than the first threshold;
- a first discharge assembly adapted to move selected ones of the individual packages from the first module of the storage arrangement while maintaining positive physical control, during the selection of each of the selected individual packages;
- a second discharge assembly, being of a different type than the first discharge assembly, the second discharge assembly adapted to move selected ones of the individual packages from the second module of the storage arrangement while maintaining positive physical control, during the selection of each of the selected individual packages;
- a transfer station adapted to receive and hold the individual packages selected from the second discharge assembly while maintaining positive physical control during the transfer to the transfer station, of each of the selected individual packages;
- a conveyor moving along a conveyor path and adapted to transfer the selected individual packages from the first discharge assembly and the transfer station to a designated space on the conveyor, while maintaining positive physical control, during the transfer to the conveyor, of each of the selected individual packages; and
- a plurality of buffer repositories in which individual packages are stored in advance of their being assembled,
- wherein each individually packaged product is a medication or a supplement.

12. The apparatus of claim 11, wherein a first buffer repository is provided via a spacing between the first and second storage modules thereby allowing a first set of individual packages from the first storage module to be discharged onto the conveyor at the designated space in advance of a second set of individual packages from the second storage module being discharged onto the conveyor at the designated space.

13. The apparatus of claim 12, wherein a second buffer repository comprises:
- a transfer nest associated with the second storage module and adapted to hold individual packages retrieved from the second storage module in advance of their placement on the conveyor at the designated space.

14. The apparatus of claim 13, wherein a third buffer repository comprises:
- the transfer station associated with the second storage module and adapted to receive individual packages from the transfer nest prior to their placement on the conveyor at the designated space.

15. A method of dispensing a selection of individually packaged products selected from a plurality of different individual packages, the method comprising:
- assigning a designated space on a conveyor for receiving the selection of individually packaged products;
- moving the designated space on the conveyor along a conveyor path past a first and a second storage module, wherein the first module is adapted to store high demand products having a first frequency demand meeting a first threshold and the second module is adapted to store lower demand products having a second frequency demand meeting a second threshold that is lower than the first threshold;
- retrieving a first subset of the selection of individually packaged products from the first storage module and a second subset of the selection of individually packaged products from the second storage module;
- moving the retrieved first subset of the selection of individually packaged products via a first discharge assembly;
- moving the retrieved second subset of the selection of individually packaged products via a second discharge assembly;
- placing the retrieved first subset of the selection of individually packaged products on the conveyor at the designated space;
- placing the retrieved second subset of the selection of individually packaged products in a transfer station and holding the selection of individually packaged products at the transfer station prior to transferring the selection of individually packaged products to the conveyor; and
- placing the retrieved second subset of the selection of individually packaged products on the conveyor at the designated space,
- wherein the individually packaged products do not free-fall during the retrieving, moving, and placing of the retrieved first and second subsets of individually packaged products.

16. The method of claim 15, further comprising:
buffering the retrieved second subset of the selection of individually packaged products while the designated space on the conveyor approaches a location of the retrieved second subset of the selection of individually packaged products.

17. The method of claim 15, wherein the second discharge assembly is a different type than the first discharge assembly.

18. The method of claim 15, wherein each individually packaged product is a medication.

19. An automation apparatus for dispensing individually packaged medications, the apparatus comprising:
- a storage arrangement adapted to store a plurality of medications each contained in an individual package, wherein the storage arrangement comprises a first and a second module, wherein the first module is adapted to store high demand medications having a first frequency demand meeting a first threshold and the second module is adapted to store lower demand medications having a second frequency demand meeting a second threshold that is lower than the first threshold;
- a first discharge assembly adapted to move selected ones of the individual packages from the first module of the storage arrangement while maintaining positive physical control, during the selection of each of the selected individual packages;
- a second discharge assembly adapted to move selected ones of the individual packages from the second module of the storage arrangement while maintaining positive physical control, during the selection of each of the selected individual packages;
- a transfer station adapted to receive and hold the individual packages selected from the second discharge assembly while maintaining positive physical control, during the transfer to the transfer station, of each of the selected individual packages;
- a conveyor adapted to receive the selected individual packages from the first discharge assembly and the transfer station while maintaining positive physical control, during the transfer to the conveyor, of each of the selected individual packages.

20. The apparatus of claim 19, wherein the second discharge assembly is of a different type than the first discharge assembly.

21. The apparatus of claim 19, wherein the first discharge assembly operates multiple times per conveyor index.

22. The apparatus of claim 19, wherein the second discharge assembly pre-processes selected ones of the individual packages.

* * * * *